(12) United States Patent
Baldwin et al.

(10) Patent No.: US 7,498,159 B2
(45) Date of Patent: Mar. 3, 2009

(54) **HETEROLOGOUS ALPHA AMYLASE EXPRESSION IN *ASPERGILLUS***

(75) Inventors: Toby M. Baldwin, Palo Alto, CA (US); Kathleen A. Clarkson, Palo Alto, CA (US); Nigel Dunn-Coleman, Palo Alto, CA (US); Suzanne E. Lantz, Palo Alto, CA (US)

(73) Assignee: Genencor International, Inc., Palo Alto, CA (US)

( * ) Notice: Subject to any disclaimer, the term of this patent is extended or adjusted under 35 U.S.C. 154(b) by 0 days.

(21) Appl. No.: 11/998,933

(22) Filed: Dec. 3, 2007

(65) Prior Publication Data

US 2008/0124764 A1  May 29, 2008

Related U.S. Application Data

(63) Continuation of application No. 11/270,864, filed on Nov. 8, 2005, now Pat. No. 7,332,319, which is a continuation-in-part of application No. 11/136,244, filed on May 24, 2005, now Pat. No. 7,354,752, said application No. 11/270,864 and a continuation-in-part of application No. 10/999,886, filed on Nov. 30, 2004, now Pat. No. 7,037,704.

(60) Provisional application No. 60/575,175, filed on May 27, 2004, provisional application No. 60/605,437, filed on Aug. 30, 2004, provisional application No. 60/647,925, filed on Jan. 28, 2005.

(51) Int. Cl.
  *C12N 1/20* (2006.01)
  *C12N 9/30* (2006.01)
  *C12N 9/34* (2006.01)
  *C12P 21/06* (2006.01)

(52) U.S. Cl. ............... 435/203; 435/254.1; 435/254.11; 435/254.3; 435/205; 435/69.1

(58) Field of Classification Search ............... None
See application file for complete search history.

(56) References Cited

U.S. PATENT DOCUMENTS

| | | | |
|---|---|---|---|
| 3,249,514 A | 5/1966 | Bode | |
| 4,092,434 A | 5/1978 | Yoshizumi et al. | |
| 4,514,496 A | 4/1985 | Yoshizumi et al. | |
| RE32,153 E | 5/1986 | Tamura et al. | |
| 4,587,215 A | 5/1986 | Hirsh | |
| 4,618,579 A | 10/1986 | Dwiggins et al. | |
| 4,863,864 A | 9/1989 | Ashikari et al. | |
| 5,093,257 A | 3/1992 | Gray | |
| 5,246,853 A | 9/1993 | Clarkson et al. | |
| 5,278,059 A | 1/1994 | Sugimoto et al. | |
| 5,364,770 A | 11/1994 | Berka et al. | |
| 5,472,864 A | 12/1995 | Bower | |
| 5,475,101 A | 12/1995 | Ward et al. | |
| 5,545,587 A | 8/1996 | Sugimoto et al. | |
| 5,736,499 A | 4/1998 | Mitchinson et al. | |
| 5,874,276 A | 2/1999 | Fowler et al. | |
| 5,958,739 A | 9/1999 | Mitchinson et al. | |
| 6,022,725 A | 2/2000 | Fowler et al. | |
| 6,093,562 A | 7/2000 | Bisgard-Frantzen et al. | |
| 6,268,328 B1 | 7/2001 | Mitchinson et al. | |
| 6,352,851 B1 | 3/2002 | Nielsen et al. | |
| 6,436,888 B1 | 8/2002 | Svendsen et al. | |
| 6,590,078 B2 | 7/2003 | Ward et al. | |
| 6,867,031 B2 | 3/2005 | Bisgard-Frantzen et al. | |

FOREIGN PATENT DOCUMENTS

| | | |
|---|---|---|
| EP | 0 171 218 B1 | 10/1993 |
| EP | 0 244 234 B2 | 11/2001 |
| EP | 0 215 594 B2 | 10/2003 |
| JP | 1995099979 A1 * | 4/1995 |
| WO | WO 84/02921 | 8/1984 |
| WO | WO 92/00381 | 1/1992 |
| WO | WO 92/06209 | 4/1992 |
| WO | WO 96/23874 | 8/1996 |
| WO | WO 96/39528 | 12/1996 |
| WO | WO 99/28488 | 7/1999 |
| WO | WO 00/04136 | 1/2000 |
| WO | WO 2004/080923 | 9/2004 |
| WO | WO 2004/111218 | 12/2004 |
| WO | WO 2005/001036 | 1/2005 |
| WO | WO 2005/001064 | 1/2005 |
| WO | WO 2005/003311 | 1/2005 |
| WO | WO 2005/003337 | 1/2005 |
| WO | WO 2005/045018 | 1/2005 |
| WO | WO 2005/052148 | 6/2005 |
| WO | WO 2005/069840 | 8/2005 |
| WO | WO 2005/117756 | 12/2005 |
| WO | WO 2005/117953 | 12/2005 |

OTHER PUBLICATIONS

Allison, Daniel S. et al., <<Transformation of the thermophilic fungus *Humicola grisea* var. *thermoidea* and overproduction of *Humicola glucoamylase*,>> Current Genetics, vol. 21, pp. 225-229, 1992.

Ashikari, Toshihiko et al., <<*Rhizopus* Raw-Starch-Degrading Glucoamylase : Its Cloning and Expression in Yeast,>> Agric. Biol. Chem., vol. 50, No. 4, pp. 957-964, 1986.

Bennett, J. W. et al., ed., <<*More Gene Manipulations in Fungi*, Academic Press, San Diego, pp. 70-76, 1991.

(Continued)

*Primary Examiner*—Rebecca E. Prouty
*Assistant Examiner*—Ganapathirama Raghu
(74) *Attorney, Agent, or Firm*—Danisco US Inc., Genencor Division

(57) ABSTRACT

The present invention relates to the co-expression and production of a heterologous alpha amylase and an endogenous glucoamylase in an *Aspergillus* strain and enzyme compositions including the same.

18 Claims, 9 Drawing Sheets

OTHER PUBLICATIONS

Bhikhabhai, Ramagauri et al., <<Isolation of Celluloytic Enzymes from *Trichoderma reesei*, QM 9414, >> Journal of Applied Biochemistry, vol. 6, pp. 336-345, 1984.

Boel, E. et al., <<Glucoamylases G1 and G2 from *Aspergillus niger* are synthesized from two different but closely related mRNAs, >> The EMBO Journal, vol. 3, No. 5, pp. 1097-1102, 1984.

Boel, E. et al., <<Two different types of intervening sequences in the glucoamylase gene from *Aspergillus niger*, >> The EMBO Journal, vol. 3, No. 7, pp. 1581-1585, 1984.

Brumbauer, Aniko et al., <<Fractionation of cellulase and β-glucosidase in a *Trichoderma reesei*, Bioseparation, vol. 7, pp. 287-295, 1999.

Campbell, Edward I. et al., <<Improved transformation efficiency of *Aspergillus niger*, Current Genetics, vol. 16, pp. 53-56, 1989.

Cao, Qing-Na et al., <<Penicillopepsin-JT2, a recombinant enzyme from *Penicillium janthinellum* and the contribution of a hydrogen bond in subsite $S_3$ to $K_{cat}$, >> Protein Science, vol . 9, pp. 991-1001, 2000.

Cees, et al. (Van den Hondel) "Heterologous Gene Expression in Filamentous Fungi," *More Gene Manipulations in Fungi*, Chapter 18, pp. 396-428, 1991, Academic Press, Inc.

Chen, Hsiu-mei et al., <<Identification and elimination by site-directed mutagenesis of thermolabile aspartyl bonds in *Aspergillus awamori* glucoamylase, >> Protein Engineering, vol. 8, No. 6, pp. 575-582, 1995.

Chen, Hsiu-mei et al., <<Effect of replacing helical glycine residues with alanines on reversible and irreversible stability and production of *Aspergillus awamori* glucoamylase, >> Protein Engineering, vol. 9, No. 6, pp. 499-505, 1996.

Chen, Frank Y. et al., >>Regulation of mammalian ribonucleotide reductase R1 mRNA stability is mediated by a ribonucleotide reductase R1 mRNA 3-untranslated region cis-trans interaction through a protein kinase C-controlled pathway, >> Biochem. J., vol. 302, pp. 125-132, 1994.

Davis, Rowland H. et al., Genetic and Microbiological Research Techniques for *Neurospora crassa*, <<Methods in Enzymology, 17A, pp. 79-143, 1970.

Ellouz, S. et al., <<Analaytical Separation of *Trichoderma reesei*, Cellulases by Ion-Exchange Fast Protein Liquid Chromatography, >> Journal of Chromatography, vol. 396, pp. 307-327, 1987.

Feldwisch et al. (Campos), <<Characterization of two membrane-associated μ-glucosidases from maize (Zea mays L.) coleoptiles, >> (1994) *Biochem J.*, 302, 15-21.

Finkelstein, David B. et al., ed., *Biotechnology of Filamentous Fungi, Technology and Products*, Chapter 6, pp. 113-156, Butterworth-Heinemann, Boston, MA, 1992.

Fliess, A. et al., <<Characterization of Cellulases by HPLC Separation, >> Eur. J. Appl. Microbiol. Biotechnol., vol. 17, pp. 314-318, 1983.

Foreman, Pamela K. et al., <<Transcriptional Regulation of Biomass-degrading Enzymes in the Filamentous Fungus *Trichoderma reesei*, >> Journal of Biological Chemistry, vol. 278, No. 34, pp. 31988-31997, Aug. 22, 2003.

Goedegebuur, Frits et al., <<Cloning and relational analysis of 15 novel fungal endoglucanases from family 12 glycosyl hydrolase, >> Current Genetics, vol. 41, pp. 89-98, 2002.

Goto, Masatoshi et al., <<The Mechanism of Binding of Glucoamylase I from *Aspergillus awamori* var. *kawachi* to Cyclodextrins and Raw Starch, >> Biosci. Biotech. Biochem., vol. 58, No. 1, pp. 49-54, 1994.

Goyal, Anil et al., <<Characteristics of Fungal Cellulases, >> Bioresource Technology, vol. 36, pp. 37-50, 1991.

Gwynne, David I. et al., <<Genetically Engineered Secretion of Active Human Interferon and a Bacterial Endoglucanase from *Aspergillus Nidulans*, >> Bio-Technology, vol. 5, pp. 713-719, Jul. 1987.

Harkki, A. et al., <<A Novel Fungal Expression System : Secretion of Active Calf Chymosin from the Filamentous Fungus *Trichoderma Reesei*, >> Bio/Technology, vol. 7, pp. 596-603, Jun. 1989.

Harkki, Anu et al., <<Genetic engineering of *Trichoderma* to produce strains with novel cellulase profiles, >> Enzyme Microb. Technol., vol. 13, pp. 227-233, Mar. 1991.

Hata, Yoji et al., <<The Glucoamylase cDNA from *Aspergillus oryzae*: Its Cloning, Nucleotide Sequence, and Expression in *Saccharomyces cerevisiae*, >> Agric. Biol. Chem., vol. 55, No. 4, pp. 941-949, 1991.

Hayashida, Shinsaku et al., <<Molecular Cloning of the Glucoamylase I Gene of *Aspergillus awamori* var. *Kawachi* for Localization of the Raw-starch-affinity Site, >> Agric. Biol. Chem., vol. 53, No. 4, pp. 923-929, 1989.

Hellman et al., <<Improvement of an <<in-Gel >> Digestion Procedure for the Micropreparation of Internal Protein Fragments for Amino Acid Sequencing, >> *Anal Biochem* V.224, 451-455, (1995).

Ilmen, Marja et al., <<Regulation of Cellulase Gene Expression in the Filamentous Fungus *Trichoderma reesei*, >> Applied and Environmental Microbiology, vol. 63, No. 4, pp. 1298-1306, Apr. 1997.

Innis, M. A. et al., <<Expression, Glycosylation, and Secretion of an *Aspergillus* Glucoamylase by *Saccharomyces cerevisiae*, >> Science, vol. 228, pp. 21-26, 1985.

Jensen, Bo et al., <<Purification of extracellular amylotic enzymes from the thermophilic fungus *Thermomyces lanuginosus*, Can. J. Microbiol., vol. 34, pp. 218-223.

Johnstone, I.L. et al., <<Cloning an *Aspergillus nidulans* developmental gene by transformation, >> The EMBO Journal, vol. 4, No. 5, pp. 1307-1311, 1985.

Juge et al., "Secretion, purification, and characterisation of barley alpha-amylase produced by heterologous gene expression in *Aspergillus niger*," Applied Microbiology and Biotechnology, V49 :4, Apr. 1998, pp. 385-392.

Kaneko, Akihiro et al., <<Molecular Cloning and Determination of the Nucleotide Sequence of a Gene Encoding an Acid-Stable α-Amylase from *Aspergillus kawachii*, Journal of Fermentation and Bioengineering, vol. 81, No. 4, pp. 292-298, 1996.

Kelly, Joan M. et al., <<Transformation of *Aspergillus niger* by the amdS gene of *Aspergillus nidulans*, The EMBO Journal, vol. 4, No. 2, pp. 475-479, 1985.

Libby, Carol Baker et al., "Effect of amino acid deletions in the O-glycosylated region of *Aspergillus awamori* glucoamylase," Protein Engineering, 7:1109-1114, 1994.

Matsubara et al., "Degradation of Raw Starch Granules by Alpha-Amylase purified from Culture of *Aspergillus awamori* KT-11," *J. of Biochem. And Molecular Biology*, V. 37 : 4, Jul. 2004 pp. 422-428.

Matsubara. T. et al., "Molecular cloning and determination of the nucleotide sequenceof raw starch digesting alpha-amylase from *Aspergillus awamori* KT-11", *J. of Biochemistry and Molecular Biology*, V37/4, Jul. 2004, pp. 429-438.

Medve, Jozsef et al., <<Ion-exchange chromatogaphic purification and quantitative analysis of *Trichoderma reessei* cellulases cellobiohydrolase I, II and endoglucanase II by fast protein liquid chromatography, >> Journal of Chromatography A, vol. 808, pp. 153-165, 1998.

Miller, Gail L., Use of Dinitrosalicyclic Acid Reagent for Determination of Reducing Sugar, >> Analytical Chemistry, vol. 31, pp. 426-428, 1959.

Morimura, Shigeru et al., "Genetic Engineering of White *Shochu-Koji* to Achieve Higher Levels of Acid-Stable αAmylase and Glucoamylase and Other Properties When Used for *Shochu* Making on a Laboratory Scale," Journal of the Institute of Brewing, vol. 105, No. 5, pp. 309-314, Sep. 1999.

Mullaney, Edward J. et al., <<Primary structure of the *trpC* gene from *Aspergillus nidulans*, >>Mol. Gen. Genet., vol. 199, pp. 37-45, 1985.

Nevalainen, K. M. Helena et al., <<The Moleclar Biology of *Trichoderma* and Its Application to the Expression of Both Homologous and Heterologous Genes, >> *Molecular Industrial Mycology*, Leong and Berka, ed., Marcel Dekker, Inc., NY, pp. 129-148, 1992.

Nunberg, Jack H. et al., <<Molecular Cloning and Characterization of the Glucoamylase Gene of *Aspergillus awamori*, >> Molecular and Cellular Biology, pp. 2306-2315, Nov. 1984.

Pourquie, J. et al., <<Scale Up of Cellulase Production and Utilization, >> *Biochemistry and Genetics of Cellulose Degradation*, Aubert, J. P. et al., ed., Academic Press, pp. 71-86, 1988.

Sheir-Neiss, G. et al., <<Characterization of the secreted cellulases of *Trichoderma reesei* wild type and mutants during controlled fermentations, >> Appl. Microbiol. Biotechnol., vol. 20, pp. 46-53, 1984.

Shibuya, Ichiro et al., <<Molecular Cloning of the Glucoamylase Gene of *Aspergillus shirousami* and Its Expression in *Aspergillus oryzae*, >> Agric. Biol. Chem., vol. 54, No. 8, pp. 1905-1914, 1990.

Swinkels, J. J. M., *Starch Conversion Technology*, van Beynum et al. ed., Marcel Dekker, Inc., New York, pp. 15-45, 1985.

Takahasi, Tomoko et al., <<Different Behavior towards Raw Starch of Three Forms of Glucoamylase from a *Rhizopus* sp., >> J. Biochem., vol. 98, pp. 663-671, 1985.

Taylor, Pamela M. et al., <<Some Properties of a Glucoamylase Produced by the Thermophilic Fungus *Humicola lanuginosa*, >>Carbohydrate Research, vol. 61, pp. 301-308, 1978.

Tomaz, Candida T. et al., <<Studies on the chromatographic fractionation of *Trichoderma reesei* cellulases by hydrophobic interaction, >> Journal of Chromatography A, vol. 865, pp. 123-128, 1999.

Tosi, Luis Ricardo Orsini et al., <<Purification and characterization of an extracellular glycoamylase from the thermophilic fungus *Humicola grisea* var. *thermoidea*, >>Can J. Microbiol., vol. 39, pp. 846-855, 1993.

Ueda et al., "Production of Ethanol from Raw Cassava Starch by a Nonconventional Fermentation Method," *Biotechnology and Bioengineering*, V23:2, 291-300 (1981).

Van Tilbeurgh, Heman et al., <<Separation of endo- and exo-type cellulases using a new affinity chromatography method, >> vol. 169, No. 2, pp. 215-218, FEBS, vol. 169, No. 2, Apr. 1984.

Ward, Michael et al., <<Use of *Aspergillus* overproducing mutants, cured for integrated plasmid, to overproduce heterologous proteins, >> Appl. Microbiol. Biotechnol., vol. 39, pp. 738-743, 1993.

Withers, Julie M. et al., "Optimization and Stability of Glucoamylase Production by Recombinant Strains of *Aspergillus niger* in Chemostat Culture," Biotechnology and Bioengineering, vol. 59, No. 4, pp. 407-418, Aug. 20, 1998>>.

Yelton, M. Melanie et al., <<Transformation of *Aspergillus nidulans* by using a *trpC* plasmid, >> *Proc. Natl. Acad. Sci.*, vol. 81, pp. 1470-1474, Mar. 1984.

* cited by examiner

```
ATGAGAGTGTCGACTTCAAGTATTGCCCTTGCTGTGTCCCTTTTTGGGAAGCTGGCCCTTGGG
CTGTCAGCTGCAGAATGGCGCACTCAATCCATCTACTTCCTTTTGACGGATCGGTTCGGTAGG
ACGGACAATTCGACTACAGCTACGTGCAATACGGGTGACCAAGTATGGTATTGCTGTACTTCC
GTCATTCATCTGCTGACTTGGATAGATCTACTGTGGTGGAAGTTGGCAAGGAATTATCAACCA
TGTTCGTATCTCACTTCATACCATCCATGCTGGGCGCTTCTGACTATTGCTCCAGCTGGACTA
TATCCAGGGCATGGGATTCACAGCTATCTGGATCTCGCCTATCACTGAGCAGCTACCCCAGGA
TACTTCGGATGGTGAAGCCTACCATGGATACTGGCAGCAGAAGATGTATGCCCTCATTGCATT
CATATTTTATGCTTACTCGCAGACTGCAGCTGACTTGGCAGATACAATGTGAACTCCAACTTC
GGCACGGCAGATGATCTGAAGTCCCTCTCCGATGCTCTTCACGCCCGCGGAATGTACCTCATG
GTCGACGTCGTCCCTAACCACATGGTAAGTACTGCTTTACCTCTATATTAGTAAACCCAATGC
GAACAATGACTGTATCAGGGCTACGCAGGTAACGGCAACGATGTGGATTACAGCGTCTTCGAC
CCCTTCGACTCCTCCTCCTACTTCCATCCATACTGCCTCATCACAGATTGGGACAACTTGACC
ATGGTCCAAGACTGTTGGGAGGGTGACACCATCGTGTCTCTGCCAGATCTGAACACCACGGAA
ACCGCCGTGAGAACCATTTGGTACGATTGGGTAGCCGACCTGGTATCCAACTACTCAGGTGCG
ACCCCAACCCACTAAAACAAGCCACATACTAAAAAATTGCTCAGTCGACGGCCTCCGTATCGA
CAGTGTCGAAGAAGTCGAACCCGACTTCTTCCCGGGCTACCAAGAAGCAGCAGGAGTCTACTG
CGTCGGTGAAGTCGACAACGGCAACCCTGCTCTCGACTGCCCATACCAAAAATATCTAGATGG
TGTTCTCAACTATCCCATGTACATACCCCCTTCTACCTTCTCGAACCCATCACTAACTCAATT
GCTGCAGCTACTGGCAACTCCTCTACGCCTTTGAATCCTCCAGCGGCAGCATCAGCAACCTCT
ACAACATGATCAAATCCGTCGCCAGCGACTGCTCCGATCCGACCCTCCTGGGCAACTTTATCG
AAAACCACGACAACCCCCGCTTCGCCTCGTATGTCCCTTCCATCACTGCCCCCTTTTAAAGTA
AACCCCACTGACAGGCAAAGCTACACATCCGACTACTCCCAAGCCAAAAACGTCCTCAGCTAC
ATCTTCCTCTCCGACGGCATCCCCATCGTCTACGCCGGCGAAGAACAGCACTACTCCGGCGGC
GACGTGCCCTACAACCGCGAAGCTACCTGGCTATCAGGCTACGACACCTCCGCGGAGCTCTAC
ACCTGGATAGCCACCACAAACGCGATCCGGAAACTAGCTATCTCAGCAGACTCGGACTACATT
ACTTACGCGGTTTGCCCTTTCCCTTCCCCCCACCCAGAGCTCAACCCCCATTCTAACAAAATA
TTTCAATGGTAGAACGACCCAATCTACACAGACAGCAACACCATCGCGATGCGCAAAGGCACC
TCCGGCTCCCAAATCATCACCGTCCTCTCCAACAAAGGCTCCTCCGGAAGCAGCTACACCCTC
ACCCTCAGCGGAAGCGGCTACACGTCCGGCACGAAGCTCATCGAAGCGTACACCTGCACGTCC
GTGACGGTGGACTCGAACGGGGATATCCCTGTGCCGATGGCTTCGGGATTACCTAGAGTTCTC
CTCCCTGCTTCGGTGGTTGATAGTTCTTCGCTTTGTGGGGGAGTGGTAACACAACCACGACC
ACAACTGCTGCTACCTCCACATCCAAAGCCACCACCTCCTCTTCTTCTTCTGCTGCTGCT
ACTACTTCTTCATCATGCACCGCAACAAGCACCACCCTCCCCATCACCTTCGAAGAACTCGTC
ACCACTACCTACGGGGAAGAAGTCTACCTCAGCGGATCTATCTCCCAGCTCGGAGAGTGGGAT
ACGAGTGACGCGGTGAAGTTGTCCGCGGATGATTATACCTCGAGTAACCCCGAGTGGTCTGTT
ACTGTGTCGTTGCCGGTGGGGACGACCTTCGAGTATAAGTTTATTAAGGTCGATGAGGGTGGA
AGTGTGACTTGGGAAAGTGATCCGAATAGGGAGTATACTGTGCCTGAATGTGGGAGTGGGAGT
GGGGAGACGGTGGTTGATACGTGGAGGTAG
```

FIG. 1

SEQ ID NO. 4

MRVSTSSIALAVSLFGKLALGLSAAEWRTQSIYFLLTDRFGRTDNSTTATCNTGDQIYCGGSW
QGIINHLDYIQGMGFTAIWISPITEQLPQDTSDGEAYHGYWQQKIYNVNSNFGTADDLKSLSD
ALHARGMYLMVDVVPNHMGYAGNGNDVDYSVFDPFDSSSYFHPYCLITDWDNLTMVQDCWEGD
TIVSLPDLNTTETAVRTIWYDWVADLVSNYSVDGLRIDSVEEVEPDFFPGYQEAAGVYCVGEV
DNGNPALDCPYQKYLDGVLNYPIYWQLLYAFESSSGSISNLYNMIKSVASDCSDPTLLGNFIE
NHDNPRFASYTSDYSQAKNVLSYIFLSDGIPIVYAGEEQHYSGGDVPYNREATWLSGYDTSAE
LYTWIATTNAIRKLAISADSDYITYANDPIYTDSNTIAMRKGTSGSQIITVLSNKGSSGSSYT
LTLSGSGYTSGTKLIEAYTCTSVTVDSNGDIPVPMASGLPRVLLPASVVDSSSLCGGSGN<u>TTT</u>
<u>TTTAATSTSKATTSSSSSSAAATTSSSC</u>TATSTTLPITFEELVTTTYGEEVYLSGSISQLGEW
DTSDAVKLSADDYTSSNPEWSVTVSLPVGTTFEYKFIKVDEGGSVTWESDPNREYTVPECGSG
SGETVVDTWR

FIG. 2

SEQ ID NO. 5

CTGCAGCCACTTGCAGTCCCGTGGAATTCTCACGGTGAATGTAGGCCTTTTGTAGGGTAGGAA
TTGTCACTCAAGCACCCCCAACCTCCATTACGCCTCCCCCATAGAGTTCCCAATCAGTGAGTC
ATGGCACTGTTCTCAAATAGATTGGGGAGAAGTTGACTTCCGCCCAGAGCTGAAGGTCGCACA
ACCGCATGATATAGGGTCGGCAACGGCAAAAAGCACGTGGCTCACCGAAAAGCAAGATGTTT
GCGATCTAACATCCAGGAACCTGGATACATCCATCATCACGCACGACCACTTTGATCTGCTGG
TAAACTCGTATTCGCCCTAAACCGAAGTGCGTGGTAAATCTACACGTGGGCCCCTTTCGGTAT
ACTGCGTGTGTCTTCTCTAGGTGCCATTCTTTTCCCTTCCTCTAGTGTTGAATTGTTTGTGTT
GGAGTCCGAGCTGTAACTACCTCTGAATCTCTGGAGAATGGTGGACTAACGACTACCGTGCAC
CTGCATCATGTATATAATAGTGATCCTGAGAAGGGGGGTTTGGAGCAATGTGGGACTTTGATG
GTCATCAAACAAAGAACGAAGACGCCTCTTTTGCAAAGTTTTGTTTCGGCTACGGTGAAGAAC
TGGATACTTGTTGTGTCTTCTGTGTATTTTTGTGGCAACAAGAGGCCAGAGACAATCTATTCA
ACACCAAGCTTGCTCTTTTGAGCTACAAGAACCTGTGGGGTATATATCTAGAGTTGTGAAGT
CGGTAATCCCGCTGTATAGTAATACGAGTCGCATCTAAATACTCCGAAGCTGCTGCGAACCCG
GAGAATCGAGATGTGCTGGAAAGCTTCTAGCGAGCGGCTAAATTAGCATGAAAGGCTATGAGA
AATTCTGGAGACGGCTTGTTGAATCATGGCGTTCCATTCTTCGACAAGCAAAGCGTTCCGTCG
CAGTAGCAGGCACTCATTCCCGAAAAAACTCGGAGATTCCTAAGTAGCGATGGAACCGGAATA
ATATAATAGGCAATACATTGAGTTGCCTCGACGGTTGCAATGCAGGGGTACTGAGCTTGGACA
TAACTGTTCCGTACCCCACCTCTTCTCAACCTTTGGCGTTTCCCTGATTCAGCGTACCCGTAC
AAGTCGTAATCACTATTAACCCAGACTGACCGGACGTGTTTGCCCTTCATTTGGAGAAATAA
TGTCATTGCGATGTGTAATTTGCCTGCTTGACCGACTGGGGCTGTTCGAAGCCCGAATGTAGG
ATTGTTATCCGAACTCTGCTCGTAGAGGCATGTTGTAATCTGTGTCGGGCAGGACACGCCTC
GAAGGTTCACGGCAAGGGAAACCACCGATAGCAGTGTCTAGTAGCAACCTGTAAAGCCGCAAT
GCAGCATCACTGGAAAATACAAACCAATGGCTAAAAGTACATAAGTTAATGCCTAAAGAAGTC
ATATACCAGCGGCTAATAATTGTACAATCAAGTGGCTAAACGTACCGTAATTTGCCAACGGCT
TGTGGGGTTGCAGAAGCAACGGCAAAGCCCCACTTCCCCACGTTTGTTTCTTCACTCAGTCCA
ATCTCAGCTGGTGATCCCCCAATTGGGTCGCTTGTTTGTTCCGGTGAAGTGAAAGAAGACAGA
GGTAAGAATGTCTGACTCGGAGCGTTTTGCATACAACCAAGGGCAGTGATGGAAGACAGTGAA
ATGTTGACATTCAAGGAGTATTTAGCCAGGGATGCTTGAGTGTATCGTGTAAGGAGGTTTGTC
TGCCGATACGACGAATACTGTATAGTCACTTCTGATGAAGTGGTCCATATTGAAATGTAAGTC
GGCACTGAACAGGCAAAAGATTGAGTTGAAACTGCCTAAGATCTCGGGCCCTCGGGCCTTCGG

FIG. 3A

```
CCTTTGGGTGTACATGTTTGTGCTCCGGGCAAATGCAAAGTGTGGTAGGATCGAACACACTGC
TGCCTTTACCAAGCAGCTGAGGGTATGTGATAGGCAAATGTTCAGGGGCCACTGCATGGTTTC
GAATAGAAAGAGAAGCTTAGCCAAGAACAATAGCCGATAAAGATAGCCTCATTAAACGGAATG
AGCTAGTAGGCAAAGTCAGCGAATGTGTATATATAAAGGTTCGAGGTCCGTGCCTCCCTCATG
CTCTCCCCATCTACTCATCAACTCAGATCCTCCAGGAGACTTGTACACCATCTTTTGAGGCAC
AGAAACCCAATAGTCAACCATCACAAGTTTGTACAAAAAAGCAGGCTCCGCGGCCGCCCCCTT
CAcCATGAGAGTGTCGACTTCAAGTATTGCCCTTGCTGTGTCCCTTTTTGGGAAGCTGGCCCT
TGGGCTGTCAGCTGCAGAATGGCGCACTCAATCCATCTACTTCCTTTTGACGGATCGGTTCGG
TAGGACGGACAATTCGACTACAGCTACGTGCAATACGGGTGACCAAGTATGGTATTGCTGTAC
TTCCGTCATTCATCTGCTGACTTGGATAGATCTACTGTGGTGGAAGTTGGCAAGGAATTATCA
ACCATGTTCGTATCTCACTTCATACCATCCATGCTGGGCGCTTCTGACTATTGCTCCAGCTGG
ACTATATCCAGGGCATGGGATTCACAGCTATCTGGATCTCGCCTATCACTGAGCAGCTACCCC
AGGATACTTCGGATGGTGAAGCCTACCATGGATACTGGCAGCAGAAGATGTATGCCCTCATTG
CATTCATATTTTATGCTTACTCGCAGACTGCAGCTGACTTGGCAGATACAATGTGAACTCCAA
CTTCGGCACGGCAGATGATCTGAAGTCCCTCTCCGATGCTCTTCACGCCCGCGGAATGTACCT
CATGGTCGACGTCGTCCCTAACCACATGGTAAGTACTGCTTTACCTCTATATTAGTAAACCCA
ATGCGAACAATGACTGTATCAGGGCTACGCAGGTAACGGCAACGATGTGGATTACAGCGTCTT
CGACCCCTTCGACTCCTCCTCCTACTTCCATCCATACTGCCTCATCACAGATTGGGACAACTT
GACCATGGTCCAAGACTGTTGGGAGGGTGACACCATCGTGTCTCTGCCAGATCTGAACACCAC
GGAAACCGCCGTGAGAACCATTTGGTACGATTGGGTAGCCGACCTGGTATCCAACTACTCAGG
TGCGACCCCAACCCACTAAAACAAGCCACATACTAAAAAATTGCTCAGTCGACGGCCTCCGTA
TCGACAGTGTCGAAGAAGTCGAACCCGACTTCTTCCCGGGCTACCAAGAAGCAGCAGGAGTCT
ACTGCGTCGGTGAAGTCGACAACGGCAACCCTGCTCTCGACTGCCCATACCAAAAATATCTAG
ATGGTGTTCTCAACTATCCCATGTACATACCCCCTTCTACCTTCTCGAACCCATCACTAACTC
AATTGCTGCAGCTACTGGCAACTCCTCTACGCCTTTGAATCCTCCAGCGGCAGCATCAGCAAC
CTCTACAACATGATCAAATCCGTCGCCAGCGACTGCTCCGATCCGACCCTCCTGGGCAACTTT
ATCGAAAACCACGACAACCCCCGCTTCGCCTCGTATGTCCCTTCCATCACTGCCCCCTTTTAA
AGTAAACCCCACTGACAGGCAAAGCTACACATCCGACTACTCCCAAGCCAAAAACGTCCTCAG
CTACATCTTCCTCTCCGACGGCATCCCCATCGTCTACGCCGGCGAAGAACAGCACTACTCCGG
CGGCGACGTGCCCTACAACCGCGAAGCTACCTGGCTATCAGGCTACGACACCTCCGCGGAGCT
CTACACCTGGATAGCCACCACAAACGCGATCCGGAAACTAGCTATCTCAGCAGACTCGGACTA
CATTACTTACGCGGTTTGCCCTTTCCCTTCCCCCCACCCAGAGCTCAACCCCCATTCTAACAA
AATATTTCAATGGTAGAACGACCCAATCTACACAGACAGCAACACCATCGCGATGCGCAAAGG
CACCTCCGGCTCCCAAATCATCACCGTCCTCTCCAACAAAGGCTCCTCCGGAAGCAGCTACAC
CCTCACCCTCAGCGGAAGCGGCTACACGTCCGGCACGAAGCTCATCGAAGCGTACACCTGCAC
GTCCGTGACGGTGGACTCGAACGGGGATATCCCTGTGCCGATGGCTTCGGGATTACCTAGAGT
TCTCCTCCCTGCTTCGGTGGTTGATAGTTCTTCGCTTTGTGGGGGAGTGGTAACACAACCAC
GACCACAACTGCTGCTACCTCCACATCCAAAGCCACCACCTCCTCTTCTTCTTCTTCTGCTGC
TGCTACTACTTCTTCATCATGCACCGCAACAAGCACCACCCTCCCCATCACCTTCGAAGAACT
CGTCACCACTACCTACGGGGAAGAAGTCTACCTCAGCGGATCTATCTCCCAGCTCGGAGAGTG
GGATACGAGTGACGCGGTGAAGTTGTCCGCGGATGATTATACCTCGAGTAACCCCGAGTGGTC
TGTTACTGTGTCGTTGCCGGTGGGGACGACCTTCGAGTATAAGTTTATTAAGGTCGATGAGGG
TGGAAGTGTGACTTGGGAAAGTGATCCGAATAGGGAGTATACTGTGCCTGAATGTGGGAGTGG
GAGTGGGGAGACGGTGGTTGATACGTGGAGGTAGAAGGGTGGGCGCGCCGACCCAGCTTTCTT
GTACAAAGTGGTGATCGCGCCAGCTCCGTGCGAAAGCCTGACGCACCGGTAGATTCTTGGTGA
GCCCGTATCATGACGGCGGCGGGAGCTACATGGCCCCGGGTGATTTATTTTTTTTGTATCTAC
TTCTGACCCTTTTCAAATATACGGTCAACTCATCTTTCACTGGAGATGCGGCCTGCTTGGTAT
TGCGATGTTGTCAGCTTGGCAAATTGTGGCTTTCGAAAACACAAAACGATTCCTTAGTAGCCA
TGCATTTTAAGATAACGGAATAGAAGAAAGAGGAAATTAAAAAAAAAAAAAAAACAAACATCC
```

*FIG. 3B*

```
CGTTCATAACCCGTAGAATCGCCGCTCTTCGTGTATCCCAGTACCAGTTTATTTTGAATAGCT
CGCCCGCTGGAGAGCATCCTGAATGCAAGTAACAACCGTAGAGGCTGACACGGCAGGTGTTGC
TAGGGAGCGTCGTGTTCTACAAGGCCAGACGTCTTCGCGGTTGATATATATGTATGTTTGACT
GCAGGCTGCTCAGCGACGACAGTCAAGTTCGCCCTCGCTGCTTGTGCAATAATCGCAGTGGGG
AAGCCACACCGTGACTCCCATCTTTCAGTAAAGCTCTGTTGGTGTTTATCAGCAATACACGTA
ATTTAAACTCGTTAGCATGGGGCTGATAGCTTAATTACCGTTTACCAGTGCCATGGTTCTGCA
GCTTTCCTTGGCCCGTAAAATTCGGCGAAGCCAGCCAATCACCAGCTAGGCACCAGCTAAACC
CTATAATTAGTCTCTTATCAACACCATCCGCTCCCCGGGATCAATGAGGAGAATGAGGGGGA
TGCGGGGCTAAAGAAGCCTACATAACCCTCATGCCAACTCCCAGTTTACACTCGTCGAGCCAA
CATCCTGACTATAAGCTAACACAGAATGCCTCAATCCTGGGAAGAACTGGCCGCTGATAAGCG
CGCCCGCCTCGCAAAAACCATCCCTGATGAATGGAAAGTCCAGACGCTGCCTGCGGAAGACAG
CGTTATTGATTTCCCAAAGAAATCGGGGATCCTTTCAGAGGCCGAACTGAAGATCACAGAGGC
CTCCGCTGCAGATCTTGTGTCCAAGCTGGCGGCCGGAGAGTTGACCTCGGTGGAAGTTACGCT
AGCATTCTGTAAACGGGCAGCAATCGCCCAGCAGTTAGTAGGGTCCCCTCTACCTCTCAGGGA
GATGTAACAACGCCACCTTATGGGACTATCAAGCTGACGCTGGCTTCTGTGCAGACAAACTGC
GCCCACGAGTTCTTCCCTGACGCCGCTCTCGCGCAGGCAAGGGAACTCGATGAATACTACGCA
AAGCACAAGAGACCCGTTGGTCCACTCCATGGCCTCCCCATCTCTCTCAAAGACCAGCTTCGA
GTCAAGGTACACCGTTGCCCCTAAGTCGTTAGATGTCCCTTTTTGTCAGCTAACATATGCCAC
CAGGGCTACGAAACATCAATGGGCTACATCTCATGGCTAAACAAGTACGACGAAGGGGACTCG
GTTCTGACAACCATGCTCCGCAAAGCCGGTGCCGTCTTCTACGTCAAGACCTCTGTCCCGCAG
ACCCTGATGGTCTGCGAGACAGTCAACAACATCATCGGGCGCACCGTCAACCCACGCAACAAG
AACTGGTCGTGCGGCGGCAGTTCTGGTGGTGAGGGTGCGATCGTTGGGATTCGTGGTGGCGTC
ATCGGTGTAGGAACGGATATCGGTGGCTCGATTCGAGTGCCGGCCGCGTTCAACTTCCTGTAC
GGTCTAAGGCCGAGTCATGGGCGGCTGCCGTATGCAAAGATGGCGAACAGCATGGAGGGTCAG
GAGACGGTGCACAGCGTTGTCGGGCCGATTACGCACTCTGTTGAGGGTGAGTCCTTCGCCTCT
TCCTTCTTTTCCTGCTCTATACCAGGCCTCCACTGTCCTCCTTTCTTGCTTTTTATACTATAT
ACGAGACCGGCAGTCACTGATGAAGTATGTTAGACCTCCGCCTCTTCACCAAATCCGTCCTCG
GTCAGGAGCCATGGAAATACGACTCCAAGGTCATCCCCATGCCCTGGCGCCAGTCCGAGTCGG
ACATTATTGCCTCCAAGATCAAGAACGGCGGGCTCAATATCGGCTACTACAACTTCGACGGCA
ATGTCCTTCCACACCCTCCTATCCTGCGCGGCGTGGAAACCACCGTCGCCGCACTCGCCAAAG
CCGGTCACACCGTGACCCCGTGGACGCCATACAAGCACGATTTCGGCCACGATCTCATCTCCC
ATATCTACGCGGCTGACGGCAGCGCCGACGTAATGCGCGATATCAGTGCATCCGGCGAGCCGG
CGATTCCAAATATCAAAGACCTACTGAACCCGAACATCAAAGCTGTTAACATGAACGAGCTCT
GGGACACGCATCTCCAGAAGTGGAATTACCAGATGGAGTACCTTGAGAAATGGCGGGAGGCTG
AAGAAAAGGCCGGGAAGGAACTGGACGCCATCATCGCGCCGATTACGCCTACCGCTGCGGTAC
GGCATGACCAGTTCCGGTACTATGGGTATGCCTCTGTGATCAACCTGCTGGATTTCACGAGCG
TGGTTGTTCCGGTTACCTTTGCGGATAAGAACATCGATAAGAAGAATGAGAGTTTCAAGGCGG
TTAGTGAGCTTGATGCCCTCGTGCAGGAAGAGTATGATCCGGAGGCGTACCATGGGGCACCGG
TTGCAGTGCAGGTTATCGGACGGAGACTCAGTGAAGAGAGGACGTTGGCGATTGCAGAGGAAG
TGGGGAAGTTGCTGGGAAATGTGGTGACTCCATAGCTAATAAGTGTCAGATAGCAATTTGCAC
AAGAAATCAATACCAGCAACTGTAAATAAGCGCTGAAGTGACCATGCCATGCTACGAAAGAGC
AGAAAAAAACCTGCCGTAGAACCGAAGAGATATGACACGCTTCCATCTCTCAAAGGAAGAATC
CCTTCAGGGTTGCGTTTCCAGTCTAGACACGTATAACGGCACAAGTGTCTCTCACCAAATGGG
TTATATCTCAAATGTGATCTAAGGATGGAAAGCCCAGAATATCGATCGCGCGCAGATCCATAT
ATAGGGCCCGGGTTATAATTACCTCAGGTCGACGTCCATGGCCATTCGAATTCGTAATCATG
GTCATAGCTGTTTCCTGTGTGAAATTGTTATCCGCTCACAATTCCACACAACATACGAGCCGG
AAGCATAAAGTGTAAAGCCTGGGGTGCCTAATGAGTGAGCTAACTCACATTAATTGCGTTGCG
CTCACTGCCCGCTTTCCAGTCGGGAAACCTGTCGTGCCAGCTGCATTAATGAATCGGCCAACG
CGCGGGGAGAGGCGGTTTGCGTATTGGGCGCTCTTCCGCTTCCTCGCTCACTGACTCGCTGCG
```

*FIG. 3C*

```
CTCGGTCGTTCGGCTGCGGCGAGCGGTATCAGCTCACTCAAAGGCGGTAATACGGTTATCCAC
AGAATCAGGGGATAACGCAGGAAAGAACATGTGAGCAAAAGGCCAGCAAAAGGCCAGGAACCG
TAAAAAGGCCGCGTTGCTGGCGTTTTTCCATAGGCTCCGCCCCCCTGACGAGCATCACAAAAA
TCGACGCTCAAGTCAGAGGTGGCGAAACCCGACAGGACTATAAAGATACCAGGCGTTTCCCCC
TGGAAGCTCCCTCGTGCGCTCTCCTGTTCCGACCCTGCCGCTTACCGGATACCTGTCCGCCTT
TCTCCCTTCGGGAAGCGTGGCGCTTTCTCATAGCTCACGCTGTAGGTATCTCAGTTCGGTGTA
GGTCGTTCGCTCCAAGCTGGGCTGTGTGCACGAACCCCCCGTTCAGCCCGACCGCTGCGCCTT
ATCCGGTAACTATCGTCTTGAGTCCAACCCGGTAAGACACGACTTATCGCCACTGGCAGCAGC
CACTGGTAACAGGATTAGCAGAGCGAGGTATGTAGGCGGTGCTACAGAGTTCTTGAAGTGGTG
GCCTAACTACGGCTACACTAGAAGAACAGTATTTGGTATCTGCGCTCTGCTGAAGCCAGTTAC
CTTCGGAAAAAGAGTTGGTAGCTCTTGATCCGGCAAACAAACCACCGCTGGTAGCGGTGGTTT
TTTTGTTTGCAAGCAGCAGATTACGCGCAGAAAAAAAGGATCTCAAGAAGATCCTTTGATCTT
TTCTACGGGGTCTGACGCTCAGTGGAACGAAAACTCACGTTAAGGGATTTTGGTCATGAGATT
ATCAAAAAGGATCTTCACCTAGATCCTTTTAAATTAAAAATGAAGTTTTAAATCAATCTAAAG
TATATATGAGTAAACTTGGTCTGACAGTTACCAATGCTTAATCAGTGAGGCACCTATCTCAGC
GATCTGTCTATTTCGTTCATCCATAGTTGCCTGACTCCCCGTCGTGTAGATAACTACGATACG
GGAGGGCTTACCATCTGGCCCCAGTGCTGCAATGATACCGCGAGACCCACGCTCACCGGCTCC
AGATTTATCAGCAATAAACCAGCCAGCCGGAAGGGCCGAGCGCAGAAGTGGTCCTGCAACTTT
ATCCGCCTCCATCCAGTCTATTAATTGTTGCCGGGAAGCTAGAGTAAGTAGTTCGCCAGTTAA
TAGTTTGCGCAACGTTGTTGCCATTGCTACAGGCATCGTGGTGTCACGCTCGTCGTTTGGTAT
GGCTTCATTCAGCTCCGGTTCCCAACGATCAAGGCGAGTTACATGATCCCCCATGTTGTGCAA
AAAAGCGGTTAGCTCCTTCGGTCCTCCGATCGTTGTCAGAAGTAAGTTGGCCGCAGTGTTATC
ACTCATGGTTATGGCAGCACTGCATAATTCTCTTACTGTCATGCCATCCGTAAGATGCTTTTC
TGTGACTGGTGAGTACTCAACCAAGTCATTCTGAGAATAGTGTATGCGGCGACCGAGTTGCTC
TTGCCCGGCGTCAATACGGGATAATACCGCGCCACATAGCAGAACTTTAAAAGTGCTCATCAT
TGGAAAACGTTCTTCGGGGCGAAAACTCTCAAGGATCTTACCGCTGTTGAGATCCAGTTCGAT
GTAACCCACTCGTGCACCCAACTGATCTTCAGCATCTTTTACTTTCACCAGCGTTTCTGGGTG
AGCAAAAACAGGAAGGCAAAATGCCGCAAAAAAGGGAATAAGGGCGACACGGAAATGTTGAAT
ACTCATACTCTTCCTTTTTCAATATTATTGAAGCATTTATCAGGGTTATTGTCTCATGAGCGG
ATACATATTTGAATGTATTTAGAAAAATAAACAAATAGGGGTTCCGCGCACATTTCCCCGAAA
AGTGCCACCTGACGTCTAAGAAACCATTATTATCATGACATTAACCTATAAAAATAGGCGTAT
CACGAGGCCCTTTCGTCTCGCGCGTTTCGGTGATGACGGTGAAAACCTCTGACACATGCAGCT
CCCGGAGACGGTCACAGCTTGTCTGTAAGCGGATGCCGGGAGCAGACAAGCCCGTCAGGGCGC
GTCAGCGGGTGTTGGCGGGTGTCGGGGCTGGCTTAACTATGCGGCATCAGAGCAGATTGTACT
GAGAGTGCACCATAAAATTGTAAACGTTAATATTTTGTTAAAATTCGCGTTAAATTTTGTTA
AATCAGCTCATTTTTTAACCAATAGGCCGAAATCGGCAAAATCCCTTATAAATCAAAAGAATA
GCCCGAGATAGGGTTGAGTGTTGTTCCAGTTTGGAACAAGAGTCCACTATTAAAGAACGTGGA
CTCCAACGTCAAAGGGCGAAAAACCGTCTATCAGGGCGATGGCCCACTACGTGAACCATCACC
CAAATCAAGTTTTTTGGGGTCGAGGTGCCGTAAAGCACTAAATCGGAACCCTAAAGGGAGCCC
CCGATTTAGAGCTTGACGGGGAAAGCCGGCGAACGTGGCGAGAAAGGAAGGGAAGAAAGCGAA
AGGAGCGGGCGCTAGGGCGCTGGCAAGTGTAGCGGTCACGCTGCGCGTAACCACCACACCCGC
CGCGCTTAATGCGCCGCTACAGGGCGCGTACTATGGTTGCTTTGACGTATGCGGTGTGAAATA
CCGCACAGATGCGTAAGGAGAAAATACCGCATCAGGCGCCATTCGCCATTCAGGCTGCGCAAC
TGTTGGGAAGGGCGATCGGTGCGGGCCTCTTCGCTATTACGCCAGCTGGCGAAAGGGGGATGT
GCTGCAAGGCGATTAAGTTGGGTAACGCCAGGGTTTTCCCAGTCACGACGTTGTAAAACGACG
GCCAGTGCCCAAGCTTACTAGTACTTCTCGAGCTCTGTACATGTCCGGTCGCGACGTACGCGT
ATCGATGGCGCCAGCTGCAGGCGGCCGC
```

FIG. 3D

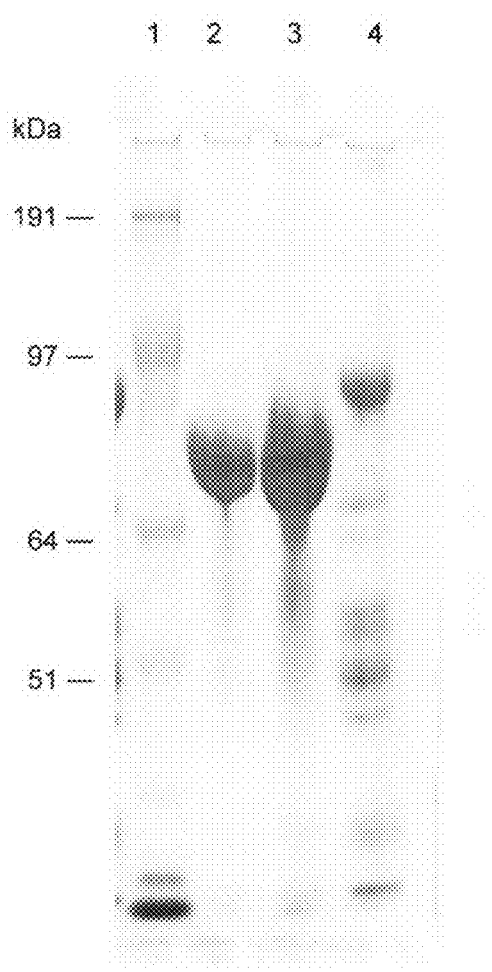 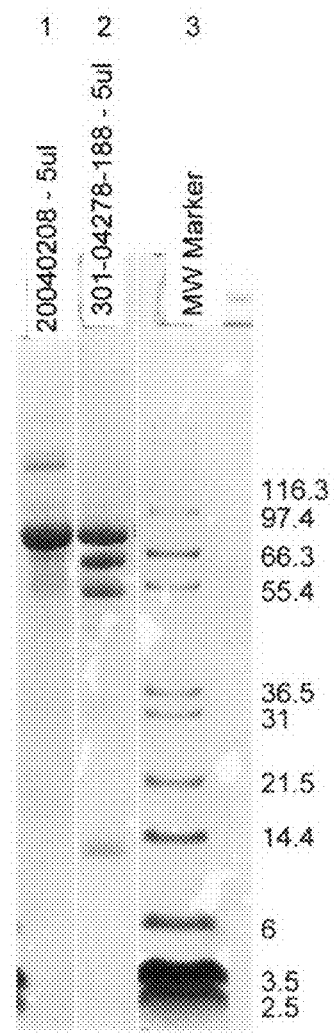
*FIG. 6A*    *FIG. 6B*

SEQUENCE LISTING

```
<160> NUMBER OF SEQ ID NOS: 14

<210> SEQ ID NO 1
<211> LENGTH: 2361
<212> TYPE: DNA
<213> ORGANISM: Aspergillus kawachi

<400> SEQUENCE: 1
atgagagtgt cgacttcaag tattgccctt gctgtgtccc tttttgggaa gctggccctt      60
gggctgtcag ctgcagaatg gcgcactcaa tccatctact tcctttttgac ggatcggttc     120 ggtaggacgg acaattcgac tacagctacg tgcaatacgg gtgaccaagt atggtattgc     180
tgtacttccg tcattcatct gctgacttgg atagatctac tgtggtggaa gttggcaagg     240
```

| | |
|---|---|
| aattatcaac catgttcgta tctcacttca taccatccat gctgggcgct tctgactatt | 300 |
| gctccagctg gactatatcc agggcatggg attcacagct atctggatct cgcctatcac | 360 |
| tgagcagcta ccccaggata cttcggatgg tgaagcctac catggatact ggcagcagaa | 420 |
| gatgtatgcc ctcattgcat tcatatttta tgcttactcg cagactgcag ctgacttggc | 480 |
| agatacaatg tgaactccaa cttcggcacg gcagatgatc tgaagtccct ctccgatgct | 540 |
| cttcacgccc gcggaatgta cctcatggtc gacgtcgtcc ctaaccacat ggtaagtact | 600 |
| gctttacctc tatattagta aacccaatgc gaacaatgac tgtatcaggg ctacgcaggt | 660 |
| aacggcaacg atgtggatta cagcgtcttc gacccctccg actcctcctc ctacttccat | 720 |
| ccatactgcc tcatcacaga ttgggacaac ttgaccatgg tccaagactg ttgggagggt | 780 |
| gacaccatcg tgtctctgcc agatctgaac accacgaaaa ccgccgtgag aaccatttgg | 840 |
| tacgattggg tagccgacct ggtatccaac tactcaggtg cgaccccaac ccactaaaac | 900 |
| aagccacata ctaaaaaatt gctcagtcga cggcctccgt atcgacagtg tcgaagaagt | 960 |
| cgaacccgac ttcttcccgg gctaccaaga agcagcagga gtctactgcg tcggtgaagt | 1020 |
| cgacaacggc aaccctgctc tcgactgccc ataccaaaaa tatctagatg gtgttctcaa | 1080 |
| ctatcccatg tacatacccc cttctacctt ctcgaaccca tcactaactc aattgctgca | 1140 |
| gctactggca actcctctac gcctttgaat cctccagcgg cagcatcagc aacctctaca | 1200 |
| acatgatcaa atccgtcgcc agcgactgct ccgatccgac cctcctgggc aactttatcg | 1260 |
| aaaaccacga caaccccgc ttcgcctcgt atgtcccttc catcactgcc ccctttttaaa | 1320 |
| gtaaaccccca ctgacaggca aagctacaca tccgactact cccaagccaa aaacgtcctc | 1380 |
| agctacatct tcctctccga cggcatcccc atcgtctacg ccggcgaaga acagcactac | 1440 |
| tccggcggcg acgtgcccta caaccgcgaa gctacctggc tatcaggcta cgacacctcc | 1500 |
| gcggagctct acacctggat agccaccaca aacgcgatcc ggaaactagc tatctcagca | 1560 |
| gactcggact acattactta cgcggttgtc cctttccctt cccccacccc agagctcaac | 1620 |
| ccccattcta acaaaatatt tcaatggtag aacgacccaa tctacacaga cagcaacacc | 1680 |
| atcgcgatgc gcaaaggcac ctccggctcc caaatcatca ccgtcctctc caacaaaggc | 1740 |
| tcctccggaa gcagctacac cctcaccctc agcggaagcg gctacacgtc cggcacgaag | 1800 |
| ctcatcgaag cgtacacctg cacgtccgtg acggtggact cgaacgggga tatccctgtg | 1860 |
| ccgatggctt cgggattacc tagagttctc ctccctgctt cggtggttga tagttcttcg | 1920 |
| cttttgtgggg ggagtggtaa cacaaccacg accacaactg ctgctacctc cacatccaaa | 1980 |
| gccaccacct cctcttcttc ttcttctgct gctgctacta cttcttcatc atgcaccgca | 2040 |
| acaagcacca ccctccccat caccttcgaa gaactcgtca ccactaccta cggggaagaa | 2100 |
| gtctacctca gcggatctat ctcccagctc ggagagtggg atacgagtga cgcggtgaag | 2160 |
| ttgtccgcgg atgattatac ctcgagtaac cccgagtggt ctgttactgt gtcgttgccg | 2220 |
| gtggggacga ccttcgagta taagtttatt aaggtcgatg agggtggaag tgtgacttgg | 2280 |
| gaaagtgatc cgaatagggga gtatactgtg cctgaatgtg ggagtgggag tggggagacg | 2340 |
| gtggttgata cgtggaggta g | 2361 |

<210> SEQ ID NO 2
<211> LENGTH: 21
<212> TYPE: PRT
<213> ORGANISM: Aspergillus kawachi

<400> SEQUENCE: 2

Met Arg Val Ser Thr Ser Ser Ile Ala Leu Ala Val Ser Leu Phe Gly
1               5                   10                  15

Lys Leu Ala Leu Gly
20

<210> SEQ ID NO 3
<211> LENGTH: 619
<212> TYPE: PRT
<213> ORGANISM: Aspergillus kawachi

<400> SEQUENCE: 3

Leu Ser Ala Ala Glu Trp Arg Thr Gln Ser Ile Tyr Phe Leu Leu Thr
1               5                   10                  15

Asp Arg Phe Gly Arg Thr Asp Asn Ser Thr Thr Ala Thr Cys Asn Thr
            20                  25                  30

Gly Asp Gln Ile Tyr Cys Gly Gly Ser Trp Gln Gly Ile Ile Asn His
        35                  40                  45

Leu Asp Tyr Ile Gln Gly Met Gly Phe Thr Ala Ile Trp Ile Ser Pro
50                  55                  60

Ile Thr Glu Gln Leu Pro Gln Asp Thr Ser Asp Gly Glu Ala Tyr His
65                  70                  75                  80

Gly Tyr Trp Gln Gln Lys Ile Tyr Asn Val Asn Ser Asn Phe Gly Thr
                85                  90                  95

Ala Asp Asp Leu Lys Ser Leu Ser Asp Ala Leu His Ala Arg Gly Met
            100                 105                 110

Tyr Leu Met Val Asp Val Val Pro Asn His Met Gly Tyr Ala Gly Asn
        115                 120                 125

Gly Asn Asp Val Asp Tyr Ser Val Phe Asp Pro Phe Asp Ser Ser Ser
130                 135                 140

Tyr Phe His Pro Tyr Cys Leu Ile Thr Asp Trp Asp Asn Leu Thr Met
145                 150                 155                 160

Val Gln Asp Cys Trp Glu Gly Asp Thr Ile Val Ser Leu Pro Asp Leu
                165                 170                 175

Asn Thr Thr Glu Thr Ala Val Arg Thr Ile Trp Tyr Asp Trp Val Ala
            180                 185                 190

Asp Leu Val Ser Asn Tyr Ser Val Asp Gly Leu Arg Ile Asp Ser Val
        195                 200                 205

Glu Glu Val Glu Pro Asp Phe Phe Pro Gly Tyr Gln Glu Ala Ala Gly
210                 215                 220

Val Tyr Cys Val Gly Glu Val Asp Asn Gly Asn Pro Ala Leu Asp Cys
225                 230                 235                 240

Pro Tyr Gln Lys Tyr Leu Asp Gly Val Leu Asn Tyr Pro Ile Tyr Trp
                245                 250                 255

Gln Leu Leu Tyr Ala Phe Glu Ser Ser Gly Ser Ile Ser Asn Leu
            260                 265                 270

Tyr Asn Met Ile Lys Ser Val Ala Ser Asp Cys Ser Asp Pro Thr Leu
        275                 280                 285

Leu Gly Asn Phe Ile Glu Asn His Asp Asn Pro Arg Phe Ala Ser Tyr
290                 295                 300

Thr Ser Asp Tyr Ser Gln Ala Lys Asn Val Leu Ser Tyr Ile Phe Leu
305                 310                 315                 320

Ser Asp Gly Ile Pro Ile Val Tyr Ala Gly Glu Glu Gln His Tyr Ser
                325                 330                 335

Gly Gly Asp Val Pro Tyr Asn Arg Glu Ala Thr Trp Leu Ser Gly Tyr

```
                    340             345                 350
Asp Thr Ser Ala Glu Leu Tyr Thr Trp Ile Ala Thr Asn Ala Ile
355                 360                 365

Arg Lys Leu Ala Ile Ser Ala Asp Ser Asp Tyr Ile Thr Tyr Ala Asn
370                 375                 380

Asp Pro Ile Tyr Thr Asp Ser Asn Thr Ile Ala Met Arg Lys Gly Thr
385                 390                 395                 400

Ser Gly Ser Gln Ile Ile Thr Val Leu Ser Asn Lys Gly Ser Ser Gly
405                 410                 415

Ser Ser Tyr Thr Leu Thr Leu Ser Gly Ser Gly Tyr Thr Ser Gly Thr
420                 425                 430

Lys Leu Ile Glu Ala Tyr Thr Cys Thr Ser Val Thr Val Asp Ser Asn
435                 440                 445

Gly Asp Ile Pro Val Pro Met Ala Ser Gly Leu Pro Arg Val Leu Leu
450                 455                 460

Pro Ala Ser Val Val Asp Ser Ser Leu Cys Gly Gly Ser Gly Asn
465                 470                 475                 480

Thr Thr Thr Thr Thr Thr Ala Ala Thr Ser Thr Ser Lys Ala Thr Thr
485                 490                 495

Ser Ser Ser Ser Ser Ala Ala Ala Thr Thr Ser Ser Cys Thr
500                 505                 510

Ala Thr Ser Thr Thr Leu Pro Ile Thr Phe Glu Glu Leu Val Thr Thr
515                 520                 525

Thr Tyr Gly Glu Glu Val Tyr Leu Ser Gly Ser Ile Ser Gln Leu Gly
530                 535                 540

Glu Trp Asp Thr Ser Asp Ala Val Lys Leu Ser Ala Asp Asp Tyr Thr
545                 550                 555                 560

Ser Ser Asn Pro Glu Trp Ser Val Thr Val Ser Leu Pro Val Gly Thr
565                 570                 575

Thr Phe Glu Tyr Lys Phe Ile Lys Val Asp Glu Gly Gly Ser Val Thr
580                 585                 590

Trp Glu Ser Asp Pro Asn Arg Glu Tyr Thr Val Pro Glu Cys Gly Ser
595                 600                 605

Gly Ser Gly Glu Thr Val Val Asp Thr Trp Arg
610                 615

<210> SEQ ID NO 4
<211> LENGTH: 640
<212> TYPE: PRT
<213> ORGANISM: Aspergillus kawachi

<400> SEQUENCE: 4

Met Arg Val Ser Thr Ser Ser Ile Ala Leu Ala Val Ser Leu Phe Gly
1               5                   10                  15

Lys Leu Ala Leu Gly Leu Ser Ala Ala Glu Trp Arg Thr Gln Ser Ile
20                  25                  30

Tyr Phe Leu Leu Thr Asp Arg Phe Gly Arg Thr Asp Asn Ser Thr Thr
35                  40                  45

Ala Thr Cys Asn Thr Gly Asp Gln Ile Tyr Cys Gly Gly Ser Trp Gln
50                  55                  60

Gly Ile Ile Asn His Leu Asp Tyr Ile Gln Gly Met Gly Phe Thr Ala
65                  70                  75                  80

Ile Trp Ile Ser Pro Ile Thr Glu Gln Leu Pro Gln Asp Thr Ser Asp
85                  90                  95
```

```
Gly Glu Ala Tyr His Gly Tyr Trp Gln Gln Lys Ile Tyr Asn Val Asn
100                 105                 110
Ser Asn Phe Gly Thr Ala Asp Asp Leu Lys Ser Leu Ser Asp Ala Leu
115                 120                 125
His Ala Arg Gly Met Tyr Leu Met Val Asp Val Pro Asn His Met
130                 135                 140
Gly Tyr Ala Gly Asn Gly Asn Asp Val Asp Tyr Ser Val Phe Asp Pro
145                 150                 155                 160
Phe Asp Ser Ser Tyr Phe His Pro Tyr Cys Leu Ile Thr Asp Trp
165                 170                 175
Asp Asn Leu Thr Met Val Gln Asp Cys Trp Glu Gly Asp Thr Ile Val
180                 185                 190
Ser Leu Pro Asp Leu Asn Thr Thr Glu Thr Ala Val Arg Thr Ile Trp
195                 200                 205
Tyr Asp Trp Val Ala Asp Leu Val Ser Asn Tyr Ser Val Asp Gly Leu
210                 215                 220
Arg Ile Asp Ser Val Glu Glu Val Glu Pro Asp Phe Phe Pro Gly Tyr
225                 230                 235                 240
Gln Glu Ala Ala Gly Val Tyr Cys Val Gly Glu Val Asp Asn Gly Asn
245                 250                 255
Pro Ala Leu Asp Cys Pro Tyr Gln Lys Tyr Leu Asp Gly Val Leu Asn
260                 265                 270
Tyr Pro Ile Tyr Trp Gln Leu Leu Tyr Ala Phe Glu Ser Ser Ser Gly
275                 280                 285
Ser Ile Ser Asn Leu Tyr Asn Met Ile Lys Ser Val Ala Ser Asp Cys
290                 295                 300
Ser Asp Pro Thr Leu Leu Gly Asn Phe Ile Glu Asn His Asp Asn Pro
305                 310                 315                 320
Arg Phe Ala Ser Tyr Thr Ser Asp Tyr Ser Gln Ala Lys Asn Val Leu
325                 330                 335
Ser Tyr Ile Phe Leu Ser Asp Gly Ile Pro Ile Val Tyr Ala Gly Glu
340                 345                 350
Glu Gln His Tyr Ser Gly Gly Asp Val Pro Tyr Asn Arg Glu Ala Thr
355                 360                 365
Trp Leu Ser Gly Tyr Asp Thr Ser Ala Glu Leu Tyr Thr Trp Ile Ala
370                 375                 380
Thr Thr Asn Ala Ile Arg Lys Leu Ala Ile Ser Ala Asp Ser Asp Tyr
385                 390                 395                 400
Ile Thr Tyr Ala Asn Asp Pro Ile Tyr Thr Asp Ser Asn Thr Ile Ala
405                 410                 415
Met Arg Lys Gly Thr Ser Gly Ser Gln Ile Ile Thr Val Leu Ser Asn
420                 425                 430
Lys Gly Ser Ser Gly Ser Ser Tyr Thr Leu Thr Leu Ser Gly Ser Gly
435                 440                 445
Tyr Thr Ser Gly Thr Lys Leu Ile Glu Ala Tyr Thr Cys Thr Ser Val
450                 455                 460
Thr Val Asp Ser Asn Gly Asp Ile Pro Val Pro Met Ala Ser Gly Leu
465                 470                 475                 480
Pro Arg Val Leu Leu Pro Ala Ser Val Val Asp Ser Ser Ser Leu Cys
485                 490                 495
Gly Gly Ser Gly Asn Thr Thr Thr Thr Thr Ala Ala Thr Ser Thr
500                 505                 510
Ser Lys Ala Thr Thr Ser Ser Ser Ser Ser Ser Ala Ala Ala Thr Thr
```

```
                515                 520                 525
Ser Ser Ser Cys Thr Ala Thr Ser Thr Thr Leu Pro Ile Thr Phe Glu
530                 535                 540

Glu Leu Val Thr Thr Thr Tyr Gly Glu Glu Val Tyr Leu Ser Gly Ser
545                 550                 555                 560

Ile Ser Gln Leu Gly Glu Trp Asp Thr Ser Asp Ala Val Lys Leu Ser
565                 570                 575

Ala Asp Asp Tyr Thr Ser Ser Asn Pro Glu Trp Ser Val Thr Val Ser
580                 585                 590

Leu Pro Val Gly Thr Thr Phe Glu Tyr Lys Phe Ile Lys Val Asp Glu
595                 600                 605

Gly Gly Ser Val Thr Trp Glu Ser Asp Pro Asn Arg Glu Tyr Thr Val
610                 615                 620

Pro Glu Cys Gly Ser Gly Ser Gly Glu Thr Val Val Asp Thr Trp Arg
625                 630                 635                 640

<210> SEQ ID NO 5
<211> LENGTH: 10990
<212> TYPE: DNA
<213> ORGANISM: Artificial Sequence
<220> FEATURE:
<223> OTHER INFORMATION: pTrex3g-Akalpha plasmid

<400> SEQUENCE: 5
ctgcagccac ttgcagtccc gtggaattct cacggtgaat gtaggccttt tgtagggtag    60
gaattgtcac tcaagcaccc ccaacctcca ttacgcctcc cccatagagt tcccaatcag   120
tgagtcatgg cactgttctc aaatagattg gggagaagtt gacttccgcc cagagctgaa   180
ggtcgcacaa ccgcatgata tagggtcggc aacggcaaaa aagcacgtgg ctcaccgaaa   240
agcaagatgt tgcgatcta acatccagga acctggatac atccatcatc acgcacgacc   300
actttgatct gctggtaaac tcgtattcgc cctaaaccga agtgcgtggt aaatctacac   360
gtgggcccct ttcggtatac tgcgtgtgtc ttctctaggt gccattcttt tcccttcctc   420
tagtgttgaa ttgtttgtgt tggagtccga gctgtaacta cctctgaatc tctggagaat   480
ggtggactaa cgactaccgt gcacctgcat catgtatata atagtgatcc tgagaagggg   540
ggtttggagc aatgtgggac tttgatggtc atcaaacaaa gaacgaagac gcctcttttg   600
caaagttttg tttcggctac ggtgaagaac tggatacttg ttgtgtcttc tgtgtatttt   660
tgtggcaaca agaggccaga gacaatctat tcaaacacca agcttgctct tttgagctac   720
aagaacctgt ggggtatata tctagagttg tgaagtcggt aatcccgctg tatagtaata   780
cgagtcgcat ctaaatactc cgaagctgct gcgaacccgg agaatcgaga tgtgctggaa   840
agcttctagc gagcggctaa attagcatga aaggctatga gaattctgga gacggcttg    900 ttgaatcatg gcgttccatt cttcgacaag caaagcgttc cgtcgcagta gcaggcactc    960
attcccgaaa aaactcggag attcctaagt agcgatggaa ccggaataat ataataggca   1020
atacattgag ttgcctcgac ggttgcaatg caggggtact gagcttggac ataactgttc   1080
cgtaccccac ctcttctcaa cctttggcgt ttccctgatt cagcgtaccc gtacaagtcg   1140
taatcactat taacccagac tgaccggacg tgttttgccc ttcatttgga gaataatgt    1200 cattgcgatg tgtaatttgc ctgcttgacc gactgggggct gttcgaagcc cgaatgtagg   1260
attgttatcc gaactctgct cgtagaggca tgttgtgaat ctgtgtcggg caggacacgc   1320
ctcgaaggtt cacggcaagg gaaaccaccg atagcagtgt ctagtagcaa cctgtaaagc   1380
```

```
cgcaatgcag catcactgga aaatacaaac caatggctaa aagtacataa gttaatgcct      1440
aaagaagtca tataccagcg gctaataatt gtacaatcaa gtggctaaac gtaccgtaat      1500
ttgccaacgg cttgtggggt tgcagaagca acggcaaagc cccacttccc cacgtttgtt      1560
tcttcactca gtccaatctc agctggtgat cccccaattg ggtcgcttgt ttgttccggt      1620
gaagtgaaag aagacagagg taagaatgtc tgactcggag cgttttgcat acaaccaagg      1680
gcagtgatgg aagacagtga atgttgaca ttcaaggagt atttagccag ggatgcttga       1740
gtgtatcgtg taaggaggtt tgtctgccga tacgacgaat actgtatagt cacttctgat      1800
gaagtggtcc atattgaaat gtaagtcggc actgaacagg caaaagattg agttgaaact      1860
gcctaagatc tcgggccctc gggccttcgg cctttgggtg tacatgtttg tgctccgggc      1920
aaatgcaaag tgtggtagga tcgaacacac tgctgccttt accaagcagc tgagggtatg      1980
tgataggcaa atgttcaggg gccactgcat ggtttcgaat agaaagagaa gcttagccaa      2040
gaacaatagc cgataaagat agcctcatta aacggaatga gctagtaggc aaagtcagcg      2100
aatgtgtata tataaaggtt cgaggtccgt gcctccctca tgctctcccc atctactcat      2160
caactcagat cctccaggag acttgtacac catcttttga ggcacagaaa cccaatagtc      2220
aaccatcaca agtttgtaca aaaaagcagg ctccgcggcc gcccccttca ccatgagagt      2280
gtcgacttca agtattgccc ttgctgtgtc ccttttgggg aagctggccc ttgggctgtc      2340
agctgcagaa tggcgcactc aatccatcta cttccttttg acggatcggt tcggtaggac      2400
ggacaattcg actacagcta cgtgcaatac gggtgaccaa gtatggtatt gctgtacttc      2460
cgtcattcat ctgctgactt ggatagatct actgtggtgg aagttggcaa ggaattatca      2520
accatgttcg tatctcactt cataccatcc atgctgggcg cttctgacta ttgctccagc      2580
tggactatat ccagggcatg ggattcacag ctatctggat ctcgcctatc actgagcagc      2640
taccccagga tacttcggat ggtgaagcct accatggata ctggcagcag aagatgtatg      2700
ccctcattgc attcatattt tatgcttact cgcagactgc agctgacttg gcagatacaa      2760
tgtgaactcc aacttcggca cggcagatga tctgaagtcc ctctccgatg ctcttcacgc      2820
ccgcggaatg tacctcatgg tcgacgtcgt ccctaaccac atggtaagta ctgctttacc      2880
tctatattag taaacccaat gcgaacaatg actgtatcag ggctacgcag gtaacggcaa      2940
cgatgtggat tacagcgtct tcgacccctt cgactcctcc tcctacttcc atccatactg      3000
cctcatcaca gattgggaca acttgaccat ggtccaagac tgttgggagg gtgacaccat      3060
cgtgtctctg ccagatctga acaccacgga aaccgccgtg agaaccatttt ggtacgattg      3120 ggtagccgac ctggtatcca actactcagg tgcgacccca acccactaaa acaagccaca      3180
tactaaaaaa ttgctcagtc gacggcctcc gtatcgacag tgtcgaagaa gtcgaacccg      3240
acttcttccc gggctaccaa gaagcagcag gagtctactg cgtcggtgaa gtcgacaacg      3300
gcaaccctgc tctcgactgc ccataccaaa aatatctaga tggtgttctc aactatccca      3360
tgtacatacc cccttctacc ttctcgaacc catcactaac tcaattgctg cagctactgg      3420
caactcctct acgcctttga atcctccagc ggcagcatca gcaacctcta caacatgatc      3480
aaatccgtcg ccagcgactg ctccgatccg accctcctgg gcaactttat cgaaaaccac      3540
gacaaccccc gcttcgcctc gtatgtccct tccatcactg cccccttta aagtaaaccc       3600 cactgacagg caaagctaca catccgacta ctcccaagcc aaaaacgtcc tcagctacat      3660
cttcctctcc gacggcatcc ccatcgtcta cgcggcgaa gaacagcact actccggcgg       3720
cgacgtgccc tacaaccgcg aagctacctg gctatcaggc tacgacacct ccgcggagct      3780
```

```
ctacacctgg atagccacca caaacgcgat ccggaaacta gctatctcag cagactcgga    3840
ctacattact tacgcggttt gcccttcccc ttcccccccac ccagagctca accccccattc   3900
taacaaaata tttcaatggt agaacgaccc aatctacaca gacagcaaca ccatcgcgat    3960
gcgcaaaggc acctccggct cccaaatcat caccgtcctc tccaacaaag gctcctccgg    4020
aagcagctac accctcaccc tcagcggaag cggctacacg tccggcacga agctcatcga    4080
agcgtacacc tgcacgtccg tgacggtgga ctcgaacggg gatatccctg tgccgatggc    4140
ttcgggatta cctagagttc tcctccctgc ttcggtggtt gatagttctt cgctttgtgg    4200
ggggagtggt aacacaacca cgaccacaac tgctgctacc tccacatcca aagccaccac    4260
ctcctcttct tcttcttctg ctgctgctac tacttcttca tcatgcaccg caacaagcac    4320
caccctcccc atcaccttcg aagaactcgt caccactacc tacggggaag aagtctacct    4380
cagcggatct atctcccagc tcggagagtg ggatacgagt gacgcggtga agttgtccgc    4440
ggatgattat acctcgagta accccgagtg gtctgttact gtgtcgttgc cggtggggac    4500
gaccttcgag tataagttta ttaaggtcga tgagggtgga agtgtgactt gggaaagtga    4560
tccgaatagg gagtatactg tgcctgaatg tgggagtggg agtggggaga cggtggttga    4620
tacgtggagg tagaagggtg ggcgcgccga cccagctttc ttgtacaaag tggtgatcgc    4680
gccagctccg tgcgaaagcc tgacgcaccg gtagattctt ggtgagcccg tatcatgacg    4740
gcggcgggag ctacatggcc ccgggtgatt tattttttt gtatctactt ctgacccttt     4800
tcaaatatac ggtcaactca tcttcactg gagatgcggc ctgcttggta ttgcgatgtt     4860
gtcagcttgg caaattgtgg ctttcgaaaa cacaaaacga ttccttagta gccatgcatt    4920
ttaagataac ggaatagaag aaagaggaaa ttaaaaaaaa aaaaaaaaca aacatcccgt    4980
tcataacccg tagaatcgcc gctcttcgtg tatcccagta ccagtttatt ttgaatagct    5040
cgcccgctgg agagcatcct gaatgcaagt aacaaccgta gaggctgaca cggcaggtgt    5100
tgctagggag cgtcgtgttc tacaaggcca gacgtcttcg cggttgatat atatgtatgt    5160
ttgactgcag gctgctcagc gacgacagtc aagttcgccc tcgctgcttg tgcaataatc    5220
gcagtgggga agccacaccg tgactcccat ctttcagtaa agctctgttg gtgtttatca    5280
gcaatacacg taatttaaac tcgttagcat ggggctgata gcttaattac cgtttaccag    5340
tgccatggtt ctgcagcttt ccttggcccg taaaattcgg cgaagccagc caatcaccag    5400
ctaggcacca gctaaaccct ataattagtc tcttatcaac accatccgct cccccgggat    5460
caatgaggag aatgagggg atgcggggct aaagaagcct acataaccct catgccaact    5520
cccagtttac actcgtcgag ccaacatcct gactataagc taacacagaa tgcctcaatc    5580
ctgggaagaa ctggccgctg ataagcgcgc ccgcctcgca aaaccatcc ctgatgaatg     5640
gaaagtccag acgctgcctg cggaagacag cgttattgat ttcccaaaga atcggggat    5700
cctttcagag gccgaactga agatcacaga ggcctccgct gcagatcttg tgtccaagct    5760
ggcggccgga gagttgacct cggtggaagt tacgctagca ttctgtaaac gggcagcaat    5820
cgcccagcag ttagtagggt cccctctacc tctcagggag atgtaacaac gccaccttat    5880
gggactatca agctgacgct ggcttctgtg cagacaaact cgcgccacga gttcttccct    5940
gacgccgctc tcgcgcaggc aagggaactc gatgaatact acgcaaagca caagagaccc    6000
gttggtccac tccatggcct ccccatctct ctcaaagacc agcttcgagt caaggtacac    6060
cgttgcccct aagtcgttag atgtcccttt ttgtcagcta acatatgcca ccagggctac    6120
```

```
gaaacatcaa tgggctacat ctcatggcta acaagtacg acgaagggga ctcggttctg    6180
acaaccatgc tccgcaaagc cggtgccgtc ttctacgtca agacctctgt cccgcagacc    6240
ctgatggtct gcgagacagt caacaacatc atcgggcgca ccgtcaaccc acgcaacaag    6300
aactggtcgt gcggcggcag ttctggtggt gagggtgcga tcgttgggat tcgtggtggc    6360
gtcatcggtg taggaacgga tatcggtggc tcgattcgag tgccggccgc gttcaacttc    6420
ctgtacggtc taaggccgag tcatgggcgg ctgccgtatg caaagatggc gaacagcatg    6480
gagggtcagg agacggtgca cagcgttgtc gggccgatta cgcactctgt tgagggtgag    6540
tccttcgcct cttccttctt ttcctgctct ataccaggcc tccactgtcc tcctttcttg    6600
cttttttatac tatatacgag accggcagtc actgatgaag tatgttagac ctccgcctct    6660
tcaccaaatc cgtcctcggt caggagccat ggaaatacga ctccaaggtc atccccatgc    6720
cctggcgcca gtccgagtcg gacattattg cctccaagat caagaacggc gggctcaata    6780
tcggctacta caacttcgac ggcaatgtcc ttccacaccc tcctatcctg cgcggcgtgg    6840
aaaccaccgt cgccgcactc gccaaagccg gtcacaccgt gaccccgtgg acgccataca    6900
agcacgattt cggccacgat ctcatctccc atatctacgc ggctgacggc agcgccgacg    6960
taatgcgcga tatcagtgca tccggcgagc cggcgattcc aaatatcaaa gacctactga    7020
acccgaacat caaagctgtt aacatgaacg agctctggga cacgcatctc cagaagtgga    7080
attaccagat ggagtacctt gagaaatggc gggaggctga agaaaaggcc gggaaggaac    7140
tggacgccat catcgcgccg attacgccta ccgctgcggt acggcatgac cagttccggt    7200
actatgggta tgcctctgtg atcaacctgc tggatttcac gagcgtggtt gttccggtta    7260
cctttgcgga taagaacatc gataagaaga atgagagttt caaggcggtt agtgagcttg    7320
atgccctcgt gcaggaagag tatgatccgg aggcgtacca tggggcaccg gttgcagtgc    7380
aggttatcgg acggagactc agtgaagaga ggacgttggc gattgcagag gaagtgggga    7440
agttgctggg aaatgtggtg actccatagc taataagtgt cagatagcaa tttgcacaag    7500
aaatcaatac cagcaactgt aaataagcgc tgaagtgacc atgccatgct acgaaagagc    7560
agaaaaaaac ctgccgtaga accgaagaga tatgacacgc ttccatctct caaaggaaga    7620
atcccttcag ggttgcgttt ccagtctaga cacgtataac ggcacaagtg tctctcacca    7680
aatgggttat atctcaaatg tgatctaagg atggaaagcc cagaatatcg atcgcgcgca    7740
gatccatata tagggcccgg ttataatta cctcaggtcg acgtcccatg gccattcgaa    7800
ttcgtaatca tggtcatagc tgtttcctgt gtgaaattgt tatccgctca caattccaca    7860
caacatacga gccggaagca taaagtgtaa agcctggggt gcctaatgag tgagctaact    7920
cacattaatt gcgttgcgct cactgcccgc tttccagtcg ggaaacctgt cgtgccagct    7980
gcattaatga atcggccaac gcgcggggag aggcggtttg cgtattgggc gctcttccgc    8040
ttcctcgctc actgactcgc tgcgctcggt cgttcggctg cggcgagcgg tatcagctca    8100
ctcaaaggcg gtaatacggt tatccacaga atcagggat aacgcaggaa agaacatgtg    8160
agcaaaaggc cagcaaaagg ccaggaaccg taaaaaggcc gcgttgctgg cgttttccca    8220
taggctccgc cccctgacg agcatcacaa aaatcgacgc tcaagtcaga ggtggcgaaa    8280
cccgacagga ctataaagat accaggcgtt tccccctgga agctccctcg tgcgctctcc    8340
tgttccgacc ctgccgctta ccggatacct gtccgccttt ctcccttcgg gaagcgtggc    8400
gctttctcat agctcacgct gtaggtatct cagttcggtg taggtcgttc gctccaagct    8460
gggctgtgtg cacgaacccc ccgttcagcc cgaccgctgc gccttatccg gtaactatcg    8520
```

```
tcttgagtcc aacccggtaa gacacgactt atcgccactg gcagcagcca ctggtaacag   8580
gattagcaga gcgaggtatg taggcggtgc tacagagttc ttgaagtggt ggcctaacta   8640
cggctacact agaagaacag tatttggtat ctgcgctctg ctgaagccag ttaccttcgg   8700
aaaaagagtt ggtagctctt gatccggcaa acaaaccacc gctggtagcg gtggtttttt   8760
tgtttgcaag cagcagatta cgcgcagaaa aaaggatct caagaagatc ctttgatctt   8820
ttctacgggg tctgacgctc agtggaacga aaactcacgt taagggattt tggtcatgag   8880
attatcaaaa aggatcttca cctagatcct tttaaattaa aaatgaagtt ttaaatcaat   8940
ctaaagtata tatgagtaaa cttggtctga cagttaccaa tgcttaatca gtgaggcacc   9000
tatctcagcg atctgtctat ttcgttcatc catagttgcc tgactccccg tcgtgtagat   9060
aactacgata cgggagggct taccatctgg ccccagtgct gcaatgatac cgcgagaccc   9120
acgctcaccg gctccagatt tatcagcaat aaaccagcca gccggaaggg ccgagcgcag   9180
aagtggtcct gcaactttat ccgcctccat ccagtctatt aattgttgcc gggaagctag   9240
agtaagtagt tcgccagtta atagtttgcg caacgttgtt gccattgcta caggcatcgt   9300
ggtgtcacgc tcgtcgtttg gtatggcttc attcagctcc ggttcccaac gatcaaggcg   9360
agttacatga tcccccatgt tgtgcaaaaa agcggttagc tccttcggtc ctccgatcgt   9420
tgtcagaagt aagttggccg cagtgttatc actcatggtt atggcagcac tgcataattc   9480
tcttactgtc atgccatccg taagatgctt ttctgtgact ggtgagtact caaccaagtc   9540
attctgagaa tagtgtatgc ggcgaccgag ttgctcttgc ccggcgtcaa tacgggataa   9600
taccgcgcca catagcagaa ctttaaaagt gctcatcatt ggaaaacgtt cttcggggcg   9660
aaaactctca aggatcttac cgctgttgag atccagttcg atgtaaccca ctcgtgcacc   9720
caactgatct tcagcatctt ttactttcac cagcgtttct gggtgagcaa aaacaggaag   9780
gcaaaatgcc gcaaaaaagg gaataagggc gacacggaaa tgttgaatac tcatactctt   9840
cctttttcaa tattattgaa gcatttatca gggttattgt ctcatgagcg gatacatatt   9900
tgaatgtatt tagaaaaata aacaaatagg ggttccgcgc acatttcccc gaaaagtgcc   9960
acctgacgtc taagaaacca ttattatcat gacattaacc tataaaaata ggcgtatcac  10020
gaggcccttt cgtctcgcgc gtttcggtga tgacggtgaa aacctctgac acatgcagct  10080
cccggagacg gtcacagctt gtctgtaagc ggatgccggg agcagacaag cccgtcaggg  10140
cgcgtcagcg ggtgttggcg ggtgtcgggg ctggcttaac tatgcggcat cagagcagat  10200
tgtactgaga gtgcaccata aaattgtaaa cgttaatatt ttgttaaaat tcgcgttaaa  10260 ttttttgttaa atcagctcat tttttaacca taggccgaa atcggcaaaa tcccttataa  10320
atcaaaagaa tagcccgaga tagggttgag tgttgttcca gtttggaaca agagtccact  10380
attaaagaac gtggactcca acgtcaaagg gcgaaaaacc gtctatcagg gcgatggccc  10440
actacgtgaa ccatcaccca atcaagtttt ttggggtcg aggtgccgta aagcactaaa  10500
tcggaaccct aaagggagcc ccgatttag agcttgacgg ggaaagccgg cgaacgtggc  10560
gagaaaggaa gggaagaaag cgaaaggagc gggcgctagg gcgctggcaa gtgtagcggt  10620
cacgctgcgc gtaaccacca cacccgccgc gcttaatgcg ccgctacagg gcgcgtacta  10680
tggttgcttt gacgtatgcg gtgtgaaata ccgcacagat gcgtaaggag aaaataccgc  10740
atcaggcgcc attcgccatt caggctgcgc aactgttggg aagggcgatc ggtgcgggcc  10800
tcttcgctat tacgccagct ggcgaaaggg ggatgtgctg caaggcgatt aagttgggta  10860
```

-continued

```
acgccagggt tttcccagtc acgacgttgt aaaacgacgg ccagtgccca agcttactag    10920
tacttctcga gctctgtaca tgtccggtcg cgacgtacgc gtatcgatgg cgccagctgc    10980
aggcggccgc                                                          10990
```

<210> SEQ ID NO 6
<211> LENGTH: 24
<212> TYPE: DNA
<213> ORGANISM: Artificial Sequence
<220> FEATURE:
<223> OTHER INFORMATION: primer

<400> SEQUENCE: 6

```
caccatgaga gtgtcgactt caag                                          24
```

<210> SEQ ID NO 7
<211> LENGTH: 21
<212> TYPE: DNA
<213> ORGANISM: Artificial Sequence
<220> FEATURE:
<223> OTHER INFORMATION: primer

<400> SEQUENCE: 7

```
ctacctccac gtatcaacca c                                             21
```

<210> SEQ ID NO 8
<211> LENGTH: 37
<212> TYPE: PRT
<213> ORGANISM: Aspergillus kawachi

<400> SEQUENCE: 8

```
Thr Thr Thr Thr Thr Thr Ala Ala Thr Ser Thr Ser Lys Ala Thr Thr
1               5                   10                  15

Ser Ser Ser Ser Ser Ser Ala Ala Ala Thr Thr Ser Ser Ser Cys Thr
            20                  25                  30

Ala Thr Ser Thr Thr
        35
```

<210> SEQ ID NO 9
<211> LENGTH: 480
<212> TYPE: PRT
<213> ORGANISM: Aspergillus kawachi

<400> SEQUENCE: 9

```
Leu Ser Ala Ala Glu Trp Arg Thr Gln Ser Ile Tyr Phe Leu Leu Thr
1               5                   10                  15

Asp Arg Phe Gly Arg Thr Asp Asn Ser Thr Thr Ala Thr Cys Asn Thr
            20                  25                  30

Gly Asp Gln Ile Tyr Cys Gly Gly Ser Trp Gln Gly Ile Ile Asn His
        35                  40                  45

Leu Asp Tyr Ile Gln Gly Met Gly Phe Thr Ala Ile Trp Ile Ser Pro
    50                  55                  60

Ile Thr Glu Gln Leu Pro Gln Asp Thr Ser Asp Gly Glu Ala Tyr His
65                  70                  75                  80

Gly Tyr Trp Gln Gln Lys Ile Tyr Asn Val Asn Ser Asn Phe Gly Thr
                85                  90                  95

Ala Asp Asp Leu Lys Ser Leu Ser Asp Ala Leu His Ala Arg Gly Met
            100                 105                 110

Tyr Leu Met Val Asp Val Val Pro Asn His Met Gly Tyr Ala Gly Asn
        115                 120                 125
```

```
Gly Asn Asp Val Asp Tyr Ser Val Phe Asp Pro Phe Asp Ser Ser Ser
130                 135                 140

Tyr Phe His Pro Tyr Cys Leu Ile Thr Asp Trp Asp Asn Leu Thr Met
145                 150                 155                 160

Val Gln Asp Cys Trp Glu Gly Asp Thr Ile Val Ser Leu Pro Asp Leu
165                 170                 175

Asn Thr Thr Glu Thr Ala Val Arg Thr Ile Trp Tyr Asp Trp Val Ala
180                 185                 190

Asp Leu Val Ser Asn Tyr Ser Val Asp Gly Leu Arg Ile Asp Ser Val
195                 200                 205

Glu Glu Val Glu Pro Asp Phe Phe Pro Gly Tyr Gln Glu Ala Ala Gly
210                 215                 220

Val Tyr Cys Val Gly Glu Val Asp Asn Gly Asn Pro Ala Leu Asp Cys
225                 230                 235                 240

Pro Tyr Gln Lys Tyr Leu Asp Gly Val Leu Asn Tyr Pro Ile Tyr Trp
245                 250                 255

Gln Leu Leu Tyr Ala Phe Glu Ser Ser Ser Gly Ser Ile Ser Asn Leu
260                 265                 270

Tyr Asn Met Ile Lys Ser Val Ala Ser Asp Cys Ser Asp Pro Thr Leu
275                 280                 285

Leu Gly Asn Phe Ile Glu Asn His Asp Asn Pro Arg Phe Ala Ser Tyr
290                 295                 300

Thr Ser Asp Tyr Ser Gln Ala Lys Asn Val Leu Ser Tyr Ile Phe Leu
305                 310                 315                 320

Ser Asp Gly Ile Pro Ile Val Tyr Ala Gly Glu Glu Gln His Tyr Ser
325                 330                 335

Gly Gly Asp Val Pro Tyr Asn Arg Glu Ala Thr Trp Leu Ser Gly Tyr
340                 345                 350

Asp Thr Ser Ala Glu Leu Tyr Thr Trp Ile Ala Thr Thr Asn Ala Ile
355                 360                 365

Arg Lys Leu Ala Ile Ser Ala Asp Ser Asp Tyr Ile Thr Tyr Ala Asn
370                 375                 380

Asp Pro Ile Tyr Thr Asp Ser Asn Thr Ile Ala Met Arg Lys Gly Thr
385                 390                 395                 400

Ser Gly Ser Gln Ile Ile Thr Val Leu Ser Asn Lys Gly Ser Ser Gly
405                 410                 415

Ser Ser Tyr Thr Leu Thr Leu Ser Gly Ser Gly Tyr Thr Ser Gly Thr
420                 425                 430

Lys Leu Ile Glu Ala Tyr Thr Cys Thr Ser Val Thr Val Asp Ser Asn
435                 440                 445

Gly Asp Ile Pro Val Pro Met Ala Ser Gly Leu Pro Arg Val Leu Leu
450                 455                 460

Pro Ala Ser Val Val Asp Ser Ser Ser Leu Cys Gly Gly Ser Gly Asn
465                 470                 475                 480

<210> SEQ ID NO 10
<211> LENGTH: 102
<212> TYPE: PRT
<213> ORGANISM: Aspergillus kawachi

<400> SEQUENCE: 10

Leu Pro Ile Thr Phe Glu Glu Leu Val Thr Thr Tyr Gly Glu Glu
1               5                   10                  15

Val Tyr Leu Ser Gly Ser Ile Ser Gln Leu Gly Glu Trp Asp Thr Ser
20                  25                  30
```

```
Asp Ala Val Lys Leu Ser Ala Asp Asp Tyr Thr Ser Ser Asn Pro Glu
 35                  40                  45

Trp Ser Val Thr Val Ser Leu Pro Val Gly Thr Thr Phe Glu Tyr Lys
 50                  55                  60

Phe Ile Lys Val Asp Glu Gly Gly Ser Val Thr Trp Glu Ser Asp Pro
 65                  70                  75                  80

Asn Arg Glu Tyr Thr Val Pro Glu Cys Gly Ser Gly Ser Gly Glu Thr
 85                  90                  95

Val Val Asp Thr Trp Arg
100

<210> SEQ ID NO 11
<211> LENGTH: 29
<212> TYPE: DNA
<213> ORGANISM: Artificial Sequence
<220> FEATURE:
<223> OTHER INFORMATION: primer

<400> SEQUENCE: 11
gcgcgctacg taatgagagt gtcgacttc                                      29

<210> SEQ ID NO 12
<211> LENGTH: 27
<212> TYPE: DNA
<213> ORGANISM: Artificial Sequence
<220> FEATURE:
<223> OTHER INFORMATION: primer

<400> SEQUENCE: 12
gcgcgctacg tactacctcc acgtatc                                        27

<210> SEQ ID NO 13
<211> LENGTH: 28
<212> TYPE: DNA
<213> ORGANISM: Artificial Sequence
<220> FEATURE:
<223> OTHER INFORMATION: primer

<400> SEQUENCE: 13
gggcccattt tgaatagctc gcccgctg                                       28

<210> SEQ ID NO 14
<211> LENGTH: 30
<212> TYPE: DNA
<213> ORGANISM: Artificial Sequence
<220> FEATURE:
<223> OTHER INFORMATION: primer

<400> SEQUENCE: 14
gggccccaat tgcctaatgc tatgtgcaag                                     30
```

HETEROLOGOUS ALPHA AMYLASE EXPRESSION IN *ASPERGILLUS*

The present application is a continuation of U.S. patent application Ser. No. 11/270,864, filed Nov. 8, 2005, now U.S. Pat. No. 7,332,319 which is a continuation-in-part application of U.S. patent application Ser. No. 11/136,244 filed May 24, 2005, now U.S. Pat. No. 7,354,752 which claims priority to U.S. Provisional Patent Application Ser. No. 60/575,175, filed May 27, 2004, expired; U.S. Provisional Patent Application Ser. No. 60/605,437, filed Aug. 30, 2004, expired; International Application No. PCT/US04/040040, filed Nov. 30, 2004; International Application No. PCT/US04/041276, filed Dec. 9, 2004; and U.S. Provisional Patent Application Ser. No. 60/647,925 filed Jan. 28, 2005, and is a continuation-in-part application of U.S. patent application Ser. No. 10/999,886, filed Nov. 30, 2004, now U.S. Pat. No. 7,037,704 which claims priority to U.S. Provisional Application Ser. No. 60/605,437, filed Aug. 30, 2004, expired and U.S. Provisional Application Ser. No. 60/575,175, filed May 27, 2004, expired; the contents of all of the above are fully incorporated by reference herein.

FIELD OF THE INVENTION

The present invention relates to an alpha amylase, which is derived from a strain of *Aspergillus kawachi*. Further, the invention relates to the heterologous expression of an alpha amylase in filamentous fungal host cells, such as *Aspergillus* cells (e.g. *Aspergillus niger*) and to enzyme compositions comprising the alpha amylase.

BACKGROUND OF THE INVENTION

Glucoamylases, and including glucoamylases having granular starch hydrolyzing (GSH) activity are important industrial enzymes used for producing products such as organic acids (e.g. lactic acids), amino acids (e.g. glutamic acids), sugar sweetener products (e.g. glucose and high fructose corn syrup), alcohols (e.g. ethanol) and other compounds from starch substrates derived from grains and cereals. In addition, during microbial fermentations, and particularly during simultaneous saccharification and fermentation (SSF), it would be of benefit to reduce the amount of residual starch in the fermentation when granular starch substrates are used as a carbon feed. The present invention answers this need by providing an alpha amylase, such as an acid-stable alpha amylase (asAA) having granular starch hydrolyzing (GSH) activity, which may be used in combination with a glucoamylase to enhance starch hydrolysis and alcohol production.

Some benefits of the present invention over prior art compositions and methods include one or more of the following: a) reduction of thermal energy use during starch hydrolysis and/or end-product production; b) reduction in the requirement of high enzyme dosage; c) utilization of a continuous release of glucose from starch to feed yeast; d) maintenance of a relatively low glucose level in the fermenter, which may reduce the high risk of microbial contamination and which may remove the catabolite repression of yeast due to high concentration of free glucose; e) reduction in formation of browning reaction products; f) reduction or removal of calcium addition, which may be required during the prior art jet cooking process; g) reduction in water utilization during the fermentation process; h) use of higher solids content in the fermentation, which may result in higher end-product formation and reduced energy costs; i) reduced levels of production of certain by-products, such as glycerol; and/or j) decreased residual starch content and increased protein content of distillers dry grains plus solubles.

SUMMARY OF THE INVENTION

In one aspect, the invention relates to a fungal host cell comprising a heterologous polynucleotide that encodes an acid-stable alpha amylase (asAA) having granular starch hydrolyzing (GSH) activity, said alpha amylase having at least 90% sequence identity to the sequence of SEQ ID NO: 3. In some embodiments, the heterologous polynucleotide will encode an asAA having GSH activity with at least 95% sequence identity to the sequence of SEQ ID NO: 3. In some embodiments, the fungal host cell is a *Trichoderma* cell, such as a *T. reesei* cell. In other embodiments, the fungal host cell is an *Aspergillus* cell, such as an *A. niger*.

In a second aspect, the invention relates to an asAA having GSH activity comprising an amino acid sequence having at least 90% sequence identity with SEQ ID NO: 3. In some embodiments of this aspect, the asAA having GSH activity will be a truncated asAA. In some embodiments, the truncated asAA comprises a sequence of SEQ ID NO: 9 or a sequence having at least 97% sequence identity thereto.

In a third aspect, the invention relates to an enzyme composition which comprises an acid-stable alpha amylase (asAA) having granular starch hydrolyzing (GSH) activity, wherein the asAA has at least 90% sequence identity to the sequence of SEQ ID NO: 3. In some embodiments, the enzyme composition comprises a truncated asAA enzyme, said enzyme having at least 97% sequence identity with SEQ ID NO: 9. In some embodiments, the asAA will be obtained from the expression of a heterologous polynucleotide in a fungal host cell. In further embodiments, the fungal host cell will be a *Trichoderma* or *Aspergillus* host cell. In other embodiments, the composition will further include a glucoamylase enzyme. In some embodiments, the glucoamylase enzyme will be obtained from a strain of *Aspergillus* or *Rhizopus*. In other embodiments, the glucoamylase will be a glucoamylase having GSH activity and will be obtained from a strain of *Aspergillus, Trichoderma, Rhizopus* or *Humicola*. In other embodiments, both the asAA and the glucoamylase will be expressed in the same fungal host having a heterologous polynucleotide, which expresses an asAA having GSH activity and the glucoamylase. In other embodiments, the invention relates to a method of hydrolyzing starch, such as granular starch using the enzyme composition of this aspect.

In a fourth aspect, the invention relates to a recombinant *Aspergillus* strain comprising DNA encoding a glucoamylase and DNA encoding a heterologous alpha amylase, said alpha amylase having at least 90% sequence identity to SEQ ID NO: 3 or SEQ ID NO: 4, wherein both the glucoamylase and the heterologous alpha amylase are expressed and secreted by the *Aspergillus* strain.

In a fifth aspect, the invention relates to a method for producing an alpha amylase and a glucoamylase in a filamentous fungal host cell comprising transforming an *Aspergillus* host cell which produces a glucoamylase with a DNA construct including a promoter having transcriptional activity in the *Aspergillus* host cell operably linked to a polynucleotide encoding an alpha amylase having at least 85% sequence identity to SEQ ID NO: 3 or SEQ ID NO: 4, cultivating the transformed *Aspergillus* host cell in a suitable culture medium to allow expression of said alpha amylase and the glucoamylase, and producing the alpha amylase and glucoamylase. In one embodiment, the method further comprises recovering the produced alpha amylase and glucoamylase.

In a sixth aspect, the invention relates to a method of producing an alpha amylase in an *Aspergillus* cell which comprises, culturing an *Aspergillus* cell which is capable of expressing a heterologous alpha amylase polypeptide having at least 90% sequence identity to SEQ ID NO: 3 or SEQ ID NO: 4 under conditions suitable for the expression and production of the heterologous alpha amylase and producing the heterologous alpha amylase.

In a seventh aspect, the invention relates to a method for producing a heterologous acid stable alpha amylase and a glucoamylase in a filamentous fungal host cell comprising co-expressing a glucoamylase and an alpha amylase in a filamentous host by transforming the filamentous fungal cell with a DNA construct comprising a promoter having transcriptional activity in the host cell operably linked to a polynucleotide encoding an alpha amylase having at least 90% sequence identity to SEQ ID NO: 3, wherein said host cell further expresses and produces a glucoamylase, cultivating the transformed host cell in a suitable culture medium to allow expression of the alpha amylase and glucoamylase, and producing the alpha amylase and the glucoamylase.

In an eighth aspect, the invention relates to a method of hydrolyzing starch, such as granular starch which comprises contacting a substrate containing starch with an enzyme composition comprising the alpha amylase and glucoamylase produced according to the methods encompassed by the invention. In one embodiment contacting includes contacting the substrate with a culture medium that includes the *Aspergillus* cells producing the glucoamylase and alpha amylase. In another embodiment, contacting includes contacting the substrate with glucoamylase and alpha amylase which has been recovered from a culture of *Aspergillus* cells that produces the glucoamylase and alpha amylase. In further embodiments, the alpha amylase has at least 85% sequence identity to the sequence of SEQ ID NO: 3 or SEQ ID NO: 4.

BRIEF DESCRIPTION OF THE DRAWINGS

FIG. 1 provides the genomic DNA sequence coding for the native *Aspergillus kawachi* acid-stable alpha-amylase (SEQ ID NO: 1). The eight putative introns are underlined.

FIG. 2 illustrates the protein (SEQ ID NO: 4) coded for by the polynucleotide of FIG. 1. The putative signal sequence (amino acids 1-21) is underlined and bold (SEQ ID NO: 2). The putative linker is TTTTTTAATSTSKATTSSSSS-SAAATTSS SCTATSTT (SEQ ID NO: 8). The amino acids upstream of the linker, which are not underlined comprise the catalytic domain (SEQ ID NO: 9) and the amino acids downstream of the linker comprise the starch binding domain (SBD) (SEQ ID NO: 10). The SBD includes the last 102 amino acids of the polypeptide of FIG. 2. The mature protein lacks the signal sequence and is represented by the amino acid sequence of the catalytic domain, linker and SBD (SEQ ID NO: 3).

FIGS. 3A-D provides the complete nucleotide sequence (SEQ ID NO: 5), 10990 bp, of plasmid pTrex3g_Akalpha (FIG. 4).

FIGS. 6A and B provide an SDS-PAGE gel indicating the expression of asaA from *Trichoderma reesei* in a representative fermentation run for *Trichoderma reesei* clones as described in Example 5. In FIG. 6A, lane 1 represents the standard See Blue +2 marker; lane 2 represents *T. reesei* expressed AsaA after 80 hours; lane 3 represents *T. reesei* expressed AsaA after 162 hours and lane 4 represents a *T. reesei* host cell control at 162 hours in which the host cell has not been transformed with the asaA. An AsaA protein band is clearly observed at about 90 kDa and this band is absent in the host strain control. In FIG. 6B, lane 1 represents intact *T. reesei* expressed AsaA after 210 hrs, lane 2 represents three bands of *T. reesei* expressed AsaA in intact and truncated form after 200 hours and lane 3 represents a molecular weight marker control.

DETAILED DESCRIPTION OF THE INVENTION

Figure 4:
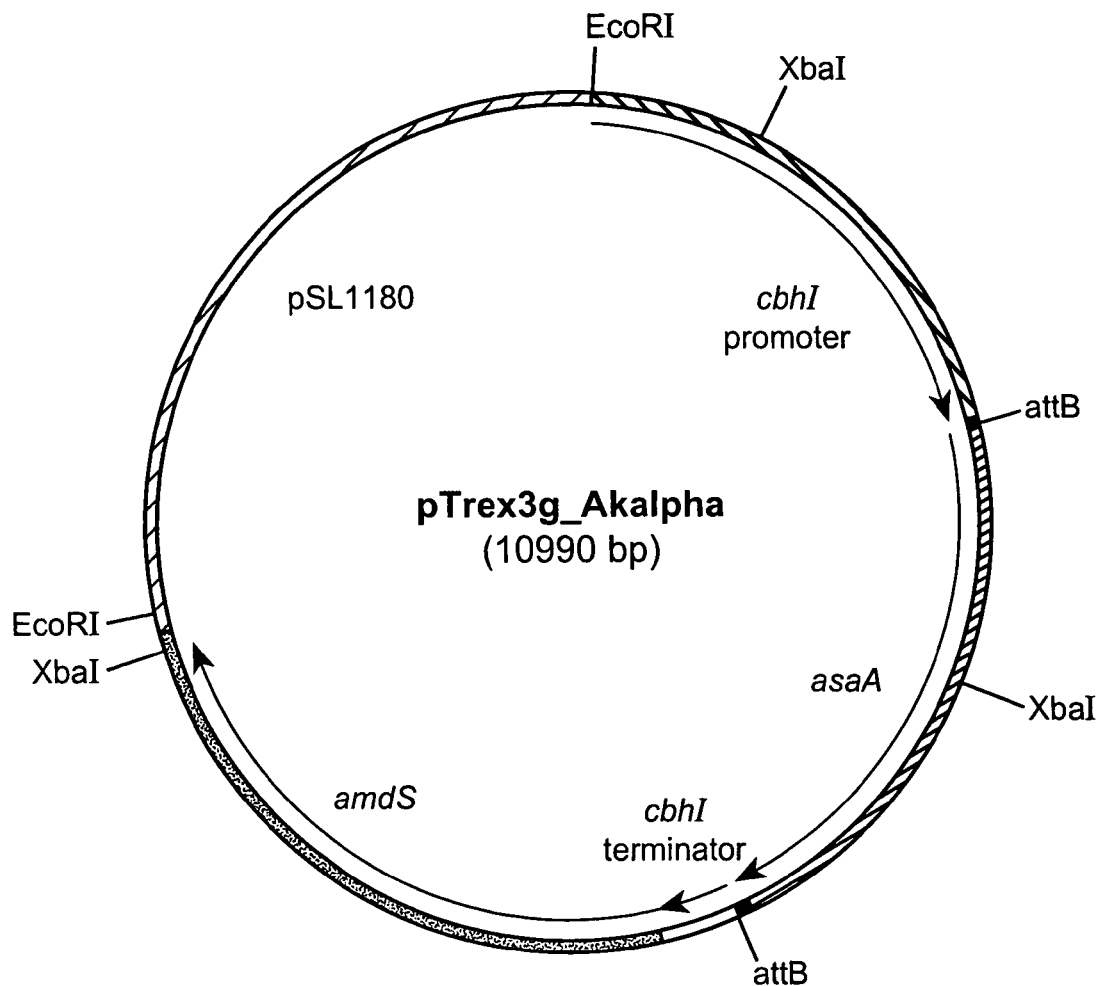
FIG. 4 provides a map of pTrex3g_Akalpha, which was used for expression of the nucleic acid encoding the AsaA (*Aspergillus kawachi* asAA) and which contains EcoRI sites flanking the fungal expression vector, wherein a) cbhI promoter is the *Trichoderma reesei* cellobiohydrolase promoter;
 b) asaA is the *Aspergillus kawachi* polynucleotide encoding the acid stable alpha amylase of SEQ ID NO. 4;
 c) cbhI terminator is the *Trichoderma reesei* cellobiohydrolase terminator;
 d) amdS is an *Aspergillus nidulans* acetamidase nutritional marker gene; and
 e) attB is a Gateway cloning system (Invitrogen) lambda phage site for recombination.

In some aspects, the present invention relies on routine techniques and methods used in the field of genetic engineering and molecular biology. The following resources include descriptions of general methodology useful in accordance with the invention: Sambrook et al., MOLECULAR CLONING: A LABORATORY MANUAL (2nd Ed., 1989); Kreigler, GENE TRANSFER AND EXPRESSION; A LABORATORY MANUAL (1990) and Ausubel et al., Eds. CURRENT PROTOCOLS IN MOLECULAR BIOLOGY (1994). These general references provide definitions and methods known to those in the art. However, it is not intended that the present invention be limited to any particular methods, protocols, and reagents described, as these may vary.

Unless defined otherwise herein, all technical and scientific terms used herein have the same meaning as commonly understood by one of ordinary skill in the art to which this invention belongs. Singleton, et al., DICTIONARY OF MICROBIOLOGY AND MOLECULAR BIOLOGY, 2D ED., John Wiley and Sons, New York (1994) and Hale & Markham, THE HARPER COLLINS DICTIONARY OF BIOLOGY, Harper Perennial, N.Y. (1991) provide one of skill with general dictionaries of many of the terms used in this invention.

Although any methods and materials similar or equivalent to those described herein can be used in the practice or testing of the present invention, the preferred methods and materials are described.

The invention will now be described in detail by way of reference only using the following definitions and examples. All patents and publications, including all sequences disclosed within such patents and publications, referred to herein are expressly incorporated by reference.

Numeric ranges are inclusive of the numbers defining the range.

Unless otherwise indicated, nucleic acids are written left to right in 5' to 3' orientation; amino acid sequences are written left to right in amino to carboxy orientation, respectively.

The headings provided herein are not limitations of the various aspects or embodiments of the invention which can be had by reference to the specification as a whole.

DEFINITIONS

As used herein the term "starch" refers to any material comprised of the complex polysaccharide carbohydrates of plants, comprised of amylose and amylopectin with the formula $(C_6H_{10}O_5)_x$, wherein X can be any number. In particular, the term refers to any plant-based material including but not limited to grains, grasses, tubers and roots and more specifically wheat, barley, corn, rye, rice, sorghum, brans, cassava, millet, potato, sweet potato, and tapioca.

As used herein the term "granular starch" refers to raw (uncooked) starch, e.g., starch that has not been subject to gelatinization.

As used herein the terms "granular starch hydrolyzing (GSH) enzyme" and "having granular starch hydrolyzing (GSH) activity" refer to enzymes, which have the ability to hydrolyze starch in granular form.

As used herein the term "alpha-amylase (e.g., E.C. class 3.2.1.1)" refers to enzymes that catalyze the hydrolysis of alpha-1,4-glucosidic linkages. These enzymes have also been described as those effecting the exo or endohydrolysis of 1,4-α-D-glucosidic linkages in polysaccharides containing 1,4-α-linked D-glucose units. Another term used to describe these enzymes is "glycogenase". Exemplary enzymes include alpha-1,4-glucan 4-glucanohydrase glucanohydrolase.

As used herein the term "acid-stable alpha amylase ("asAA") refers to an alpha amylase that has activity in the pH range of pH 3.0 to 7.0 and also in the pH range of 3.5 to 6.5.

As used herein the term "truncated" such as "truncated alpha amylase" refers to an enzyme, wherein at least part of the starch binding domain has been eliminated, but the functional portion retains a biological function, such as a catalytic function.

As used herein the term "starch binding domain (SBD)" refers to an amino acid sequence that binds preferentially to a starch (polysaccharide) substrate.

As used herein the term "linker" refers to a short amino acid sequence generally having between 3 and 40 amino acid residues which covalently bind an amino acid sequence comprising a starch binding domain with an amino acid sequence comprising a catalytic domain.

As used herein the term "catalytic domain" refers to a structural region of a polypeptide which is distinct from the SBD and which contains the active site for substrate hydrolysis.

As used herein the term "glucoamylase" refers to the amyloglucosidase class of enzymes (e.g., EC.3.2.1.3, glucoamylase, 1,4-alpha-D-glucan glucohydrolase). These are exo-acting enzymes, which release glucosyl residues from the non-reducing ends of amylose and amylopectin molecules. The enzyme also hydrolyzes alpha-1,6 and alpha-1,3 linkages although at much slower rate than alpha-1,4 linkages.

As used herein the term "glycosylation" refers to the post-transcriptional modification of a protein by the addition of carbohydrate moieties, wherein the carbohydrate is either N-linked or O-linked resulting in a glycoprotein. An N-linked carbohydrate moiety of a glycoprotein is attached by a glycosidic bond to the β-amide nitrogen of an asparagine residue. An O-linked carbohydrate is attached by a glycosidic bond to a protein through the hydroxy group of a serine or a threonine residue.

As used herein the term "recombinant" when used in reference to a cell, nucleic acid, protein or vector, indicates that the cell, nucleic acid, protein or vector, has been modified by the introduction of a heterologous nucleic acid or protein or the alteration of a native nucleic acid or protein, or that the cell is derived from a cell so modified. Thus, for example, recombinant cells express genes that are not found within the native (non-recombinant) form of the cell or express native genes that are otherwise abnormally expressed, under expressed or not expressed at all.

As used herein the terms "protein" and "polypeptide" are used interchangeably herein. The conventional one-letter or three-letter code for amino acid residues is used herein.

As used herein the term "signal sequence" means a sequence of amino acids bound to the N-terminal portion of a protein, which facilitates the secretion of the mature form of the protein outside the cell. The definition of a signal sequence is a functional one. The mature form of the extracellular protein lacks the signal sequence, which is cleaved off during the secretion process.

As used herein the term "native acid-stable alpha amylase (n-asAA)" refers to an acid-stable alpha amylase (asAA) produced from the endogenous expression of the asAA. For example, the term "n-asaA" means the endogenous expression of an acid-stable alpha amylase (e.g., SEQ ID NO: 3) from an *Aspergillus kawachi*.

As used herein the terms "recombinant acid-stable alpha amylase (r-asAA)", "recombinantly expressed asAA" and "recombinantly produced asAA" refer to a mature asAA protein sequence that is produced in a host cell from the expression of a heterologous polynucleotide. For example, the term "r-asaA" means the *Aspergillus* kawachi acid-stable alpha amylase (e.g., SEQ ID NO: 3) is expressed and produced in a host in which a polynucleotide encoding the asaA has been introduced.

As used herein the term "gene" refers to a DNA segment that is involved in producing a polypeptide and includes regions preceding and following the coding regions as well as intervening sequences (introns) between individual coding segments (exons).

As used herein the term "nucleic acid" encompasses DNA, RNA, single stranded or double stranded and chemical modifications thereof.

The terms "nucleic acid" and "polynucleotide" may be used interchangeably herein.

As used herein the term "vector" refers to a polynucleotide sequence designed to introduce nucleic acids into one or more cell types. Vectors include cloning vectors, expression vectors, shuttle vectors, plasmids, phage particles, cassettes and the like.

As used herein the term an "expression vector" means a DNA construct comprising a DNA sequence which is operably linked to a suitable control sequence capable of effecting expression of the DNA in a suitable host. Such control sequences may include a promoter to effect transcription, an optional operator sequence to control transcription, a sequence encoding suitable ribosome binding sites on the mRNA, enhancers and sequences which control termination of transcription and translation.

As used herein the term "promoter" means a regulatory sequence that is involved in binding RNA polymerase to initiate transcription of a gene. The promoter may be an inducible promoter or a constitutive promoter.

As used herein the phrase "under transcriptional control" indicates that transcription of a polynucleotide sequence, usually a DNA sequence, depends on its being operably linked to an element which contributes to the initiation of, or promotes transcription.

As used herein the phrase "under translational control" is a term well understood in the art that indicates a regulatory process that occurs after mRNA has been formed.

As used herein when describing proteins and genes that encode them, the term for the gene is generally italicized, (e.g., the gene that encodes asaA (*A. kawachi* asAA) may be denoted as *asaA*). The term for the protein is generally not italicized and the first letter is generally capitalized, (e.g., the protein encoded by the *asaA* gene may be denoted as AsaA or asaA).

As used herein the term "derived" encompasses the terms "originated from", "obtained" or "obtainable from", and "isolated from" and as used herein means that the polypeptide encoded by the nucleotide sequence is produced from a cell in which the nucleotide is naturally present or in which the nucleotide sequence has been inserted.

As used herein the term "operably linked" refers to juxtaposition wherein the elements are in an arrangement allowing them to be functionally related. For example, a promoter is operably linked to a coding sequence if it controls the transcription of the sequence.

As used herein the term "selective marker" refers to a gene capable of expression in a host that allows for ease of selection of those hosts containing an introduced nucleic acid or vector.

A polynucleotide or a polypeptide having a certain percent (e.g. 80%, 85%, 90%, 95%, or 99%) of sequence identity with another sequence means that, when aligned, that percentage of bases or amino acid residues are the same in comparing the two sequences. This alignment and the percent homology or identity can be determined using any suitable software program known in the art, for example those described in CURRENT PROTOCOLS IN MOLECULAR BIOLOGY (F. M. Ausubel et al. (eds) 1987, Supplement 30, section 7.7.18). Preferred programs include the GCG Pileup program, FASTA (Pearson et al. (1988) *Proc. Natl. Acad. Sci. USA* 85:2444-2448), and BLAST (BLAST Manual, Altschul et al., Natl. Cent. Biotechnol. Inf., Natl Lib. Med. (NCIB NLM NIH), Bethesda, Md., and Altschul et al., (1997) *NAR* 25:3389-3402). Another preferred alignment program is ALIGN Plus (Scientific and Educational Software, PA), preferably using default parameters. Another sequence software program that finds use is the TFASTA Data Searching Program available in the Sequence Software Package Version 6.0 (Genetics Computer Group, University of Wisconsin, Madison, Wis.). Because the genetic code is degenerate, more than one codon may be used to encode a particular amino acid, and the present invention encompasses polynucleotides, which encode a particular amino acid sequence.

One skilled in the art will recognize that sequences encompassed by the invention are also defined by the ability to hybridize under stringent hybridization conditions with the exemplified asaA sequence (e.g., SEQ ID NO:1). A nucleic acid is hybridizable to another nucleic acid sequence when a single stranded form of the nucleic acid can anneal to the other nucleic acid under appropriate conditions of temperature and solution ionic strength. Hybridization and washing conditions are well known in the art (See, e.g., Sambrook (1989) supra, particularly chapters 9 and 11). In some embodiments, stringent conditions correspond to a Tm of 65° C. and 0.1×SSC, 0.1% SDS.

As used herein "host strain" or "host cell" means a suitable host for an expression vector or DNA construct comprising a polynucleotide encoding an alpha amylase according to the invention. Specifically, host strains are preferably filamentous fungal cells. The host cell may be a wild type filamentous fungal host cell or a genetically modified host cell. The term host cell or host strain means both the cells and protoplasts created from the cells of a filamentous fungal strain.

The term "filamentous fungi" refers to all filamentous forms of the subdivision Eumycotina (See, Alexopoulos, C. J. (1962), INTRODUCTORY MYCOLOGY, Wiley, New York and AINSWORTH AND BISBY DICTIONARY OF THE FUNGI, 9th Ed. (2001) Kirk et al., Eds., CAB International University Press, Cambridge UK). These fungi are characterized by a vegetative mycelium with a cell wall composed of chitin, cellulose, and other complex polysaccharides. The filamentous fungi of the present invention are morphologically, physiologically, and genetically distinct from yeasts. Vegetative growth by filamentous fungi is by hyphal elongation and carbon catabolism is obligatory aerobic. In the present invention, the filamentous fungal parent cell may be a cell of a species of, but not limited to, *Trichoderma*, (e.g., *Trichoderma reesei* (previously classified as *T. longibrachiatum* and currently also known as *Hypocrea jecorina*), *Trichoderma viride, Trichoderma koningii, Trichoderma harzianum*); *Penicillium* sp., *Humicola* sp. (e.g., *Humicola insolens* and *Humicola grisea*); *Chrysosporium* sp. (e.g., *C. lucknowense*), *Gliocladium* sp., *Aspergillus* sp. (e.g., *A. oryzae, A. niger, A. kawachi* and *A. awamori*), *Fusarium* sp., *Neurospora* sp., *Hypocrea* sp., and *Emericella* sp. (See also, Innis et al., (1985) *Sci.* 228:21-26).

As used herein, the term "*Trichoderma*" or "*Trichoderma* sp." refer to any fungal genus previously or currently classified as *Trichoderma*.

As used herein the term "culturing" refers to growing a population of microbial cells under suitable conditions in a liquid or solid medium. In one embodiment, culturing refers to fermentative bioconversion of a starch substrate, such as a substrate comprising granular starch, to an end-product (typically in a vessel or reactor). Fermentation is the enzymatic and anaerobic breakdown of organic substances by microorganisms to produce simpler organic compounds. While fermentation occurs under anaerobic conditions it is not intended that the term be solely limited to strict anaerobic conditions, as fermentation also occurs in the presence of oxygen.

As used herein the phrase "simultaneous saccharification and fermentation (SSF)" refers to a process in the production of end-products in which a microbial organism, such as an ethanol producing microorganism and at least one enzyme such as an alpha amylase are in the same process step. In one embodiment of the present invention, SSF refers to the contemporaneous hydrolysis of granular starch substrates to saccharides including glucose and the fermentation of the saccharides into alcohol in the same reactor vessel.

As used herein the term "contacting" refers to the placing of the respective enzyme(s) in sufficiently close proximity to the respective substrate to enable the enzyme(s) to convert the substrate to the end-product. Those skilled in the art will recognize that mixing solutions of the enzyme with the respective substrates can effect contacting.

As used herein the term "enzymatic conversion" in general refers to the modification of a substrate by enzyme action. The term as used herein also refers to the modification of a granular starch substrate by the action of an enzyme.

As used herein the term "saccharification" refers to enzymatic conversion of starch to glucose.

As used herein the term "gelatinization" means solubilization of a starch molecule by cooking to form a viscous suspension.

As used herein the term "gelatinization temperature" refers to the temperature at which gelatinization of a starch begins. The exact temperature of gelatinization depends on the specific starch and may vary depending on factors such as, plant species and environmental and growth conditions.

As used herein the phrase "below the gelatinization temperature" refers to a temperature less than the temperature that starts gelatinization.

As used herein the term "liquefaction" refers to the stage in starch conversion in which gelatinized starch is hydrolyzed to give low molecular weight soluble dextrins.

As used herein the term "degree of polymerization (DP)" refers to the number (n) of anhydroglucopyranose units in a given saccharide. Examples of DP1 are the monosaccharides, such as glucose and fructose. Examples of DP2 are the disaccharides, such as maltose and sucrose. A DP>3 denotes polymers with a degree of polymerization of greater than 3.

As used herein the term "end-product" or "desired end-product" refers to any carbon-source derived molecule product which is enzymatically converted from the starch substrate, such as a starch substrate comprising granular starch.

As used herein the term "dry solids content (ds)" refers to the total solids of a slurry in % on a dry weight basis.

As used herein the term "slurry" refers to an aqueous mixture containing insoluble solids.

As used herein the term "soluble starch hydrolyzate" refers to soluble products resulting from starch hydrolysis, which may comprise mono-, di-, and oligosaccharides (e.g. glucose, maltose and higher sugars).

As used herein the term "residual starch" refers to the remaining starch (soluble or insoluble) left in a composition after fermentation of a starch containing substrate.

As used herein the terms "distillers dried grain (DDG)" and "distillers dried grain with solubles (DDGS)" refer to useful co-products of grain fermentation.

As used herein the term "mash" refers to a mixture of a fermentable carbon source (carbohydrate) in water used to produce a fermented product, such as an alcohol. In some embodiments, the term "beer", "mash" and "fermentation broth" may be used interchangeability.

As used herein "ethanologenic microorganism" refers to a microorganism with the ability to convert a sugar or oligosaccharide to ethanol. The ethanologenic microorganisms are ethanologenic by virtue of their ability to express one or more enzymes that individually or together convert sugar to ethanol.

As used herein the term "ethanol producer" or ethanol producing microorganism" refers to any organism or cell that is capable of producing ethanol from a hexose or pentose. Generally, ethanol-producing cells contain an alcohol dehydrogenase and a pyruvate decarboxylase. Examples of ethanol producing microorganisms include fungal microorganisms such as yeast. A preferred yeast includes strains of *Saccharomyces*, particularly, *S. cerevisiae*.

As used herein the term "heterologous" with reference to a polynucleotide or protein refers to a polynucleotide or protein that does not naturally occur in a host cell. It is intended that the term encompass proteins that are encoded by naturally occurring genes, mutated genes, and/or synthetic genes.

As used herein the term "endogenous" with reference to a polynucleotide or protein refers to a polynucleotide or protein that occurs naturally in the host cell.

As used herein the terms "recovered", "isolated", and "separated" as used herein refer to a compound, protein, cell, nucleic acid or amino acid that is removed from at least one component with which it is naturally associated.

As used herein, the terms "transformed", "stably transformed" and "transgenic" used in reference to a cell means the cell has a non-native (e.g., heterologous) nucleic acid sequence integrated into its genome or as an episomal plasmid that is maintained through multiple generations.

As used herein, the term "expression" refers to the process by which a polypeptide is produced based on the nucleic acid sequence of a gene. The process includes both transcription and translation.

As used herein the term "overproducing glucoamylase strain" refers to a filamentous fungal host cell that expresses and produces glucoamylase and further secretes the glucoamylase from the cell such that the secreted glucoamylase comprises at least 40% of the total amount of secreted protein.

The term "introduced" in the context of inserting a nucleic acid sequence into a cell, means "transfection", or "transformation" or "transduction" and includes reference to the incorporation of a nucleic acid sequence into a eukaryotic or prokaryotic cell wherein the nucleic acid sequence may be incorporated into the genome of the cell (e.g., chromosome, plasmid, plastid, or mitochondrial DNA), converted into an autonomous replicon, or transiently expressed (e.g., transfected mRNA).

As used herein the term "specific activity" means an enzyme unit defined as the number of moles of substrate converted to product by an enzyme preparation per unit time under specific conditions. Specific activity is expressed as units (U)/mg of protein.

As used herein the term "enzyme unit" refers to the amount of enzyme that produces a given amount of product per given amount of time under assay conditions. In some embodiments, an enzyme unit refers to the amount of enzyme that produces 1 micromole of product per minute under the specified conditions of the assay. For example, in one embodiment, the term "glucoamylase activity unit" (GAU) is defined as the amount of enzyme required to produce 1 g of glucose per hour from soluble starch substrate (4% ds) under assay conditions of 60° C. and pH 4.2.

In another embodiment, a granular starch hydrolyzing enzyme unit (GSHE U) is defined as being the amount of GSHE required to produce 1 mg of glucose per minute from granular starch under assay conditions of, for example 25° C. at pH 5.0. In a preferred embodiment, a GSHE U is defined as being the amount of a GSHE required to produce 1 mg glucose/min from a granular starch substrate at 50° C. at pH 4.5.

The term "yield" refers to the amount of end-product or desired end-products produced using the methods of the present invention. In some preferred embodiments, the yield is greater than that produced using methods known in the art. In some embodiments, the term refers to the volume of the end product and in other embodiment the term refers to the concentration of the end product.

"ATCC" refers to American Type Culture Collection located at Manassas, Va. 20108 (ATCC; <www.atcc.org>).

"NRRL" refers to the Agricultural Research Service Culture Collection, National Center for Agricultural Utilization Research (and previously known as USDA Northern Regional Research Laboratory), Peoria, Ill.

"A", "an" and "the" include plural references unless the context clearly dictates otherwise.

As used herein the phrase "at least" when used in combination with a list of values or terms is meant to apply to each value or term in the list. For example, the phrase "at least 85%, 90%, 95% and 99% sequence identity" is used to denote at least 85%, at least 90%, at least 95% and/or at least 99% sequence identity.

As used herein the term "comprising" and its cognates are used in their inclusive sense; that is, equivalent to the term "including" and its corresponding cognates.

Alpha Amylases:

In one embodiment of the invention, an alpha amylase, such as an acid stable alpha amylase (asAA) having GSH activity, is obtained from a strain of *Aspergillus*, e.g., *A. oryzae*, *A. kawachi*, *A. niger*, and *A. awamori*. In certain embodiments, the alpha amylase is an acid stable alpha amylase that is obtained from a strain of *Aspergillus kawachi*.

In some embodiments, the alpha amylase (e.g., an asAA having GSH activity) comprises an amino acid sequence having at least 80%, 85%, 90%, 93%, 94%, 95%, 96%, 97%, 98% and 99% sequence identity with the amino acid sequence set forth in SEQ ID NO: 3. In another embodiment, the asAA comprises an amino acid sequence having at least 90% sequence identity with SEQ ID NO: 3. In a further embodiment, the asAA comprises an amino acid sequence having at least 95% sequence identity to SEQ ID NO: 3. The asAA may also comprise an amino acid sequence having at least 98% sequence identity with SEQ ID NO: 3. In a further embodiment, the asAA comprises the amino acid sequence of SEQ ID NO: 3. In some embodiments, SEQ ID NO: 3 or a sequence having at least 85% identity thereto is considered an intact asAA. More generally, an intact alpha amylase is an alpha amylase comprising a catalytic domain, linker region and a starch binding domain.

In some embodiments, the alpha amylase will include a catalytic domain having at least 96%, 97%, 98% and 99% sequence identity with SEQ ID NO: 9. In other embodiments, the alpha amylase will include a SBD having at least 70%, 75%, 80%, 85%, 90%, 93%, 95%, 96%, 97% 98% and 99% sequence identity with the SBD of SEQ ID NO: 10.

In further embodiments, the alpha amylase will comprise at least 97%, 98%, and 99% sequence identity with SEQ ID NO: 9; at least 96%, 97%, 98% and 99% sequence identity with SEQ ID NO: 8; and at least 95%, 96%, 97% and 99% sequence identity with SEQ ID NO: 10. In certain embodiments, the catalytic domain and the SBD are obtained from an alpha amylase of an *Aspergillus kawachi* strain.

In other embodiments, the alpha amylase is a truncated enzyme. In some embodiments the truncated alpha amylase will include at least 60%, 65%, 70%, 75%, 80%, 83%, 85%, 88%, 90%, 93%, 95%, 96%, 97%, 98% and 99% of the amino acid sequence of SEQ ID NO: 3 and in other embodiments a truncated alpha amylase will encompass at least 60%, 65%, 70%, 75%, 80%, 83%, 85%, 88%, 90%, 93%, 95%, 96%, 97%, 98% and 99% of a sequence having at least 90%, 95%, 98% and 99% sequence identity with SEQ ID NO: 3. The enzyme may be truncated at the carboxy terminus end of the polypeptide. In some embodiments the truncated alpha amylase includes at least 430, 440, 450, 460 and 470 amino acids of SEQ ID NO: 3 or a sequence having at least 90% sequence identity thereto.

In some embodiments, the truncated alpha amylase will include at least 90%, 95%, 96%, 97%, 98% and 99% of the catalytic domain of SEQ ID NO: 9 or a sequence having at least 97%, 98% and 99% sequence identity thereto.

In some embodiments, the truncated alpha amylase will include the catalytic domain of SEQ ID NO: 9 or a sequence having at least 96%, 97%, 98% and 99% sequence identity thereto and a linker having at least 90%, 95%, 96%, 97%, 98% and 99% sequence identity to SEQ ID NO: 8. In some embodiments the truncated enzyme will include a catalytic domain having at least 97% sequence identity with SEQ ID NO: 9 and a linker having at least 95% sequence identity with SEQ ID NO: 8. In some embodiments, the truncated enzyme will include a catalytic domain having at least 96%, 97%, 98% and 99% sequence identity to SEQ ID NO: 9 and at least about 5, 10, 20, 25, 30 and 35 amino acids located downstream of the catalytic domain. In other embodiments, the truncated enzyme will include a catalytic domain and a linker as defined above and further a portion of the SBD having at least 70%, 75%, 80%, 85%, 90%, 93%, 95%, 96%, 97%, 98% and 99% sequence identity to the sequence of SEQ ID NO: 10. The portion of the SBD will include at least about 5, 10, 20, 30, 40, 50, 60, 70, 80, 90, and 100 amino acids located downstream of the linker.

In other embodiments, the asAA comprising the amino acid sequence of SEQ ID NO: 3 or an amino acid sequence having at least 95% sequence identity with SEQ ID NO: 3 is encoded by a polynucleotide having at least 70%, 80%, 85%, 90%, 93%, 95%, 96%, 97%, 98% and 99% sequence identity to the sequence of SEQ ID NO: 1. In one embodiment, the nucleic acid sequence encoding the asAA of SEQ ID NO: 3 (AsaA) is the nucleic acid sequence of SEQ ID NO: 1.

Recombinantly Expressed Enzymes and Host Cells:

In some embodiments of the invention, microorganisms are genetically engineered to express heterologous alpha amylases, such as an alpha amylase (e.g. an asAA having GSH activity) and having at least 80%, 85%, 90%, 93%, 94%, 95%, 96%, 97%, 98% and 99% sequence identity with SE ID NO: 3. Microorganisms may also be engineered to express heterologous glucoamylases. Preferred host cells are filamentous fungal cells. In some embodiments, the filamentous fungal host is a strain of an *Aspergillus* sp., a *Trichoderma* sp., a *Fusarium* sp. and a *Penicillium* sp.

Some preferred fungal host cells include *A. nidulans*, *A. awamori*, *A. oryzae*, *A. aculeatus*, *A. niger*, *A. japonicus*, *T. reesei*, *T. viride*, *F. oxysporum*, and *F. solani*. *Aspergillus* strains are disclosed in Ward et al. (1993) *Appl. Microbiol. Biotechnol.* 39:738-743 and Goedegebuur et al., (2002) *Curr Gene* 41:89-98. In some preferred embodiments, the host is a strain of *Trichoderma*, and particularly a strain of *T. reesei*. Strains of *T. reesei* are known and nonlimiting examples include ATCC No. 13631, ATCC No. 26921, ATCC No. 56764, ATCC No. 56765, ATCC No. 56767 and NRRL 15709. In some preferred embodiments, the host strain is a derivative of RL-P37. RL-P37 is disclosed in Sheir-Neiss et al. (1984) *Appl. Microbiol. Biotechnology* 20:46-53.

In other preferred embodiments, the host is a strain of *Aspergillus*. Useful *Aspergillus* host strains include without limitation *A. nidulans* (Yelton et al., (1984) Proc. Natl. Acad. Sci. USA 81: 1470-1474; Mullaney et al., (1985) *Mol. Gen. Genet.* 199:37-45; and Johnston et al., (1985) *EMBO J.* 4: 1307-1311); *A. niger* (Kelly et al., (1985) *EMBO J.* 4:475-479), *A. awamori* (NRRL 3112, UVK143f (U.S. Pat. No. 5,364,770), ATCC No. 22342, ATCC No. 44733, ATCC No. 14331 and ATCC No. 11490) and *A. oryzae* (ATCC No. 11490) and derivative strains thereof. In some embodiments, the *Aspergillus* strain is a pyrG mutant strain and consequentially requires uridine for growth. In some embodiments, the *Aspergillus* host strain expresses and produces endogenous alpha amylases. In some embodiments, the *Aspergillus* host strain is a strain that normally expresses and produces endogenous glucoamylases.

The term co-expression refers to the expression of a polynucleotide which has been introduced into a host cell which encodes an alpha amylase having at least 80% sequence identity to SEQ ID NO: 3, wherein the host cell or strain also expresses and produces a glucoamylase, such as an endogenous glucoamylase.

In some embodiments, the *Aspergillus* strain includes a wild-type glucoamylase although the strain may have been genetically engineered. Numerous *Aspergillus* strains express and produce glucoamylases. In particular, the gene encoding glucoamylase is highly expressed in many strains of *Aspergillus niger* and *Aspergillus awamori*. Glucoamylases are secreted enzymes so that the mature form of the glucoamylase is released to the external medium. Two forms of mature glucoamylases have been recognized in culture medium. These include GA I which is a full length form of glucoamylase comprising 616 amino acids and GA II which is a natural proteolytic fragment comprising 512 amino acids. GA II lacks a starch binding domain. See specifically, Boel et al., (1984) *EMBO J.* 3:1097-1102; WO 92/00381 and WO 00/04136 specifically incorporated by reference herein. Also reference is made to SEQ ID NO: 24 of WO 05/045018 and SEQ ID NO: 2 and SEQ ID NO: 13 of U.S. Pat. No. 6,352,851, incorporated herein by reference. The details of glucoamylase structure have been reviewed by Libby et al., (1994) Protein Engineering 7:1109-114.

In some embodiments, a *Trichoderma* host cell or an *Aspergillus* host cell is genetically engineered to express an asAA having GSH activity characterized by an amino acid sequence having at least 80%, 85%, 90%, 95%, 96%, 97%, 98% and 99% identity with SEQ ID NO: 3. In further embodiments, the asAA having GSH activity will comprise at least 97%, 98%, and 99% sequence identity with SEQ ID NO: 9; at least 96%, 97%, 98% and 99% sequence identity with SEQ ID NO: 8; and at least 95%, 96%, 97%, 98% and 99% sequence identity with SEQ ID NO: 10. In certain embodiments, the asAA is obtained from an alpha amylase of an *Aspergillus kawachi* strain.

In other embodiments, the invention comprises a nucleotide sequence which encodes the polypeptide of SEQ ID NO: 3, the polypeptide of SEQ ID NO: 9 or a truncated enzyme as defined herein. In some embodiments, the polynucleotide encoding an asAA will have a nucleic acid sequence of SEQ ID NO: 1 or a nucleic acid sequence having at least 70% sequence identity with SEQ ID NO: 1.

In some embodiments, the alpha amylase produced in a host cell engineered to include a heterologous polynucleotide encoding an asAA will have different, such as improved properties compared to the asAA produced by the endogenous expression of the asAA in a native host. These properties may include for example, increased enzyme activity, increased enzyme stability at lower pH levels or increased specific activity. In some embodiments, a heterologously produced asAA according to the invention may exhibit a maximum pH activity within a pH range of 3.0 to 6.0; also within a pH range of 3.0 to 5.0; within a pH range of 3.5 to 5.0 and also within a pH range of 3.5 to 4.5. In other embodiments, a heterologously produced asAA may have a greater stability or residual activity at a pH level of 3.0, 3.5, 4.0, 4.5 and/or 5.0 compared to a corresponding asAA endogenously produced from a native host under essentially the same conditions. In some embodiments, the level of enzyme stability for a heterologously produced asAA will be at least 0.5, 1.0, 2.0, or 2.5 times greater at a specific pH level compared to an endogenously expressed asAA at the same pH level. In some embodiments, these improved or different properties of the heterologously expressed asAA are particularly apparent in *Trichoderma* host cells. In some embodiments, the heterologously expressed asAA will be produced as an intact asAA having GSH activity which includes the catalytic domain, linker and SBD, for example the mature polypeptide illustrated in FIG. 2 (SEQ ID NO: 3). In other embodiments, the heterologously expressed asAA will be produced as a truncated asAA, for example, wherein the SBD is partially or completely cleaved off the catalytic domain.

In other embodiments, the host strain which is genetically engineered to express an asAA may also be genetically engineered to express a heterologous glucoamylase.

A host strain useful in the invention may have been previously manipulated through genetic engineering. In some embodiments, the genetically engineered host cell or strain may be a protease deficient strain. In other embodiments, expression of various native genes of the fungal host cell will have been reduced or inactivated. These genes include, for example genes encoding proteases and cellulolytic enzymes, such as endoglucanases (EG) and exocellobiohydrolases (CBH) (e.g. cbh1, cbh2, eg/1, eg/2 and eg/3). U.S. Pat. No. 5,650,322 discloses derivative strains of RL-P37 having deletions in the cbh1 gene and the cbh2 gene. Reference is also made to U.S. Pat. No. 5,472,864 and WO 05001036.

Vectors:

While the description below refers specifically to alpha amylases, such as asAA, one skilled in the art will readily understand that the same or similar methods apply to DNA constructs and vectors useful for introduction of a polynucleotide encoding GA into a host cell.

According to the invention, a DNA construct comprising nucleic acid encoding an asAA encompassed by the invention is constructed to transfer an asAA into a host cell. In one embodiment, the DNA construct is transferred to a host cell by an expression vector which comprises regulatory sequences operably linked to an asAA coding sequence.

The vector may be any vector which when introduced into a fungal host cell is integrated into the host cell genome and is replicated. Reference is made to the Fungal Genetics Stock Center Catalogue of Strains (FGSC, <www.fgsc.net>) for a list of vectors. Additional examples of suitable expression and/or integration vectors are provided in Sambrook et al., (1989) supra, Ausubel (1987) supra, van den Hondel et al. (1991) in Bennett and Lasure (Eds.) MORE GENE MANIPULATIONS IN FUNGI, Academic Press pp. 396-428 and U.S. Pat. No. 5,874,276. Particularly useful vectors include pFB6, pBR322, PUC18, pUC100 and pENTR/D.

In some embodiments, nucleic acid encoding an asAA encompassed by the invention is operably linked to a suitable promoter, which shows transcriptional activity in the fungal host cell. The promoter may be derived from genes encoding proteins either homologous or heterologous to the host cell. Preferably, the promoter is useful in a *Trichoderma* host or *Aspergillus* host. Suitable nonlimiting examples of promoters include cbh1, cbh2, eg/1, eg/2, pepA, hfb1, hfb2, xyn1 and amy. In one embodiment, the promoter is one that is native to the host cell. For example, when *T. reesei* is the host, the promoter is a native *T. reesei* promoter. In a preferred embodiment, the promoter is *T. reesei* cbh1, which is an inducible promoter and has been deposited in GenBank under Accession No. D86235. An "inducible promoter" is a promoter that is active under environmental or developmental regulation. In another embodiment, the promoter is one that is heterologous to the fungal host cell.

Other examples of useful promoters are those derived from the genes encoding of *A. awamori* and *A. niger* glucoamylase (glaA) (Nunberg et al., (1984) *Mol. Cell. Biol.* 4:2306-2315, U.S. Pat. No. 5,364,770, U.S. Pat. No. 6,590,078 (e.g. example 3); Gwynne D., et al., (1987) BioTechnol. 5:713-710 and Boel et al., (1984) *EMBO J.* 3:1581-1585); *Aspergillus niger* alpha amylases, *Aspergillus oryzae* TAKA amylase, *T. reesei* xln1, *T. reesei* cellobiohydrolase 1 (EPA 137280A1), *Rhizomucor miehei* aspartic proteinase and *A. niger* neutral alpha amylase.

In some embodiments, the asAA coding sequence is operably linked to a signal sequence. The DNA encoding the signal sequence is preferably that which is naturally associated with the asAA gene to be expressed. Preferably, the signal sequence is encoded by an *Aspergillus kawachi* asaA gene that encodes an Ak-asaA. More preferably the signal sequence has at least 90%, 95%, 97%, and 99% sequence identity to the signal sequence of SEQ ID NO: 2. In additional embodiments, a signal sequence and a promoter sequence comprising a DNA construct or vector to be introduced into a fungal host cell are derived from the same source. For example, in some embodiments, the signal sequence is the cdh1 signal sequence which is operably linked to a cdh1 promoter.

In some embodiments, the expression vector also includes a termination sequence. In one embodiment, the termination sequence and the promoter sequence are derived from the same source. In another embodiment, the termination sequence is homologous to the host cell. A particularly suitable terminator sequence is cbh1 derived from a *Trichoderma* strain and particularly *T. reesei*. Other useful fungal terminators include the terminator from *A. niger, A. tubingensis*, or *A. awamori* glucoamylase genes (Nunberg et al. (1984) supra, and Boel et al., (1984) supra).

In some embodiments, an expression vector includes a selectable marker. Examples of preferred selectable markers include but are not limited to ones that confer antimicrobial resistance (e.g., hygromycin, bleomycin, chloroamphenicol and phleomycin). Gene that confer metabolic advantage, such as nutritional selective markers, also find use in the present invention including those markers known in the art as amdS argB and pyr4. Markers useful in vector systems for transformation of *Trichoderma* are known in the art (See, e.g., Finkelstein, chapter 6 in BIOTECHNOLOGY OF FILAMENTOUS FUNGI, Finkelstein et al. Eds. Butterworth-Heinemann, Boston, Mass. (1992), Chap. 6.; and Kinghorn et al. (1992) APPLIED MOLECULAR GENETICS OF FILAMENTOUS FUNGI, Blackie Academic and Professional, Chapman and Hall, London). In a certain embodiments, the selective marker is the amdS gene, which encodes the enzyme acetamidase, allowing transformed cells to grow on acetamide as a nitrogen source. The use of *A. nidulans* amdS gene as a selective marker is described in Kelley et al., (1985) *EMBO J.* 4:475-479 and Penttila et al., (1987) *Gene* 61:155-164. In some embodiments, the vector will include the *A. niger* pyrG gene as a selectable marker and the *Aspergillus* strain that is transformed using a pyrG marker will be a pyrG mutant strain.

An expression vector comprising a DNA construct with a polynucleotide encoding an alpha amylase may be any vector which is capable of replicating autonomously in a given fungal host organism or of integrating into the DNA of the host. In some embodiments, the expression vector is a plasmid. In preferred embodiments, two types of expression vectors for obtaining expression of genes are contemplated.

The first expression vector comprises DNA sequences in which the promoter, asAA coding region, and terminator all originate from the gene to be expressed. In some embodiments, gene truncation is obtained by deleting undesired DNA sequences (e.g., DNA encoding unwanted domains) to leave the domain to be expressed under control of its own transcriptional and translational regulatory sequences.

The second type of expression vector is preassembled and contains sequences required for high-level transcription and a selectable marker.

In some embodiments, the coding region for an asAA gene or part thereof is inserted into this general-purpose expression vector such that it is under the transcriptional control of the expression construct promoter and terminator sequences. In some embodiments, genes or part thereof are inserted downstream of the strong cbh1 promoter.

Methods used to ligate the DNA construct comprising a polynucleotide encoding an asAA, a promoter, a terminator and other sequences and to insert them into a suitable vector are well known in the art. Linking is generally accomplished by ligation at convenient restriction sites. If such sites do not exist, the synthetic oligonucleotide linkers are used in accordance with conventional practice. (See, Sambrook (1989) supra, and Bennett and Lasure, MORE GENE MANIPULATIONS IN FUNGI, Academic Press, San Diego (1991) pp 70-76.). Additionally, vectors can be constructed using known recombination techniques (e.g., Invitrogen Life Technologies, Gateway Technology).

Where it is desired to obtain a fungal host cell having one or more inactivated genes known methods may be used (e.g. methods disclosed in U.S. Pat. No. 5,246,853, U.S. Pat. No. 5,475,101 and WO92/06209). Gene inactivation may be accomplished by complete or partial deletion, by insertional inactivation or by any other means which renders a gene nonfunctional for its intended purpose (such that the gene is prevented from expression of a functional protein). Any gene from a *Trichoderma* sp or other filamentous fungal host, such as an *Aspergillus* host, which has been cloned can be deleted, for example cbh1, cbh2, eg/1 and eg/2 genes. In some embodiments, gene deletion may be accomplished by inserting a form of the desired gene to be inactivated into a plasmid by methods known in the art. The deletion plasmid is then cut at an appropriate restriction enzyme site(s), internal to the desired gene coding region, and the gene coding sequence or part thereof is replaced with a selectable marker. Flanking DNA sequences from the locus of the gene to be deleted (preferably between about 0.5 to 2.0 kb) remain on either side of the marker gene. An appropriate deletion plasmid will generally have unique restriction enzyme sites present therein to enable the fragment containing the deleted gene, including the flanking DNA sequences and the selectable markers gene to be removed as a single linear piece.

Transformation, Expression and Culture of Host Cells:

Introduction of a DNA construct or vector into a host cell includes techniques such as transformation; electroporation; nuclear microinjection; transduction; transfection, (e.g., lipofection mediated and DEAE-Dextrin mediated transfection); incubation with calcium phosphate DNA precipitate; high velocity bombardment with DNA-coated microprojectiles; and protoplast fusion. General transformation techniques are known in the art (See, e.g., Ausubel et al., (1987), supra, chapter 9; and Sambrook (1989) supra, and Campbell et al., (1989) *Curr. Genet.* 16:53-56). The expression of heterologous protein in *Trichoderma* is described in U.S. Pat. No. 6,022,725; U.S. Pat. No. 6,268,328; Harkki et al. (1991); *Enzyme Microb. Technol.* 13:227-233; Harkki et al., (1989) *Bio. Technol.* 7:596-603; EP 244,234; EP 215,594; and Nevalainen et al., "*The Molecular Biology of Trichoderma and its Application to the Expression of Both Homologous and Heterologous Genes*", in MOLECULAR INDUSTRIAL MYCOLOGY, Eds. Leong and Berka, Marcel Dekker Inc., NY (1992) pp. 129-148). Reference is also made to Cao et al., (2000) *Sci.* 9:991-1001, EP 238023 and Yelton et al. (1984) *Proceedings. Natl. Acad. Sci.* USA 81:1470-1474 for transformation of *Aspergillus* strains.

Preferably, genetically stable transformants are constructed with vector systems whereby the nucleic acid encoding an alpha amylase (e.g. an asAA having at least 90% sequence identity with SEQ ID NO: 3) is stably integrated into a host strain chromosome. Transformants may then purified by known techniques.

In one nonlimiting example, stable transformants including an amdS marker are distinguished from unstable transformants by their faster growth rate and the formation of circular colonies with a smooth, rather than ragged outline on solid culture medium containing acetamide. Additionally, in some cases a further test of stability may be conducted by growing the transformants on solid non-selective medium (i.e., medium that lacks acetamide), harvesting spores from this culture medium and determining the percentage of these spores which subsequently germinate and grow on selective medium containing acetamide. Alternatively, other methods known in the art may be used to select transformants.

In one embodiment, the preparation of *Trichoderma* sp. or *Aspergillus* sp. for transformation involves the preparation of protoplasts from fungal mycelia. (See, Campbell et al., (1989) *Curr. Genet.* 16:53-56). In some embodiments, the mycelia are obtained from germinated vegetative spores. The mycelia are treated with an enzyme that digests the cell wall resulting in protoplasts. The protoplasts are then protected by the presence of an osmotic stabilizer in the suspending medium. These stabilizers include sorbitol, mannitol, potassium chloride, magnesium sulfate and the like. Usually the concentration of these stabilizers varies between about 0.8 M and about 1.2 M. In some embodiments, it may be preferable to use sorbitol and in other embodiments it may be preferable to use magnesium sulfate (e.g., about a 1.2 M solution of sorbitol in the suspension medium or about a 0.8 M magnesium sulfate solution in the suspension medium).

Uptake of DNA into the host strain may be dependent upon the calcium ion concentration. Generally, between about 10 mM $CaCl_2$ and 50 mM $CaCl_2$ may be used in an uptake solution. Besides the need for the calcium ion in the uptake solution, other compounds generally included are a buffering system such as TE buffer (10 Mm Tris, pH 7.4; 1 mM EDTA) or 10 mM MOPS, pH 6.0 buffer (morpholinepropanesulfonic acid) and polyethylene glycol (PEG).

Usually a suspension containing the host cells or protoplasts, such as *Trichoderma* sp. or *Aspergillus* sp. protoplasts or cells, which have been subjected to a permeability treatment at a density of about $10^5$ to about $10^7$/mL, preferably about $2\times10^6$/mL, and also about $1\times$ to $10^7$ are used in transformations. In some embodiments, a volume of about 100 µL of these protoplasts or cells in an appropriate solution (e.g., 1.2 M sorbitol; 50 mM $CaCl_2$) are mixed with the desired DNA. In some embodiments, a high concentration of PEG is added to the uptake solution. From 0.1 to 1 volume of 25% PEG 4000 can be added to the protoplast suspension. However, it is preferable to add about 0.25 volumes to the protoplast suspension. Additives such as dimethyl sulfoxide, heparin, spermidine, potassium chloride and the like may also be added to the uptake solution and aid in transformation. Similar procedures are available for other fungal host cells. (See, e.g., U.S. Pat. Nos. 6,022,725 and 6,268,328, both of which are incorporated by reference).

Generally, the mixture is then incubated at approximately 0° C. for a period of between 10 to 30 minutes. Additional PEG may be added to the mixture to further enhance the uptake of the desired gene or DNA sequence. In some embodiments, a 25% PEG 4000 is added in volumes of 5 to 15 times the volume of the transformation mixture; however, greater and lesser volumes may be suitable. The 25% PEG 4000 is preferably about 10 times the volume of the transformation mixture. After the PEG is added, the transformation mixture may be incubated either at room temperature or on ice before the addition of a sorbitol and $CaCl_2$ solution. The protoplast suspension is then further added to molten aliquots of a growth medium. When the growth medium includes a growth selection (e.g., acetamide or an antibiotic) it permits the growth of transformants only.

Generally, cells are cultured in a standard medium containing physiological salts and nutrients (See, e.g., Pourquie, J. et al., BIOCHEMISTRY AND GENETICS OF CELLULOSE DEGRADATION, eds. Aubert, J. P. et al., Academic Press, pp. 71-86, 1988 and Ilmen, M. et al., (1997) *Appl. Environ. Microbiol.* 63:1298-1306). Common commercially prepared media (e.g., Yeast Malt Extract (YM) broth, Luria Bertani (LB) broth and Sabouraud Dextrose (SD) broth) also find use in the present invention.

Culture conditions are also standard, (e.g., cultures are incubated at approximately 28° C. in appropriate medium in shake cultures or fermenters until desired levels of asAA expression are achieved). Culture conditions for a given filamentous fungus are known in the art and may be found in the scientific literature and/or from the source of the fungi such as the American Type Culture Collection and Fungal Genetics Stock Center.

After fungal growth has been established, the cells are exposed to conditions effective to cause or permit the expression and secretion of an alpha amylase and also of an alpha amylase (e.g. asAA) and glucoamylase as defined herein. In cases where an asAA having GSH activity coding sequence is under the control of an inducible promoter, the inducing agent (e.g., a sugar, metal salt or antimicrobial), is added to the medium at a concentration effective to induce asAA expression.

Identification of Enzyme Activity:

In order to evaluate the expression of an alpha amylase (e.g. asAA having GSH activity) by a cell line that has been transformed with a heterologous polynucleotide encoding an alpha amylase encompassed by the invention, assays can be carried out at the protein level, the RNA level or by use of functional bioassays particular to alpha amylase activity and/or production. In general assays employed include, Northern blotting, dot blotting (DNA or RNA analysis), RT-PCR (reverse transcriptase polymerase chain reaction), or in situ hybridization, using an appropriately labeled probe (based on the nucleic acid coding sequence) and conventional Southern blotting and autoradiography.

In addition, the production and/or expression of an enzyme encompassed by the invention may be measured in a sample directly, for example, by assays directly measuring reducing sugars such as glucose in the culture media and by assays for measuring glucoamylase activity, expression and/or production. Substrates useful for assaying GSH activity include granular starch substrates. For example, glucose concentration may be determined by any convenient method such as by using glucose reagent kit No 15-UV (Sigma Chemical Co.) or an instrument such as Technicon Autoanalyzer. Also reference is made to glucose oxidase kits and glucose hexose kits commercially available from Instrumentation Lab. (Lexington, Mass.).

In addition, gene expression may be evaluated by immunological methods, such as immunohistochemical staining of cells, tissue sections or immunoassay of tissue culture medium, e.g., by Western blot or ELISA. Such immunoassays can be used to qualitatively and quantitatively evaluate expression of an asaA. The details of such methods are known to those of skill in the art and many reagents for practicing such methods are commercially available.

Alpha amylase activity may be, for example, measured by using the DNS method as described in Miller, G. L. (1959) *Anal. Chem.* 31:426-428. Glucoamylase activity may be assayed for example by the 3,5-dinitrosalicylic acid (DNS) method (See, Goto et al., (1994) *Biosci. Biotechnol. Biochem.* 58:49-54).

In some embodiments of the invention, the asAA (e.g. an alpha amylase having at least 80% sequence identity to SEQ Di NO: 3) produced by a *Trichoderma* or *Aspergillus* host will be greater than 1 gram protein per liter (g/L), greater than 2 g/L, greater than 5 g/L, greater than 10 g/L, greater than 20 g/L, greater than 25 g/L, greater than 30 g/L, greater than 50 g/L and also greater than 100 g/L of culture media.

In some embodiments, the amount of secreted glucoamylase will be at least 15%, 20%, 25%, 30%, 35%, 40%, 45%, 50%, 55%, 60%, 65%, 70%, 75%, 80% and 95% of the total secreted protein from the host strain. In other embodiments, the amount of secreted glucoamylase will be greater than 50% of the total secreted protein. In some embodiments the amount of secreted glucoamylase will be less than 50% of the total secreted protein. In some embodiments, the amount of secreted glucoamylase will be greater than the amount of secreted asAA from an *Aspergillus* strain. In some embodiments the ratio of secreted glucoamylase to secreted asAA from the *Aspergillus* strain (GA/asAA) will be at least 1/1, at least 2/1, at least 4/1 at least 6/1 and at least 8/1. In some embodiments the ratio will be greater than 8/1.

In particular embodiments, the host is an overproducing glucoamylase host strain. In some embodiments, the overproducing host strain will be an *Aspergillus* sp. strain, such as an *A. niger* strain. In some embodiments, the *Aspergillus* overproducing glucoamylase strain is one that expresses a wild-type glucoamylase. One embodiment of an overproducing glucoamylase host strain is a recombinant *Aspergillus niger* strain comprising a polynucleotide encoding an endogenous glucoamylase and a polynucleotide encoding a heterologous alpha amylase having at least 90% sequence identity to SEQ ID NO: 3 or SEQ ID NO: 4. In some embodiments the produced glucoamylase is a full length *A. niger* glucoamylase and in other embodiments the glucoamylase is a truncated *A. niger* glucoamylase such as SEQ ID NO: 2 or SEQ ID NO: 13 of U.S. Pat. No. 6,352,851

Methods for Purifying Enzymes:

In general, an enzyme of according to the invention (such as an alpha amylase or glucoamylase) which is produced in cell culture is secreted into the medium and may be separated or purified, e.g., by removing unwanted components from the cell culture medium. In some cases, an enzyme may be produced in a cellular form necessitating recovery from a cell lysate. In such cases the enzyme is purified from the cells in which it was produced using techniques routinely employed by those of skill in the art. Examples include, but are not limited to, affinity chromatography (Tilbeurgh et al., (1984) *FEBS Lett.* 16:215); ion-exchange chromatographic methods (Goyal et al., (1991) *Biores. Technol.* 36:37; Fliess et al., (1983) *Eur. J. App. Microbiol. Biotechnol.* 17:314; Bhikhabhai et al., (1984) *J. Appl. Biochem.* 6:336; and Ellouz et al., (1987) *Chromatography* 396:307), including ion-exchange using materials with high resolution power (Medve et al., (1998) *J. Chromatography A* 808:153; hydrophobic interaction chromatography (Tomaz and Queiroz, (1999) *J. Chromatography A* 865:123; two-phase partitioning (Brumbauer, et al., (1999) *Bioseparation* 7:287); ethanol precipitation; reverse phase HPLC; chromatography on silica or on a cat-ion-exchange resin such as DEAE; chromatofocusing; SDS-PAGE; ammonium sulfate precipitation; and gel filtration using, e.g., Sephadex G-75.

Fermentations:

In some embodiments of the present invention, fungal cells expressing a heterologous alpha amylase are grown under batch or continuous fermentation conditions. A classical batch fermentation is a closed system, wherein the composition of the medium is set at the beginning of the fermentation and is not subject to artificial alterations during the fermentation. Thus, at the beginning of the fermentation the medium is inoculated with the desired organism(s). In this method, fermentation is permitted to occur without the addition of any components to the system. Typically, a batch fermentation qualifies as a "batch" with respect to the addition of the carbon source and attempts are often made at controlling factors such as pH and oxygen concentration. The metabolite and biomass compositions of the batch system change constantly up to the time the fermentation is stopped. Within batch cultures, cells progress through a static lag phase to a high growth log phase and finally to a stationary phase where growth rate is diminished or halted. If untreated, cells in the stationary phase eventually die. In general, cells in log phase are responsible for the bulk of production of end product.

A variation on the standard batch system is the "fed-batch fermentation" system, which also finds use with the present invention. In this variation of a typical batch system, the substrate is added in increments as the fermentation progresses. Fed-batch systems are useful when catabolite repression is apt to inhibit the metabolism of the cells and where it is desirable to have limited amounts of substrate in the medium. Measurement of the actual substrate concentration in fed-batch systems is difficult and is therefore estimated on the basis of the changes of measurable factors such as pH, dissolved oxygen and the partial pressure of waste gases such as $CO_2$. Batch and fed-batch fermentations are common and well known in the art.

Continuous fermentation is an open system where a defined fermentation medium is added continuously to a bioreactor and an equal amount of conditioned medium is removed simultaneously for processing. Continuous fermentation generally maintains the cultures at a constant high density where cells are primarily in log phase growth.

Continuous fermentation allows for the modulation of one factor or any number of factors that affect cell growth and/or end product concentration. For example, in one embodiment, a limiting nutrient such as the carbon source or nitrogen source is maintained at a fixed rate an all other parameters are allowed to moderate. In other systems, a number of factors affecting growth can be altered continuously while the cell concentration, measured by media turbidity, is kept constant. Continuous systems strive to maintain steady state growth conditions. Thus, cell loss due to medium being drawn off must be balanced against the cell growth rate in the fermentation. Methods of modulating nutrients and growth factors for continuous fermentation processes as well as techniques for maximizing the rate of product formation are well known in the art of industrial microbiology.

Compositions:

A particularly useful enzyme composition according to the invention is a starch hydrolyzing enzyme composition (e.g. a granular starch hydrolyzing composition) which includes an alpha amylase having at least 85%, 90%, 95%, 96%, 97%, 98% or 99% sequence identity to SEQ ID NO: 3. In some embodiments, the alpha amylase (e.g. asAA) is obtained from the heterologous expression of asAA, such as the heterologous expression of an *Aspergillus kawachi* acid stable alpha amylase in a *Trichoderma* or *Aspergillus* host. In some embodiments the *Aspergillus* host is an overproducing glucoamylase host.

Another useful enzyme composition of the invention is a starch hydrolyzing enzyme composition (e.g. a granular starch hydrolyzing composition) which comprises a truncated alpha amylase (e.g. asAA) having at least 97%, 98% and 99% sequence identity to the sequence of SEQ ID NO: 9.

In further embodiments, an enzyme composition according to the invention will include a combination of alpha amylase enzymes which include a) intact asAA having GSH activity which includes a sequence having at least 85%, 90%, 95%, 96%, 97%, 98% and 99% identity to SEQ ID NO: 3 and b) a truncated alpha amylase. In some embodiments, the truncated alpha amylase will be a sequence having at least 96%, 97%, 98% and 99% sequence identity with the sequence of SEQ ID NO: 9.

In some embodiments, the amount of intact asAA having GSH activity compared to the total amount of asAA having GSH activity (intact plus truncated) in the enzyme composition will be at least about 20%, 25%, 30%, 35%, 40%, 45%, 50%, 55%, 60%, 65%, 70%, 75%, 80%, 85%, 90%, 95%, and 98%. In other embodiments, the ratio of intact asAA having GSH activity to truncated asAA having GSH activity in an enzyme composition according to the invention will be about 10% to 90%, 20% to 80%, 30% to 70%, 35% to 65%, 40% to 60%, 45% to 55%, 50% to 50%, 55% to 45%, 60% to 40%, 65% to 35%, 70% to 30%, 80% to 20% and 90% to 10% (intact to truncated). In some embodiments, the ratio of intact to truncated will be between about 40% to 60% and about 60% to 40%.

In some embodiments, the alpha amylase and optionally a glucoamylase produced by co-expression in the host will be available as a cell free filtrate (for example wherein the asAA is isolated from a culture medium), and in other embodiments, the alpha amylase is available in a culture medium containing the fungal host cells which express and secrete the alpha amylase (e.g., asAA having GSH activity). In a further aspect, the invention encompasses a fermentation or culture medium comprising an acid stable alpha amylase (asAA) having granular starch hydrolyzing activity produced from a culture of *Trichoderma* cells, said *Trichoderma* cells comprising a heterologous polynucleotide encoding the asAA which has at least 90% sequence identity with SEQ ID NO: 3.

In another embodiment, the invention encompasses a fermentation or culture medium comprising an acid stable alpha amylase (asAA) having granular starch hydrolyzing activity produced from a culture of *Aspergillus* cells, said *Aspergillus* cells comprising a heterologous polynucleotide encoding an asAA which has at least 90% sequence identity with SEQ ID NO: 3.

In another embodiment, the invention encompasses a fermentation or culture medium comprising an acid stable alpha amylase (asAA) and a glucoamylase wherein both the alpha amylase and glucoamylase are co-expressed from a culture of *Aspergillus* cells, said cells comprising a heterologous polynucleotide encoding an alpha amylase which has at least 90% sequence identity with SEQ ID NO: 3 and an endogenous polynucleotide coding for the glucoamylase.

In some embodiments, the alpha amylase and the glucoamylase in the culture medium are further recovered. The enzymes may be formulated for use in enzyme compositions for numerous applications. Some of these applications and compositions include but are not limited to for example starch hydrolyzing and saccharifying compositions, cleaning and detergent compositions (e.g., laundry detergents, dish washing detergents, and hard surface cleaning compositions), animal feed compositions, baking applications, such as bread and cake production, brewing applications, healthcare applications, textile applications, environmental waste conversion processes, biopulp processing, and biomass conversion applications.

In particular, the compositions encompassed by the invention are used in starch conversion, such as in the production of dextrose for fructose syrups, specialty sugars and also in alcohol and other end-product (e.g. organic acid, ascorbic acid) production.

As understood by those in the art, the quantity of alpha amylase (e.g., asAA having GSH activity) used in the compositions and methods of the present invention will depend on the enzymatic activity of the alpha amylase. In some embodiments, the range of an alpha amylase encompassed by the invention present in the enzyme compositions is from 0.001 to 80 SSU, 0.001 to 60 SSU, also 0.01 to 40 SSU; also 0.01 to 30 SSU; also 0.01 to 20 SSU; also 0.01 to 15 SSU; also 0.05 to 15 SSU and also 0.01 to 10 SSU per g ds.

Useful enzyme compositions according to the invention are enzyme compositions as described above which further comprise a secondary glucoamylase. A secondary glucoamylase is a glucoamylase obtained from a source that is different from the *Aspergillus* host, which comprises the heterologous polynucleotide encoding an alpha amylase encompassed by the invention (e.g. a polynucleotide encoding an alpha amylase having at least 90% sequence identity to SEQ ID NO: 3).

Glucoamylase (GA) (E.C. 3.2.1.3) enzymes, which may be useful in the compositions according to the invention may be wild type glucoamylases or genetically modified glucoamylases, which include variant and hybrid glucoamylases. In general, glucoamylases may be derived from bacteria, plants and fungal sources. Preferred glucoamylases useful in the compositions and methods of the invention are produced by several strains of filamentous fungi and yeast. In particular, glucoamylases secreted from strains of *Aspergillus* and *Trichoderma* are commercially important. Sources of these glucoamylases include: *Aspergillus niger* G1 and G2 glucoamylase and variants thereof (Boel et al., (1984) *EMBO J.* 3:1097-1102; WO 92/00381; WO 00/04136, WO 05/045018, see SEQ ID NO: 25 and U.S. Pat. No. 6,352,851); *Aspergillus awamori* glucoamylases (WO 84/02921 and WO 05/052148, see SEQ ID NO: 5); *Aspergillus oryzae* glucoamylases and variants thereof (Hata et al., (1991) *Agric. Biol. Chem.* 55:941-949) and *Aspergillus shirousami* (See, Chen et al., (1996) *Prot. Eng.* 9:499-505; Chen et al. (1995) *Prot. Eng.* 8:575-582; and Chen et al., (1994) *Biochem J.* 302:275-281). Glucoamylases are also obtained from strains of *Talaromyces* such as those derived from *T. emersonii, T. leycettanus, T. duponti* and *T. thermophilus* (WO 99/28488; U.S. Pat. No. RE: 32,153; and U.S. Pat. No. 4,587,215) and variants thereof; strains of *Rhizopus*, such as *R. niveus* and *R. oryzae* and variant thereof; strains of *Mucor*; strains of *Trichoderma*, such as *T. reesei* and *T. viride*; and strains of *Humicola*, such as *H. grisea* (See, Boel et al., (1984) *EMBO J.* 3:1097-1102; WO 92/00381; WO 00/04136; Chen et al., (1996) *Prot. Eng.* 9:499-505; Taylor et al., (1978) *Carbohydrate Res.* 61:301-308; U.S. Pat. No. 4,514,496; U.S. Pat. No. 4,092,434; WO 05/052148, see SEQ ID NO: 2 and 3, and Jensen et al., (1988) *Can. J. Microbiol.* 34:218-223). Other glucoamylases useful in the present invention include those obtained from *Athelia rolfsii* and variants thereof (U.S. Pat. No. 4,727,026; WO 04/111218 and SEQ ID NO: 26 of WO 05/045018).

Enzymes having glucoamylase activity used commercially are produced for example, from *Aspergillus niger* (trade name DISTILLASE, OPTIDEX L-400 and G ZYME G990 4X from Genencor International Inc.) or *Rhizopus* species (trade name CU.CONC from Shin Nihon Chemicals, Japan). Also the commercial digestive enzyme, trade name GLUCZYME from Amano Pharmaceuticals, Japan (Takahashi et al., (1985) *J. Biochem.* 98:663-671). Additional enzymes include three forms of glucoamylase (E.C.3.2.1.3) of a *Rhizopus* sp., namely "Gluc1" (MW 74,000), "Gluc2" (MW 58,600) and "Gluc3" (MW 61,400). Gluc1 finds particular use in the present invention.

Some GA enzymes are also granular starch hydrolyzing enzyme(s) (GSHE) (See e.g., Tosi et al., (1993) *Can. J. Microbiol.* 39:846-855). These GA-GSHEs not only have glucoamylase activity, but also are able to hydrolyze granular (raw) starch. GA-GSHEs have been recovered from fungal cells and particularly filamentous fungal cells such as *Humicola* sp., *Aspergillus* sp., *Trichoderma* sp. and *Rhizopus* sp. A *Rhizopus oryzae* GA-GSHE has been described in Ashikari et al., (1986) *Agric. Biol. Chem.* 50:957-964 and U.S. Pat. No. 4,863,864. Also reference is made to *Rhizopus niveus*. A *Humicola grisea* GA-GSHE is described by Allison et al., (1992) *Curr. Genet.* 21:225-229, Tosi et al., (1993) *Can. J. Microbiol.* 39: 846-852, Campos et al., (1995) *App. And Environ. Microbiol.* 61:2436-2438 and European Patent No., 171218. An *Aspergillus awamori* var. *kawachi* GA-GSHE is described by Hayashida et al., (1989) *Agric. Biol. Chem.* 53:923-929. An *Aspergillus shirousami* GA-GSHE is described by Shibuya et al., (1990) *Agric. Biol. Chem.* 54:1905-1914. One particular GA-GSHE preparation for use in the present invention includes enzyme preparations sold under the designation "M1" available from Biocon India, Ltd, India.

In one embodiment, a GA-GSHE enzyme may be derived from a strain of *Humicola grisea*, particularly a strain of *H. grisea* var. *thermoidea* (See, U.S. Pat. No. 4,618,579). In some preferred embodiments, the *Humicola grisea* GA-GSHE enzyme is recovered from fungi including ATCC 16453, NRRL (USDA Northern Regional Research Laboratory, Peoria, ILL) 15219, NRRL 15220, NRRL 15221, NRRL 15222, NRRL 15223, NRRL 15224 and NRRL 15225, as well as genetically altered strains thereof. These species produce enzymatic glucoamylase preparations that are immunologically the same (See, EP 0 171 218).

The amount of glucoamylase useful in an enzyme composition may be in the range of 0.001 to 30.0 GAU/g ds, also 0.001 to 25.0 GAU/g ds, also 0.01 to 25.0 GAU/g ds, also 0.1 to 25.0 GAU/g ds, also 0.01 to 20 GAU/g ds, also 0.01 to 15 GAU/g ds, also 0.01 to 10 GAU/g ds, also 0.1 to 10 GAU/g ds and also 0.05 to 5.0 GAU/g ds. The activity of a GA-GSHE preparation may be defined in terms of the glucoamylase activity.

Some useful enzymatic compositions include a mixture of an alpha amylase, such as asAA having at least 95% sequence identity to SEQ ID NO: 3 and a glucoamylase having 0.1 to 10 GAU/g ds. Another useful enzymatic composition includes a mixture of an asAA having at least 98% sequence identity to SEQ ID NO: 3 and a glucoamylase having 0.1 to 10 GAU/g ds. Yet another useful enzymatic composition includes a mixture of an alpha amylase having at least 98% sequence identity to SEQ ID NO: 9 and a glucoamylase having 0.1 to 10 GAU/g ds.

In some embodiments, the ratio of the activity of an alpha amylase encompassed by the invention (SSU) to GA activity (GAU) will be in the range of 40:1 to 1:40, also 30:1 to 1:30, also 20:1 to 1:20 and also 15:1 to 1:15. In further embodiments, the ratio (SSU to GAU) will be in the range of about 20:1 to 1:10; about 10:1 to 1:10; about 10:1 to 1:5; about 5:1 to 1:5, about 4:1 to 1:4; about 3:1 to 1:3; about 2:1 to 1:4 and also about 2:1 to 1:2. In some embodiments, the ratio of SSU to GAU will be between about 4:1 to 2:1.

In some embodiments, an alpha amylase, such as an asAA having GSH activity having at least 80% sequence with SEQ ID NO: 3 will be mixed with a slurry of a granular starch substrate in an amount of about 0.001 to 30 SSU per gram of dry solids or also in an amount of 0.01 to 15.0 SSU per gram of dry solids content of the slurry. In some embodiments, an asAA encompassed by the invention is added in an amount of about 0.01 to 10.0 SSU, about 0.01 to 5.0 SSU; about 0.05 to 10.0 SSU; about 0.05 to 5.0 SSU; about 0.1 to 10.0 SSU; about 0.1 to 5.0 SSU; about 0.1 to 2.0 SSU; about 0.25 to 2.5 SSU; about 0.5 to 5.0 SSU; about 0.5 to 2.5 SSU; and also about 0.5 to 1.5 SSU per gram of dry solids content of the slurry.

As understood by those in the art, the quantity of glucoamylase used in the method and compositions of the present invention depends on the enzymatic activity of the glucoamylase. In some embodiments, an amount of between 0.001 and 15.0 GAU of glucoamylase per gram (ds) slurry adjusted to 20-45% dry solids may be added. In some embodiments, the glucoamylase is added in an amount between 0.001 and 10 GAU; between 0.01 and 10.0 GAU; between 0.01 and 5.0 GAU; between 0.05 and 5.0 GAU: between 0.1 and 10.0 GAU; between 0.1 and 5.0 GAU; between 0.1 and 2.0 GAU; between 0.25 and 1.5 GAU of glucoamylase per gram (ds) slurry. In one embodiment, the dosage range for glucoamylase will be from 0.1 to 2.0 GAU/g (ds) slurry.

Additional enzymes may be included in the compositions and methods encompassed by the invention. These additional enzymes, which find use in the present invention include debranching enzymes such as pullulanases (E.C. 3.2.1.41) and isoamylases (E.C. 3.2.1.68). Such enzymes hydrolyze alpha-1,6-glucosidic bonds. Thus, during the hydrolysis of the starch, debranching enzymes remove successive glucose units from the non-reducing ends of the starch. Another enzyme that may be used in the compositions of the invention are beta-amylases (E.C. 3.2.1.2). These are exo-acting maltogenic amylases, which catalyze the hydrolysis of 1,4-alpha-glucosidic linkages in amylose, amylopectin and related glucose polymers. Some of these enzymes are characterized as having an optimum pH range from 4.5 to 7.0 and optimum temperature range from 40° C. to 65° C. Commercial beta-amylases are available for example SPEZYME BBA and OPTIMALT from Genencor International Inc.

Additional enzymes may include a second alpha amylase, one that is provided from a source other than the heterologous expression of an alpha amylase as encompassed by the invention (i.e an alpha amylase having at least 80% sequence identify with SEQ ID NO: 3). Examples of alpha amylases include both bacterial and fungal alpha amylases and variants thereof. Specific nonlimiting examples include alpha amylases from *Bacillus amyloliquefaciens, Bacillus stearothermophilus, B. licheniformis* and variants or hybrids thereof (U.S. Pat. No. 5,093,257; U.S. Pat. No. 6,093,562; U.S. Pat. No. 5,736,499; U.S. Pat. No. 5,958,739; U.S. Pat. No. 6,436, 888; U.S. Pat. No. 6,867,031; WO 96/39528; WO 96/23874 and WO 05/001064). Commercially available alpha amylases are SPEZYME FRED and SPEZYME ETHYL (Genencor International Inc.). Cyclodextrin glucanotransferases (CG-Tases) (e.g. E.C. 2.4.1.19) and variants thereof may also find use in the invention (U.S. Pat. No. 5,278,059; U.S. Pat. No. 5,545,587 and WO 05/003337).

Further additional enzymes which may be used are proteases, such as fungal and bacterial proteases. Fungal proteases include for example, those obtained from *Aspergillus*,

*Trichoderma, Mucor* and *Rhizopus*, such as *A. niger, A. awamori, A. oryzae* and *M. miehei*. Other enzymes include but are not limited to cellulases, such as endoglucanases; hemicellulases, such as mannases; lipases (e.g., E.C. 3.1.1.3), glucose oxidases, pectinases, xylanases, transglucosidases, alpha 1,6 glucosidases (e.g., E.C. 3.2.1.20) and cutinases (e.g. E.C. 3.1.1.74).

The effective amount of these enzymes to be included in the methods of the invention can be readily determined by one skilled in the art.

In some embodiments, an antimicrobial may be added to the compositions and fermentation medium of the invention. Antimicrobials are compounds that kill or inhibit the growth of microorganisms.

In one embodiment, an enzyme composition comprising an asaA as encompassed by the invention and in combination with a glucoamylase will be used for producing ethanol. In some embodiments, at least 8%, 10%, 12%, 14%, 16% and 18% ethanol will be produced using a composition of the invention. In some embodiments, the ethanol will be produced during a simultaneous saccharification and fermentation. In some embodiments, the enzyme composition comprising the alpha amylase and glucoamylase produced from the same *Aspergillus* strain will be contemporaneously combined with a slurry of a granular starch substrate and an ethanol producing microorganism and the mixture will be fermented in a single step. The slurry may have about 10-50% ds; about 10-45%; about 15-40%; about 20-40%; about 25-40%; or about 25-35% ds.

A granular starch substrate may be obtained from any plant part including stems, grains, roots and tubers. Particularly preferred plant sources include corn; wheat; rye; sorghum; rice; millet; barley; cassava; legumes, such as beans and peas; potatoes; sweet potatoes; bananas; sugarcane; and tapioca.

Specifically contemplated starch substrates are cornstarch and wheat starch. The starch from a grain may be ground or whole and includes corn solids, such as kernels, bran and/or cobs. In addition, the grain may be fractionated (e.g., endosperm, fiber or germ in corn or gluten, starch A or starch B in wheat). The starch may be highly refined raw starch or feedstock from starch refinery processes. Those of general skill in the art are well aware of available methods which may be used to prepare granular starch substrates for use in the methods encompassed by the invention. Some of these methods include dry milling of whole cereal grains using hammer mills and roller mills and wet milling.

Various starches are commercially available. For example, cornstarches are available from Cerestar, Sigma, and Katayama Chemical Industry Co. (Japan); wheat starches are available from Sigma; sweet potato starches are available from Wako Pure Chemical Industry Co. (Japan); and potato starch is available from Nakaari Chemical Pharmaceutical Co. (Japan).

Various references have reported on the amount of starch found in cereal grains and reference is made to The Alcohol Textbook, $3^{rd}$ Ed. K. Jacques et al., Eds. 1999, Nottingham University Press. For example, corn contains about 60-68% starch; barley contains about 55-65% starch; millet contains about 75-80% starch; wheat contains about 60-65% starch; and polished rice contains 70-72% starch.

In some embodiments, a granular starch substrate is slurried (generally with water) and the slurry comprises i) about 10 to about 55% dry solids content (ds); ii) about 15 to about 50% dry solids content; iii) about 20 to about 45% dry solids content; iv) about 25 to about 45% dry solids content; v) about 30 to about 45% dry solids content; vi) about 30 to about 40% dry solids content; and also vii) about 30 to 35% dry solids content. In some embodiments, the granular starch slurry is contacted with an enzyme composition according to the invention at a temperature below the gelatinization temperature of the starch in the granular starch substrate to yield glucose.

The exact temperature used in accordance with the methods of the invention depends upon the specific starch substrate used. General starch gelatinization temperature ranges are disclosed in Swinkels pages 32-38 in STARCH CONVERSION TECHNOLOGY, eds Van Beynum et al., (1985) Marcel Dekker Inc., NY and THE ALCOHOL TEXTBOOK, A REFERENCE FOR THE BEVERAGE, FUEL AND INDUSTRIAL ALCOHOL INDUSTRIES, $3^{rd}$ Ed., eds Jacques et al., 1999, Nottingham University Press, UK. In some embodiments, a method encompassed by the invention will be conducted at a temperature of least about 10° C., 15° C., 20° C., 25° C., 30° C., 35° C., 40° C., 45° C., 50° C., 55° C., 60° C., and 65° C. In other embodiments, the temperature will be between about 25-65° C., between about 30-65° C., between about 35-65° C., between about 40-65° C., and between about 45-65° C. In other embodiments, the temperature will be between about 25-45° C., about 25-40° C. and about 30-35° C. In preferred embodiments, the starch substrate is contacted with a composition of the invention at a temperature which is below the gelatinization temperature of the starch in the substrate and in some embodiments the substrate containing starch is never subjected to the thermal conditions used for liquefactions.

In some embodiments, a method encompassed by the invention will be conducted at a pH range of between pH 3.0 to 7.0; between pH 3.0 to 6.0, between pH 3.0 to 5.0, between 3.5 to 6.0, between pH 3.5 to 5.0, and between 3.5 to 4.5.

In some embodiments, the residence time of the method is from about 2 to 300 hrs, but more typically from 2 to 120 hours. In some embodiments, the process is conducted from about 5 to 100 hours. In other embodiments, the process is conducted from about 5 to 80 hours. In still other embodiments, the process is conducted for at least 5 hours but less than 100 hours. In other embodiments, the process is conducted for at least about 10 hours but less than about 100 hours.

In some embodiments, at least 60%, 65%, 70%, 75%, 80%, 85%, 90%, 94%, 95%, 96%, 97%, 98% and 99% of the dry solids of the granular starch is hydrolyzed. In some embodiments, the granular starch substrate is completely hydrolyzed. In some embodiments, at least 90% of the granular starch is hydrolyzed in 100 hours. In certain embodiments, at least 90% of the granular starch substrate is hydrolyzed in a time period of 24 hours. In other embodiments, at least 95% of the granular starch substrate is hydrolyzed in a time period of 24 hours.

The yield of glucose (percent of the total solubilized dry solids) may be at least about 85%, 90%, 91%, 92%, 93%, 94%, 95%, 96%, 97% and 98%. In some embodiments, the glucose may be used to produce high fructose syrups. In a preferred embodiment, the glucose is continually produced and substantially all of the glucose is used in the process to produce an end-product, such as ethanol and co-products such as DDGS. (Reference is made to MOLECULAR STRUCTURE AND FUNCTION OF FOOD CARBOHYDRATE, ED. G. G. BIRCH ET AL, APPLIED SCIENCE PUBLISHERS, LONDON). The glucose may also be used in a fermentation to produce other end products including but not limited to organic acids, enzymes, glycerol, amino acids, ascorbic acid intermediates, and other complex compounds, such as hormones and antibiotics.

EXPERIMENTAL

The following examples are provided in order to demonstrate and further illustrate certain preferred embodiments and aspects of the present invention and are not to be construed as limiting the scope thereof. Indeed, it is contemplated that these teachings will find use in further optimizing the process systems described herein.

In the disclosure and experimental section which follows, the following abbreviations apply:

asAA having GSH activity (an acid-stable alpha amylase having granular starch hydrolyzing activity); AkAA (the acid stable alpha amylase having SEQ ID NO: 3 or SEQ ID NO: 4 and sometimes used interchangeably with asaA); GA (glucoamylase); wt % (weight percent); ° C. (degrees Centigrade); rpm (revolutions per minute); $H_2O$ (water); $dH_2O$ (deionized water); $dlH_2O$ (deionized water, Milli-Q filtration); aa (amino acid); bp (base pair); kb (kilobase pair); kD (kilodaltons); g or gm (grams); μg (micrograms); mg (milligrams); μL (microliters); ml and mL (milliliters); mm (millimeters); μm (micrometer); M (molar); mM (millimolar); μM (micromolar); U (units); V (volts); MW (molecular weight); sec (seconds); min(s) (minute/minutes); hr(s) (hour/hours); PAGE (polyacrylamide gel electrophoresis); DO (dissolved oxygen); phthalate buffer (sodium phthalate in water, 20 mM, pH 5.0); PBS (phosphate buffered saline [150 mM NaCl, 10 mM sodium phosphate buffer, pH 7.2]); SDS (sodium dodecyl sulfate); Tris (tris(hydroxymethyl)aminomethane); w/v (weight to volume); w/w (weight to weight); v/v (volume to volume); Genencor (Genencor International, Inc., Palo Alto, Calif.); DDGS (Distilleries Dry Grain plus Solids); MT (Metric ton); and EtOH (ethanol).

The following assays and methods are used in the examples provided below:

Glucoamylase Assay:

Glucoamylase activity was measured using a well-known assay which is based on the ability of glucoamylase to catalyze the hydrolysis of p-nitrophenyl-alpha-D-glucopyranoside (PNPG) to glucose and p-nitrophenol. At an alkaline pH, the nitrophenol; forms a yellow color that is proportional to glucoamylase activity and is monitored at 400 nm and compared against an enzyme standard measured as a GAU.

The measurement of acid-stable alpha amylase activity is based on the degree of hydrolysis of soluble potato starch substrate (4% ds) by an aliquot of the enzyme sample at pH 4.5, 50° C. The reducing sugar content is measured using the DNS method as described in Miller, G. L. (1959) *Anal. Chem.* 31:426-428. One unit of the enzyme activity (SSU, soluble starch unit) is equivalent to the reducing power of 1 mg of glucose released per minute at the specific incubation conditions.

Determination of Total Starch Content:

The enzyme-enzyme starch liquefaction and saccharification process (dual enzyme method) was used to determine the total starch content. In a typical analysis, 2 g of the dry sample was taken in a 100 ml Kohlraucsh flask and 45 ml of MOPS buffer, pH 7.0 was added. The slurry was well stirred for 30 min. SPEZYME FRED (1:50 diluted in water), 1.0 ml was added and heated to boiling for 3-5 min. The flask was placed in an autoclave maintained at 121° C. for 15 min. After autoclaving the flask was placed in a water bath at 95° C. and 1 ml of 1:50 dilutes SPEZYME FRED was added and incubated for 45 min. The pH was adjusted to pH 4.2 and the temperature was reduced to 60° C. This was followed by addition of 20 ml acetate buffer, pH 4.2. Saccharification was carried out by adding 1.0 ml of 1:100 diluted OPTIDEX L-400 (Glucoamylase from Genencor International Inc.) and the incubation was continued for 18 hr at 60° C. The enzyme reaction was terminated by heating at 95° C. for 10 min. The total sugar composition was determined by HPLC analysis using glucose as a standard. The soluble starch hydrolysate from water extraction of a sample at room temperature without enzymatic treatment was subtracted from the total sugar.

Residual Starch Iodine Test:

A sample of the beer (fermentation broth) was centrifuged in 2 ml plastic centrifuge tubes. The supernatant was decanted and the tube containing the pellet was placed in an ice bath. Several drops of 0.025N iodine solution (0.1N iodine from VWR Cat. No. VW3207-1 diluted 4×) was added to the pellet and mixed. A positive (+) starch shows a range of color from blue to purple and the intensity of color is directly proportional to the concentration of starch. A negative result (−) remains yellowish.

Total Protein Analysis:

The total nitrogen (N) in the sample preparations was determined using the Kjeldhal method (American Assoc. Cereal Chemists (AACC), (1983), Methods 22B60 8th Ed. St Paul, Minn.). Protein content was calculated by 6.25× total N.

Ethanol and Carbohydrate Determinations:

Ethanol and carbohydrate composition of the samples were determined using the HPLC method as described herein: a) 1.5 mL Eppendorf centrifuge tube was filled with fermenter beer and cooled on ice for 10 min; b) the sample tube was centrifuged for 1 min in Eppendorf table top centrifuge; c) a 0.5 mL sample of the supernatant was transferred to a test tube containing 0.05 mL of Kill solution (1.1N $H_2SO_4$) and allowed to stand for 5 min; d) 5.0 mL of water was added to the test tube sample and then filtered into a HPLC vial through 0.45 μm Nylon Syringe Filter; and then run on HPLC.

HPLC conditions:

a) Ethanol System: Column: Phenomenex Rezex Organic Acid Column (RHM-Monosaccharide) #00H-0132-KO (Equivalent to Bio-Rad 87H); Column Temperature: 60° C.; Mobile Phase: 0.01 N $H_2SO_4$; Flow Rate: 0.6 mL/min; Detector: RI; and Injection Volume: 20 μL b) Carbohydrate System: Column: Phenomenex Rezex Carbohydrate (RCM-Monosaccharide) #00H-0130-KO (Equivalent to Bio-Rad 87H); Column Temperature: 70° C.; Mobile Phase: Nanopure DI $H_2O$; Flow Rate: 0.8 mL/min; Detector: RI; and Injection Volume: 10 μL (3% DS material).

The column separates based on the molecular weight of the saccharides, which are designated as DP1 (monosaccharides); DP2 (disaccharides); DP3 (trisaccharides) and DP+4 (oligosaccharide sugars having a degree of polymerization greater than 3).

Preparation of asaA from the Heterologous Expression in *Trichoderma reesei* Used in the Examples:

At the end of the fermentation of the *T. reesei*, which expresses asaA (prepared according to examples 2 and 3), the biomass was separated by centrifugation and the clear culture filtrate was concentrated using a 10,000 molecular weight cut-off ultrafiltration membrane. This ultra filtrated concentrate having (90 SSU/g) was used.

Preparation of *Aspergillus niger* Glucoamylase Used in the Examples was as Follows:

A selected *Aspergillus niger* strain as described in U.S. Pat. No. 3,249,514 was used. After fermentation, fungal mycelia were separated using conventional separation methods including filtration and centrifugation. The clear filtrate was concentrated by ultrafiltration at 5° C. to a specified activity.

Example 1

Cloning the *Aspergillus kawachi* acid-stable alpha-amylase gene

Genomic DNA was extracted from an overnight culture of *A. kawachi* mycelia. The FastDNA Kit (QbioGene, Carlsbad, Calif.) SPIN™ protocol was used according to the manufacturer's instructions for fungi. For homogenization, the sample was processed for 30 sec at speed 4.0 on a FastPrep Instrument. PCR primers were designed, based on the asaA sequence of A. Kaneko, et al. (Kaneko et al., (1996), *J. Ferm Bioeng* 81:292-298).

(A). For construction of the *T. reesei* expression vector, the sequence of the forward cloning primer, alph6, was CACCATGAGAGTGTCGACTTCAAG (SEQ ID NO. 6) and the sequence of the reverse cloning primer, Akaa3 was CTACCTCCACGTATCAACCAC (SEQ ID NO. 7). The forward primer contained a motif for directional cloning into the pENTR/D vector (Invitrogen). The gene was amplified from the genomic DNA with Pfu Turbo DNA polymerase (Stratagene, La Jolla, Calif.).

The 2.36 kb PCR product was purified by gel extraction (Gel Purification kit, Qiagen) and cloned into pENTR/D, according to the Invitrogen Gateway system protocol. The vector was then transformed into chemically competent Top10 *E. coli* (Invitrogen) with kanamycin selection. Plasmid DNA from several clones was digested with restriction enzymes to confirm the correct size insert. The alpha-amylase gene insert was sequenced (Sequetech, Mountain View, Calif.) from several clones (SEQ ID NO:1). Plasmid DNA from one clone, pENTR/D_Akaa#11, was added to the LR clonase reaction (Invitrogen Gateway system) with pTrex3g/amdS destination vector DNA. Recombination, in the LR clonase reaction, replaced the CmR and ccdB genes of the destination vector with the *A. kawachi* asaA from the pENTR/D vector. This recombination directionally inserted asaA between the cbhI promoter and terminator of the destination vector. Recombination site sequences of 48 and 50 bp remained upstream and downstream, respectively, of the alpha amylase. An aliquot of the LR clonase reaction was transformed into chemically competent Top10 *E. coli* and grown overnight with carbenicillin selection. Plasmid DNA from several clones was restriction digested to confirm the correct insert size. For removal of the fungal cassette from the bacterial plasmid, the Stratagene QuickChange protocol was followed to add an EcoRI site 3' to the amdS gene. The sequence of the entire fungal cassette was confirmed. Plasmid DNA from clone, pTrex3g_Akalpha#1 (FIG. 4) was digested with EcoRI to release the expression cassette including the cbhI promoter:asaA:cbhI terminator:amdS. This 7.8 kb cassette was purified by agarose extraction using standard techniques and transformed into a strain of *T. reesei* derived from the publicly available strain QM6a, as further described below.

(B). For construction of the *Aspergillus niger* expression vector, the sequence of the forward cloning primer, alpha 7, was 5'-GCGCGCTACGTAATGAGAGTGTCGACTTC (SEQ ID NO: 11) and the sequence of the reverse cloning primer, rsh46r, was 5' GCGCGCTACGTACTACCTCCACGTATC (SEQ ID NO: 12). The gene was amplified from the genomic DNA with pfu Turbo DNA polymerase (Stratagene, La Jolla, Calif.).

Figure 5A:
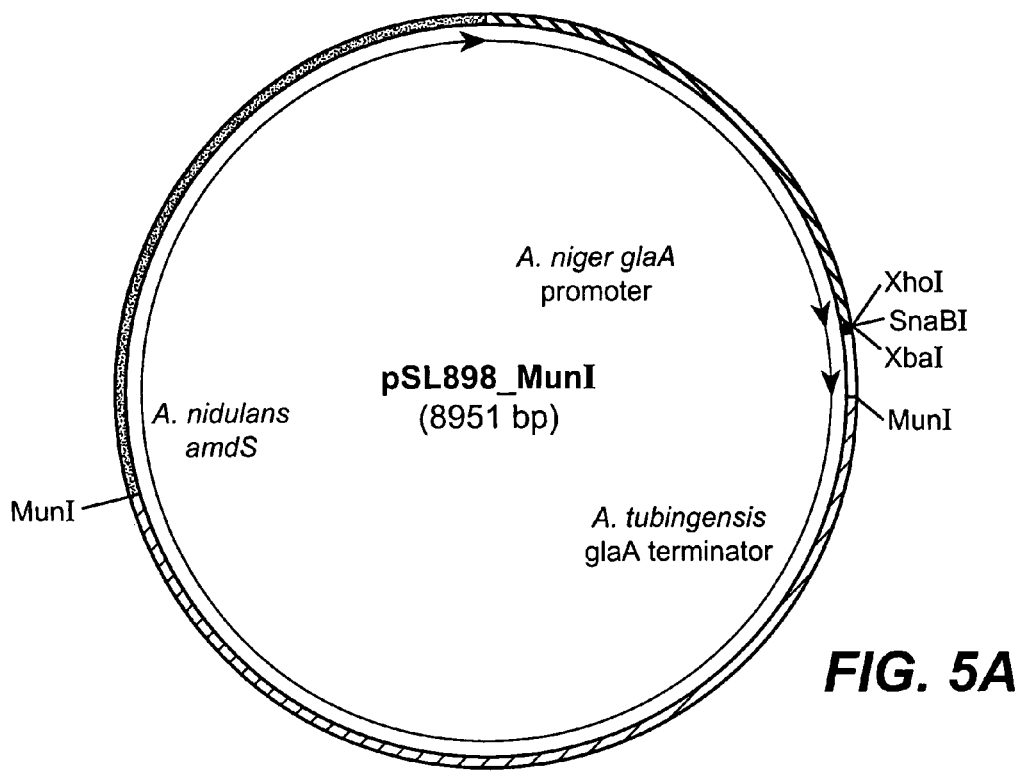
FIG. 5 provides a map of the pSL898_Muni plasmid (8951 bp) (view A) and the pSL902 plasmid (10782 bp) (view B), which were used for expression of the nucleic acid encoding the AsaA in an *Aspergillus niger* host.

The 2.36 kb PCR product was purified by gel extraction (Gel Purification kit, Qiagen) and cloned into pCR-BluntII-TOPO (Zero Blunt TOPO PCR cloning kit, Invitrogen) according to the manufacturer's protocol. The vector was transformed into One Shot® Top10 *E. coli* (Invitrogen) with kanamycin selection. Plasmid DNA from several clones was digested with restriction enzyme to confirm the correct size insert. The alpha amylase insert was sequenced (Sequetech, Mountain View, Calif.) from several clones (SEQ ID NO: 1). The sequenced 2.36 kb asaA gene was excised from the vector (clone TOPO-SnaBaa23) with restriction enzyme SnaBI and purified by gel extraction. Vector pSL898-MunI (FIG. 5A) containing the *A. niger* glucoamylase promoter, a multiple cloning site and *A. tubingensis* glucoamylase terminator was digested with SnaBI, which opened the plasmid between the glucoamylase promoter and terminator. Vector pSL898-MunI also includes the *A. nidulans* acetamide (amdS) selection marker for detection of fungal transformants by growth with acetamide as a sole nitrogen source. Vector digestion was followed by dephosphorylation with shrimp alkaline phosphatase (Roche Diagnostics Corp.). The isolated 2.36 kb SnaBI-flanked asaA was then ligated into the vector using T4DNA ligase (Roche Diagnostics Corp.), both according to the manufacturer's instructions. The ligation mixture was transformed into One Shot® Top10 *E. coli* (Invitrogen) with kanamycin selection. Clones were digested with XhoI to confirm orientation of the insert. The SnaBI site was altered during the blunt ligation. PCR (Pfu Turbo DNA polymerase) was then used to add ApaI sites to both the 5' and 3' ends of the fungal expression cassette. The sequence of the forward primer, a17 was GGGCCCATTTTGAATAGCTCGCCCGCTG (SEQ ID NO: 13) and the revrese primer, a18r, was GGGCCCCAATTGCCTAATGCTATGTGCAAG (SEQ ID NO: 14). The PCR product was cloned into pCR-BluntII-TOPO according to the manufacturer's instructions (with incubation increased to 1 hour at room temperature) and transformed into One Shot® Top 10 *E. coli* with kanamycin selection. Several clones were sequenced (Sequetech, Mountain View, Calif.) for accuracy.

Figure 5B:
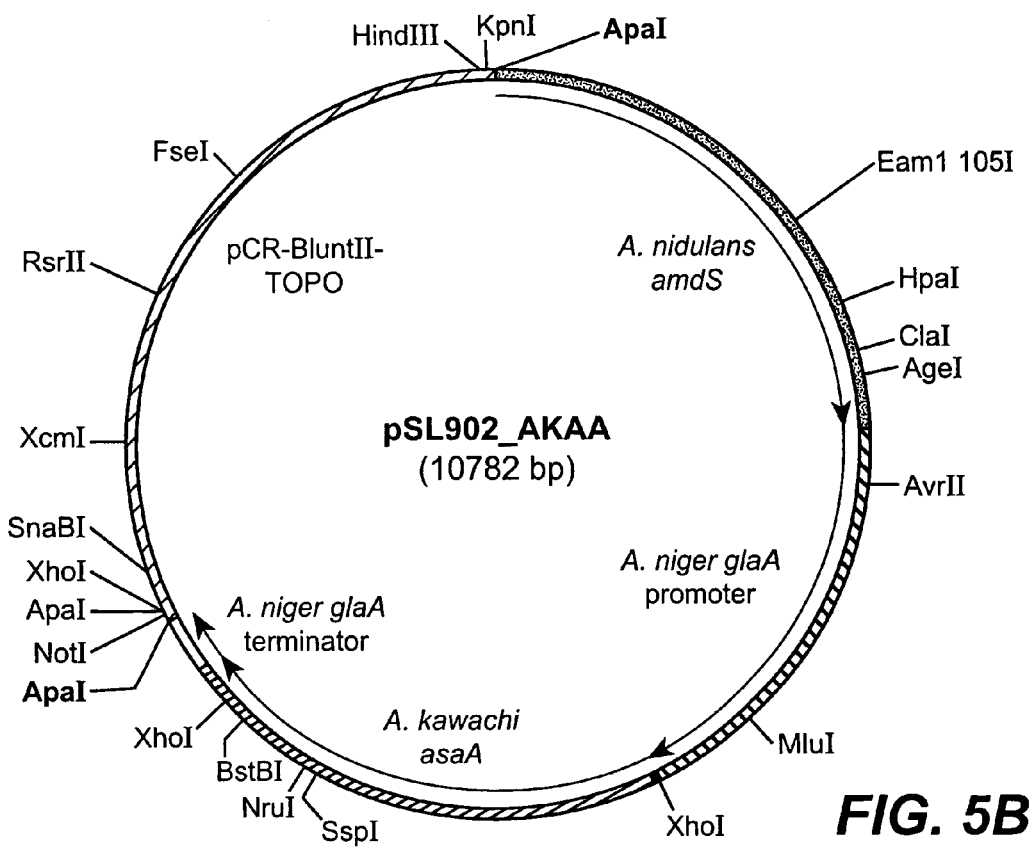

*E. coli* Clone #31, pSL902_AkAA (FIG. 5B) was used to generate plasmid DNA for transformation. The plasmid was digested with restriction enzyme ApaI to linearize the expression cassette, including the *A. nidulans* amdS, *A. niger* glaA promoter, *A. kawachi* alpha amylase (SEQ ID NO: 1) and *A. niger* glaA terminator. This 7.2 kb cassette was purified by agarose extraction using standard techniques and transformed into an *Aspergillus niger* strain, comprising an endogenous glucoamylase that is derived from ATCC 14916.

Example 2

Biolistic Transformation of *T. reesei*

A *Trichoderma reesei* spore suspension was spread onto the center ~6 cm diameter of an MABA transformation plate (150 µl of a $5 \times 10^7 - 5 \times 10^8$ spore/ml suspension). The plate was then air dried in a biological hood. The stopping screens (BioRad 165-2336) and macrocarrier holders (BioRad 1652322) were soaked in 70% ethanol and air dried. DriRite desiccant was placed in small Petri dishes (6 cm Pyrex) and overlaid with Whatman filter paper. The macrocarrier holder containing the macrocarrier (BioRad 165-2335) was placed flatly on top of filter paper and the Petri dish lid replaced.

A tungsten particle suspension was prepared by adding 60 mg tungsten M-10 particles (microcarrier, 0.7 micron, Bio-Rad #1652266) to an Eppendorf tube. 1 ml ethanol (100%) was added. The tungsten was votexed in the ethanol solution and allowed to soak for 15 minutes. The Eppendorf tube was microfuged briefly at maximum speed to pellet the tungsten. The ethanol was decanted and washed three times with sterile distilled water. After the water wash was decanted the third time, the tungsten was resuspended in 1 ml of sterile 50% glycerol. The tungsten was prepared fresh at least every two weeks.

The transformation reaction was prepared by adding 25 µl of suspended tungsten to a 1.5 ml Eppendorf tube for each transformation. Subsequent additions were made in order, 0.5-5 µl DNA (XbaI-digested expression cassette), 25 µl 2.5 M CaCl$_2$, 10 µl 0.1 M spermidine. The reaction was vortexed continuously for 5-10 minutes, keeping the tungsten suspended. The Eppendorf tube was then microfuged briefly and decanted. The tungsten pellet was washed with 200 µl of 70% ethanol, microfuged briefly to pellet and decanted. The pellet was washed with 200 µl of 100% ethanol, microfuged briefly to pellet, and decanted. The tungsten pellet was resuspended in 24 µl 100% ethanol. The Eppendorf tube was placed in an ultrasonic water bath for 15 seconds and 8 µl aliquots were transferred onto the center of the desiccated macrocarriers. The macrocarriers were left to dry in the desiccated Petri dishes.

A He tank was turned on to 1500 psi. 1100 psi rupture discs (BioRad 165-2329) were used in the Model PDS-1000/He Biolistic Particle Delivery System (BioRad). When the tungsten solution was dry, a stopping screen and the macrocarrier holder were inserted into the PDS-1000. An MABA plate, containing the target *T. reesei* spores, was placed 6 cm below the stopping screen. A vacuum of 29 inches Hg was pulled on the chamber and held. The He Biolistic Particle Delivery System was fired. The chamber was vented and the MABA plate removed for incubation at 28° C. until colonies appeared (5 days).

With reference to this Example 2 the following solutions were prepared,

Modified amdS Biolistic agar (MABA) per liter included: Part I, 1000× salts, 1.0 ml; Noble agar, 20 g made in 500 ml in dH$_2$O. Adjusted to pH to 6.0 and autoclaved. Part II, Acetamide, 0.6 g; CsCl, 1.68 g; Glucose, 20 g; KH$_2$PO$_4$, 15 g; MgSO$_4$.7H$_2$O, 0.6 g; and CaCl$_2$.2H$_2$O, 0.6 g made in 500 ml dH$_2$O. Adjusted to pH to 4.5 and 0.2 micron filter sterilized; left in 50° C. oven to warm, agar was added, mixed and poured into plates and stored at room temperature.

1000× Salts per liter=FeSO$_4$.7H$_2$O, 5 g; MnSO$_4$.H$_2$O, 1.6 g; ZnSO$_4$.7H$_2$, 1.4 g; COCl$_2$.6H$_2$O, 1 g brought up to 1 L with dH$_2$O, and 0.2 micron filter sterilized.

Example 3

PEG-Mediated Protoplast Fusion Transformation of *T. reesei*

A 1-2 cm$^2$ agar plug of a sporulated mycelia (grown on potato dextrose agar (PDA), Difco for 5 days at 30° C.) was inoculated into 50 ml of YEG (5 g/L yeast extract plus 20 g/L glucose) broth in a 250 ml, 4-baffle shake flask and incubated at 30-37° C. for 16-20 hours at 200 rpm. The mycelia were recovered by transferring the shake flask contents into 50 ml conical tubes and spinning at 2500 rpm for 10 minutes. The supernatant was discarded and the mycelial pellet was transferred into a 250 ml, 0.22 m CA or PES Corning filter bottle containing 40 ml of filtered β-D-glucanase solution. The solution was incubated at 30° C., 200 rpm, for 2 hours to generate protoplasts. Protoplasts were harvested by filtration, through sterile Miracloth (CalBiochem, La Jolla, Calif.), into a 50 ml conical tube. The protoplasts were pelleted by centrifugation at 2000 rpm for 5 minutes and the supernatant discarded. Protoplast pellets were washed once with 50 ml of 1.2 M sorbitol; centrifuged (2000 rpm, 5 min.) and supernatant was discarded. The pellet was washed with 25 ml of sorbitol/CaCl$_2$. A haemocytometer was used to count the protoplasts and then pelleted by centrifugation at 2000 rpm for 5 min. The supernatant was discarded and protoplast pellets resuspended in a volume of sorbitol/CaCl$_2$ sufficient to generate a protoplast solution with a protoplast concentration of 1.25×10$^8$/ml.

For each transformation, an aliquot of 20 µg of expression vector DNA (in a volume no greater than 20 µl) was transferred into 15 ml conical tubes, on ice. Protoplast suspension (200 µl) and 50 µl PEG solution was added to each tube. This was mixed gently and incubated on ice for 20 min. PEG (2 ml) solution was added to each transformation tube and incubated at room temperature for 5 minutes. 4 ml sorbitol/CaCl$_2$ solution was added to each tube (total volume 6.2 ml) and mixed gently. Then 2 ml of the transformation mixture was added to each of 3 molten (50° C.) top agar tubes. Each top agar mixture was poured onto a separate transformation plate and incubated at 30° C. for four to seven days.

For transformation with amdS selection, acetamide/sorbitol plates and top agar were used. Selection plates were the same as transformation plates, but without sorbitol. Putative transformants were purified by transferring isolated colonies to fresh selective media containing acetamide.

Media and solutions were prepared as follows. 40 ml β-D-glucanase solution—600 mg β-D-glucanase (InterSpex Products Inc., San Mateo, Calif.) and 400 mg MgSO$_4$.7H$_2$O was dissolved in 40 ml 1.2M sorbitol. 200 ml PEG mix—50 g PEG 4000 (BDH Laboratory Supplies Poole, England) and 1.47 g CaCl$_2$.2H$_2$O was dissolved in 200 ml dlH$_2$O. The PEG mix is made fresh at least every month. Sorbitol/CaCl$_2$ solution—50 mM CaCl$_2$ is dissolved in 1.2M sorbitol. Acetamide/sorbitol agar—Part 1: Dissolved 0.6 g acetamide (Aldrich, 99% sublime.), 1.68 g CsCl, 20 g glucose, 20 g KH$_2$PO$_4$, 0.6 g MgSO$_4$.7H$_2$O, 0.6 g CaCl$_2$.2H$_2$O, 1 ml 1000× salts (see below) in 200 ml dlH$_2$O, adjusted to pH 5.5, brought volume up to 300 mls with dH$_2$O, and this is filter sterilized. Part II: 20 g Noble agar and 218 g sorbitol were added to a 1 L cylinder, brought to volume (700 mls) with dlH$_2$O, and autoclaved. Part II was added to Part I for a final volume of 1 L. (1000× Salts—5 g FeSO$_4$.7H$_2$O, 1.6 g MnSO$_4$.H$_2$O, 1.4 g ZnSO$_4$.7H$_2$O, and 1 g CoCl$_2$.6H$_2$O are combined and brought up to 1 L volume with dlH$_2$O. This is then filtered sterilized.

Example 4

PEG-Mediated Protoplast Fusion Transformation of *Aspergillus niger*

A 250 ml, 4-baffle shake flask containing 100 ml of WCWM or WCWM+CD broth was inoculated with an −80° C. stock of a strain of *Aspergillus niger* mycelia which overexpress wild-type endogenous glucoamylase and which is derived from ATCC 14916. The culture was grown at 30° C. for 48-72 hours, 300 rpm. A 10% transfer was made into fresh WCWM or WCWM+CD shake flask. The second stage cultures were grown for 24 to 72 hours, 30° C., 300 rpm. Mycelia was harvested through a sterile Miracloth filter and washed with Solution A, or mycelia were spun down in an IEC swinging bucket centrifuge (2000 rpm). Washed mycelia was aseptically transferred into 40 ml of protoplasting solution and incubated at 30° C., 200 rpm, for 1-2 hours, protoplasting progress was monitored microscopically. The protoplasting reaction was filtered through sterile Miracloth, into two 50 ml sterile disposable centrifuge tubes and the volume brought up to 45 mls each with Solution B. The protoplasts were centrifuged at 2500 rpm for 5 minutes to obtain pellets and the supernatant was discarded. The pellet was washed twice more with 20 ml volumes of Solution B. The pellet was resuspended in 10 ml Solution B and protoplasts counted using a haemocytometer. Protoplasts were again centrifuged and the supernatant discarded. Protoplasts were resuspended, in Solution B to yield ~$1\times10^7$/100 µl. On ice, 100 µl protoplast solution was added to pre-chilled 15 ml tubes, one tube per transformation. 10 µg DNA was added in a volume not exceeding 10 µl. Solution C (12.5 µl) was added, mixed gently, and incubated on ice for 20 minutes.

MMSA top agar (3 tubes of 10 ml each, per transformation) was melted and maintained at 55° C. Protoplasts were removed from the ice and Solution C (1 ml) and Solution B (2 ml) were added to each tube and the tubes were mixed gently. 1 ml of the protoplast mixture was added to each of the 3 top agar tubes and the top agar was poured onto MMSA plates. This was repeated for each transformation and plates were incubated for 4-7 days at 30° C.

Solution A (per 500 ml)—0.44 g $K_2HPO_4$; 0.34 g $KH_2PO_4$; 48.156 g anhydrous $MgSO_4$ (FW 120.37); and $dlH_2O$ were added for a final volume of 500 ml, pH 5.5. The solution was filter sterilized and stored at room temperature.

Protoplasting solution—180 units beta-D-glucanase (InterSpex Products, Inc., CA) or 450 mg beta-D-glucanase and 150 mg Driselase (InterSpex Products, Inc.) were dissolved in 40 ml Solution A and the solution was filter sterilized, 0.2 micron.

Solution B (per 500 ml)—5 ml 1M Tris, pH 7.5; 2.77 g $CaCl_2$ (FW 110.99); 109.32 g Sorbitol (FW 182.2; 1.2M); and $dlH_2O$ were added for a final volume of 500 ml. This solution was filter sterilized and stored at room temperature.

Solution C (per 500 ml)—250 g PEG 4000; 2.77 g $CaCl_2$; 5 ml 1M Tris, pH 7.5; and $dlH_2O$ were added for a final volume of 500 ml. The solution was filter sterilized.

MMS Agar—Dissolved in 1 L $dlH_2O$, 6 g/L $NaNO_3$; 0.52 g/L KCl; 1.52 g/L $KH_2PO_4$; 218.5 g/L D-Sorbitol; 1 ml/L Trace elements (see below); 10 g/L agar (low melt agarose in the top agar). Autoclaved. Post-sterilization, aseptically added 10 ml 50% glucose and 1.25 ml 20% $MgSO_4.7H_2O$.

MMSA agar, the nitrate in the MMS was replaced with 0.59 g/L acetamide and 3.4 g/L CsCl.

Trace Elements Solution—Dissolved in 250 ml $dlH_2O$, 1 g/L $FeSO_4.7H_2O$; 8.8 g/L $ZnSO_4.7H_2O$; 0.4 g/L $CuSO_4.5H_2O$; 0.15 g/L $MnSO_4.4H_2O$; g/L $Na_2B_4O_7.10H_2O$; 50 mg/L $(NH_4)6Mo_7O_{24}.4H_2O$. Mixed and added 0.2 ml concentrated HCl to dissolve and brought up to 1 L with $dlH_2O$ and filter sterilized.

WCWM broth (1 liter)=$(NH_4)_2SO_4$, 3.5 g; DIFCO Yeast Extract, 4 g; Potato Dextrose Starch, 6 g; Mazu, 1 ml and Cerelose, 2.2 g.

WCWM+CD (1 liter)=$(NH_4)_2SO_4$, 3.5 g; Tastone 210 Yeast Extract, 4 g; Potato Dextrose Broth, 20 g; and DIFCO Czapek Dox, 20 g.

Example 5

Fermentation of *T. reesei* and *Aspergillus niger* Transformed with the asaA Gene Encoding AkAA and Enzyme Expression in Transformed Cells (A). *Trichoderma* Clones—

In general, the fermentation protocol as described in Foreman et al. (Foreman et al. (2003) *J. Biol. Chem.* 278:31988-31997) was followed. More specifically, duplicate fermentations were run for each of the strains displayed in FIG. 6A. 0.8 L of Vogels minimal medium (Davis et al., (1970) METHODS IN ENZYMOLOGY 17A, pg 79-143 and Davis, Rowland, NEUROSPORA, CONTRIBUTIONS OF A MODEL ORGANISM, Oxford University Press, (2000)) containing 5% glucose was inoculated with 1.5 ml frozen spore suspension. After 48 hours, each culture was transferred to 6.2 L of the same medium in a 14 L Biolafitte fermenter. The fermenter was run at 25° C., 750 RPM and 8 standard liters per minute airflow. One hour after the initial glucose was exhausted, a 25% (w/w) lactose feed was started and fed in a carbon limiting fashion to prevent lactose accumulation. The concentrations of glucose and lactose were monitored using a glucose oxidase assay kit or a glucose hexokinase assay kit with beta-galactosidase added to cleave lactose, respectively (Instrumentation Laboratory Co., Lexington, Mass.).

Samples were obtained at regular intervals to monitor the progress of the fermentation. Collected samples were spun in a 50 ml centrifuge tube at ¾ speed in an International Equipment Company (Needham Heights, Mass.) clinical centrifuge. Sample supernatants were run of 4-12% BIS-TRIS SDS-PAGE gels, under reducing conditions with MOPS (morpholinepropanesulfonic acid) SDS running buffer and LDS sample buffer (FIG. 6A).

In additional fermentations, sample supernatants were run as basically described above. However, different proportions of intact and truncated forms of Tr-asaA were obtained. FIG. 6B, lane 2 illustrates three major bands between 50 and 90 kD. The three bands from the gel digested using modified methods known in the art (Hellman et al., (1995) *Anal. Biochem.* 224:451-455). Peptides were extracted, separated using reverse phase HPLC and peptide mass and ms/ms fragmentation patterns determined. The resulting peptide maps confirmed that both lower MW bands were truncated. One band represented a truncated asAA in which clipping occurred between amino acid position 434 and 580 of SEQ ID NO: 3 and the second band represented a truncated asAA in which clipping took place at about amino acid position 581 of SEQ ID NO: 3. Each band exhibited alpha amylase and granular starch hydrolyzing activity.

(B). *Aspergillus* Clones—

Expression of both glucoamylase and *A. kawachi* alpha amylase was analyzed in *Aspergillus niger* transformants (obtained as described above). Glucoamylase activity and alpha amylase activity were measured by HPLC from sample supernatants from transformants. Of 27 transformants analyzed, at least 22 transformants produced over 0.5 mg/ml of AkAA. In addition at least 22 transformants produced at least 25% of the glucoamylase of the parental control (on an activity basis). At least 6 of these transformants produced over 1.5 mg/ml AkAA. Some of these results are illustrated below in Table 1.

TABLE 1

Co-Expression of Glucoamylase and *A. kawachi* alpha amylase in *Aspergillus niger*

| Transformant # | Relative GA level (%) Compared to control (100%) | Production of AkAA (mg/ml) |
|---|---|---|
| Control | 100 | — |
| 10 | 83 | 1.77 |
| 11 | 71 | 0.71 |
| 12 | 83 | 0.87 |
| 13 | 90 | 0.83 |
| 15 | 69 | 1.73 |
| 18 | 61 | 1.68 |
| 19 | 50 | 2.16 |
| 21 | 69 | 2.06 |

TABLE 1-continued

Co-Expression of Glucoamylase and *A. kawachi* alpha amylase in *Aspergillus niger*

| Transformant # | Relative GA level (%) Compared to control (100%) | Production of AkAA (mg/ml) |
|---|---|---|
| 22 | 70 | 1.7 |
| 24 | 77 | 0.85 |
| 26 | 100 | 0.95 |

Example 6

Figure 7:
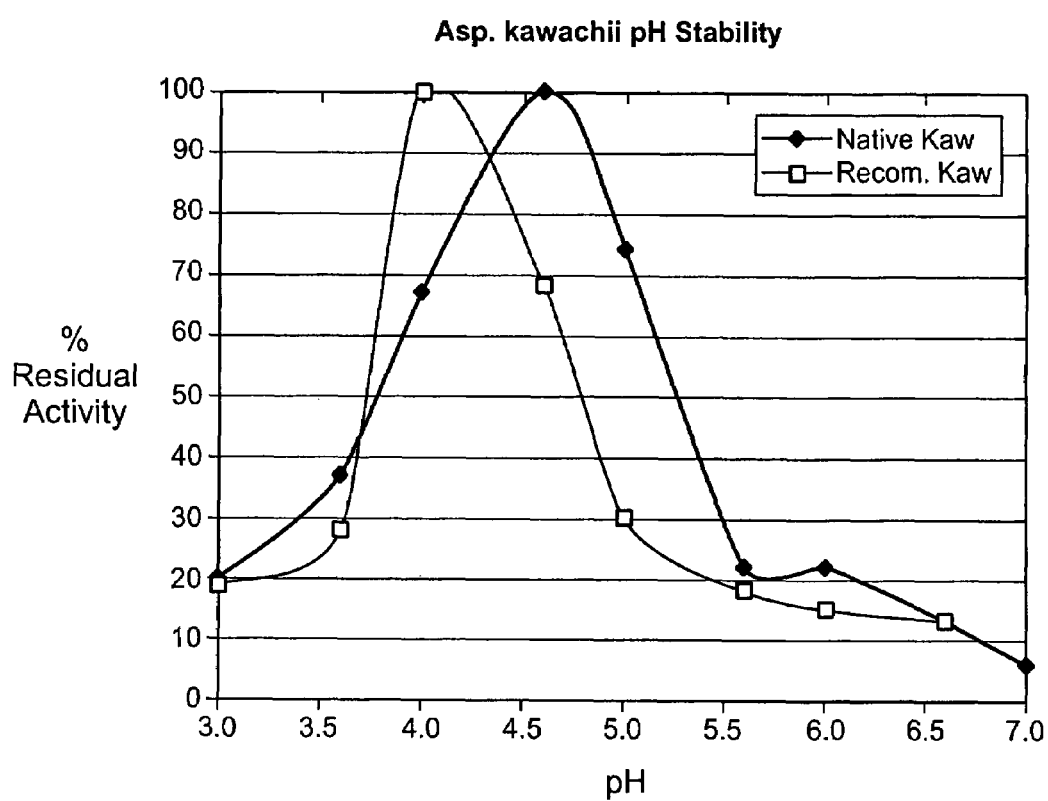
FIG. 7 illustrates the pH stability as % residual activity for the native *Aspergillus kawachi* (nAk-AsaA) and the expressed *A. kawachi* (rAk-AsaA) in the *T. reesei* host (SEQ ID NO:3), as described in Example 6.

Comparison of pH Stability from AkAA Obtained from the Native *Aspergillus* Host and a *Trichoderma reesei* Host Samples of AkAA recombinantly produced in a *Trichoderma reesei* (Tr-asaA) as described above and samples of native asaA were diluted to equal protein concentrations with 20 mM acetate buffer at pH 4.5. Reactions were run in 100 mM citrate/NaOH buffers at 50° C. for 30 minutes at pH levels 3 to 7. 1.0 mL of the reaction was added to 5 mL of 10% corn starch (Cargill Foods, MN) in 100 mM acetate, pH 4.5 in sample tubes. The tubes were shaken at 50° C. for 20 minutes. Then 0.5 mL 2.0% NaOH was added. Tubes were spun and 0.5 mL of the supernatant were assayed for reducing sugars using the Dinito Salicylic Acid (DNS) Assay (Goto et al., (1994) supra). The results are depicted in FIG. 7. The r-asaA exhibited 100% residual activity at pH 3.9. In comparison the n-asaA exhibited 100% residual activity at pH 4.5.

Example 7

Ethanol Production from a Non-cooked Whole Ground Corn Substrate During SSF with *Trichoderma reesei* Expressing AkAA AkAA produced in *Trichoderma reesei* was evaluated at two levels of glucoamylase (GA) from a cell free culture filtrate (0.5 and 1.0 GAU/g). The glucoamylase was obtained from an *Aspergillus niger* composition. Thirty six percent corn flour slurry was prepared containing dry corn steep (2.5% of corn flour). The pH of the slurry was adjusted to 4.8 with dilute sulfuric acid. The total dry solids of the slurry were 33.85%. Fermentations were carried out in 125 ml flasks containing 100 gm of mash (slurry). The desired levels of enzymes were added then 3 ml of propagated yeast slurry was added to start the fermentation. The yeast inoculum was prepared by adding 0.26 gm of dry Fali yeast to 100 gm of mash containing GA activity at 0.9 GAU/g of raw material solids. This slurry was placed in a 32° C. water bath and gently mixed for about 17 hours. At various time intervals samples of the fermentation (beer) were taken for HPLC analysis. After 72 hours, the fermentations were terminated and the beer was dried at 60° C. to obtain the distillers dry grains plus solubles (DDGS).

The starch content of the DDGS was determined and the insoluble solids of the beer after terminating the fermentation were spot checked for starch by the addition of Iodine. Table 2 summarizes ethanol levels, iodine stain of the mash solids and % starch of the DDGS.

TABLE 2

Effect of asaA During Conversion of Granular Corn Starch to Ethanol under Yeast Fermentation Conditions

| GA GAU/ g ds | asaA SSU/ g ds | % v/v EtOH 24 hr | % v/v EtOH 50 hr | % v/v EtOH 72 hr | % starch DDGS | Iodine |
|---|---|---|---|---|---|---|
| 0.5 |  | 7.7 | 11.4 | 13.7 | 27.4 | + |
| 0.5 | 0.25 | 9.2 | 14.7 | 16.9 | 7.7 | + |
| 0.5 | 0.50 | 9.6 | 15.4 | 17.0 | 5.7 | +/− |
| 0.5 | 1.0 | 10.0 | 16.2 | 17.3 | 4.1 | +/−− |
| 0.5 | 2.0 | 10.9 | 16.5 | 17.5 | 2.8 | − |
| 0.5 | 3.0 | 11.2 | 16.8 | 17.5 | 1.6 | − |
| 0.5 | 4.0 | 11.2 | 16.9 | 17.4 | 1.7 | − |
| 0.5 | 5.0 | 11.2 | 17.0 | 17.7 | 1.5 | − |
| 1.0 |  | 9.3 | 14.4 | 16.2 | 13.0 | + |
| 1.0 | 0.25 | 11.6 | 17.1 | 17.8 | 3.6 | +/−− |
| 1.0 | 0.5 | 12.1 | 16.8 | 17.9 | 2.6 | − |
| 1.0 | 1.0 | 12.7 | 17.2 | 17.7 | 2.2 | − |
| 1.0 | 2.0 | 12.7 | 17.6 | 17.8 | 1.6 | − |
| 1.0 | 3.0 | 12.9 | 17.5 | 17.8 | 1.1 | − |
| 1.0 | 4.0 | 13.2 | 17.5 | 17.9 | 0.8 | − |
| 1.0 | 5.0 | 13.3 | 17.2 | 17.9 | 1.1 | − |

Example 8

Conversion of Granular Starch Substrates by Glucoamylase and Alpha Amylases

Commercial alpha amylases from different sources were compared with Tr-asaA under the simultaneous saccharification and fermentation conditions in the presence of glucoamylase from a commercial source of GA at 0.5 GAU/g of ds. The activity of the commercial alpha amylases was determined using the soluble starch substrate (SSU) method assay as described earlier.

Ethanol fermentation was carried out using whole ground corn as described in Example 7. Alpha amylases from various sources were added at 1.0 SSU/g of ground corn and glucoamylase was added at 0.5 GAU/g.

Alpha amylases included AkAA expressed and produced from *T. reesei* having SSU/ml, 90; SPEZYME LT AA (*Bacillus amyloliquefaciens*) having SSU/ml, 2,759); SPEZYME FRED (*Bacillus licheniformis*) having SSU/ml, 4,842; SPEZYME Ethyl (*Bacillus stearothermophilus*) having SSU/ml, 22,082; and CLARASE L (*Aspergillus oryzae*) having SSU/ml, 23,087.

The samples were taken during the course of the fermentation and analyzed for ethanol content. After the fermentation, the insoluble solids (DDGS) were separated and the residual starch content of the corn mash at pH 5.0 was determined. The results are summarized in Table 3.

TABLE 3

| Alpha Amylase at (1.0 SSU/g ds) | Ave % v/v EtOH | | | Residual % starch in DDGS 72 hr |
|---|---|---|---|---|
|  | 22 hr | 46 hr | 72 hr |  |
| — | 7.77 | 11.56 | 14.44 | 29.8 |
| SPEZYME LT-AA | 7.72 | 11.56 | 14.78 | 30.8 |
| SPEZYME FRED | 7.84 | 11.77 | 14.59 | 30.8 |
| SPEZYME Ethyl | 7.94 | 11.82 | 14.57 | 29.1 |

TABLE 3-continued

| | Ave % v/v EtOH | | | Residual % starch in DDGS |
|---|---|---|---|---|
| Alpha Amylase at (1.0 SSU/g ds) | 22 hr | 46 hr | 72 hr | 72 hr |
| CLARASE L | 7.94 | 11.72 | 14.62 | 30.8 |
| AkAA | 9.57 | 15.75 | 18.44 | 9.0 |

Example 9

Effect of Substrate Treatment on the Ethanol Yield and Composition of Distilleries Dry Grain Solids, (DDGS)

Whole ground corn substrate was subjected to a conventional dry milling process for fuel alcohol fermentation using a hammer mill to reduce particle size. Three different mashes were prepared.

Treatment 1 (Trt 1) is a high temperature treatment, which involved a batch liquefaction of a 36% ds corn flour slurry containing 0.9% dry corn steep (DCS) with 3.5 U/g SPEZYME ETHYL at pH 5.6 by jet cooking according to the prior art procedures. The slurry was place in a 90° C. bath for 1.5 hours, mixed and then cooled to 30° C. with a pH adjustment to 5.0 with dilute sulfuric acid. The slurry was further diluted with water to 32.71% ds.

Treatment 2 (Trt 2) is a low temperature treatment. The mash was prepared by incubating a 36% corn flour slurry containing 0.9% DCS with the pH adjusted to 5.0 with dilute sulfuric acid at 60° C. for three hours. Prior to incubation 0.05 GAU/g of glucoamylase was added.

Treatment 3 (Trt 3) is a room temperature treatment (no heat treatment)—a corn slurry was obtained at room temperature prior to use in the fermentation with 0.5 GAU glucoamylase/g of corn and 1.0 SSU/g corn of AkAA produced in *Trichoderma reesei*.

Yeast fermentation was then carried out on each treatment as described in example 7.

After the fermentation, ethanol yield was determined and the insoluble solids from each treatment were separated by centrifugation, dried at 60° C. and the total carbohydrate content and nitrogen content were determined. The results are illustrated in Table 4.

TABLE 4

Comparison of ethanol yield and the composition of DDGS of different treatments of whole ground corn substrate under ethanol fermentation using yeast

| Corn Mash Treatment | Kgs DDGS/MT corn | % Residual starch content in DDGS | % Total Protein in DDGS | Ethanol L/MT corn |
|---|---|---|---|---|
| Trt 1 | 326 | 4.8 | 27.5 | 402 |
| Trt 2 | 299 | 3.8 | 29.5 | 429 |
| Trt 3 | 274 | 3.5 | 31.6 | 438 |

Example 10

Ethanol Production from Fermentations with *Aspergillus niger* Alpha-Amylase and Glucoamylase Co-Expressing Transformants Ethanol production (% v/v) was evaluated at a glucoamylase dosing level of 0.75 GAU/g ds and at an alpha-amylase dosing level of 9.90 SSU/g ds for transformant #10 and 4.29 SSU/g ds for transformant #26 (see Example 5B, transformant #10 and transformant #26). A 100 g corn slurry having 33% DS was prepared from Azure corn flour (8.95% moisture). The pH of the slurry was adjusted to pH 4.5 and fermentations were carried out with the addition of 1 mL of 20% Fali yeast (400 ppm) at 32° C. in 125 ml flasks. Ethanol (% v/v) in the supernatant was measured at 24, 48 and 70 hours.

TABLE 5

| Transformant | Sample Time (hrs) | Ethanol (% v/v) |
|---|---|---|
| #10 (replicate 1) | 24 | 13.76 |
| | 48 | 17.62 |
| | 70 | 18.26 |
| #10 (replicate 2) | 24 | 14.36 |
| | 48 | 17.88 |
| | 70 | 18.46 |
| #26 (replicate 1) | 24 | 13.47 |
| | 48 | 17.54 |
| | 70 | 18.52 |
| #26 (replicate 2) | 24 | 13.33 |
| | 48 | 17.25 |
| | 70 | 18.19 |

The invention claimed is:

1. An *Aspergillus* fungal strain comprising DNA encoding an endogenous glucoamylase and DNA encoding a heterologous alpha amylase comprising an amino acid sequence having at least 99% sequence identity to SEQ ID NO: 9, wherein both the glucoamylase and the heterologous alpha amylase are expressed and secreted by the *Aspergillus* fungal strain.

2. The *Aspergillus* strain of claim 1, wherein the strain is an *A. niger*, *A. nidulans*, *A. oryzae* or *A. awamori* strain.

3. The *Aspergillus* strain of claim 2, wherein the strain is an *A. niger* strain.

4. The *Aspergillus* strain of claim 2, wherein the secreted glucoamylase comprises at least 40% of the total amount of secreted protein from the strain.

5. A culture medium comprising the *Aspergillus* strain of claim 1.

6. An *Aspergillus* strain comprising a) DNA encoding an endogenous glucoamylase and b) DNA encoding a heterologous alpha amylase, which comprises at least 99% sequence identity to SEQ ID NO: 9, wherein the *Aspergillus* strain expresses both the glucoamylase and the heterologous alpha amylase and overproduces the glucoamylase.

7. A culture medium comprising the *Aspergillus* strain of claim 6.

8. A method of producing an alpha amylase in an *Aspergillus* cell which comprises, culturing the *Aspergillus* fungal strain of claim 1 under conditions suitable for the expression and production of the heterologous alpha amylase and producing the heterologous alpha amylase.

9. The method according to claim 8, wherein the *Aspergillus* is an *A. niger* strain.

10. The method according to claim 8, further comprising producing said glucoamylase and recovering the produced alpha amylase and glucoamylase.

11. The method according to claim 8, wherein the *Aspergillus* strain is an glucoamylase overproducing strain.

12. A method for producing an acid stable alpha amylase and a glucoamylase in a filamentous fungal host cell comprising a) obtaining the fungal strain of claim 1
b) cultivating the *Aspergillus* strain in a suitable culture medium to allow expression of the alpha amylase and the glucoamylase, and
c) producing the alpha amylase and the glucoamylase.

13. The method according to claim 12 further comprising recovering the produced glucoamylase and alpha amylase.

14. The method according to claim 12, wherein the *Aspergillus* strain is an *A. niger* strain.

15. The method according to claim 12, wherein the secreted glucoamylase comprises at least 40% of the total amount of protein from the strain.

16. The *Aspergillus* fungal strain of claim 1, wherein the DNA encodes a heterologous alpha amylase comprising the amino acid sequence of SEQ ID NO: 9.

17. The *Aspergillus* strain of claim 4, wherein the secreted glucoamylase comprises at least 50% of the total amount of secreted protein from the strain.

18. The *Aspergillus* strain of claim 6, wherein the *Aspergillus* is an *A. niger* strain.

* * * * *